United States Patent
Bacon et al.

(10) Patent No.: US 8,648,067 B2
(45) Date of Patent: Feb. 11, 2014

(54) SUBSTITUTED PHENOXYPROPYLCYCLOAMINE DERIVATIVES AS HISTAMINE-3 ($H_3$) RECEPTOR LIGANDS

(75) Inventors: Edward R. Bacon, Audubon, PA (US); Thomas R. Bailey, Phoenixville, PA (US); Sankar Chatterjee, Wynnewood, PA (US); Derek D. Dunn, Coatesville, PA (US); Greg A. Hostetler, Newark, DE (US); Robert L. Hudkins, Chester Springs, PA (US); Brigitte Lesur, Saint Germain en Laye (FR); Babu G. Sundar, West Chester, PA (US); Allison L. Zulli, Wayne, PA (US); Christophe Yue, Vincennes (FR)

(73) Assignees: Cephalon, Inc., Frazer, PA (US); Teva Sante, Paris (FR)

( * ) Notice: Subject to any disclaimer, the term of this patent is extended or adjusted under 35 U.S.C. 154(b) by 0 days.

(21) Appl. No.: 13/334,311

(22) Filed: Dec. 22, 2011

(65) Prior Publication Data

US 2012/0238551 A1    Sep. 20, 2012

Related U.S. Application Data

(63) Continuation of application No. PCT/US2010/040757, filed on Jul. 1, 2010.

(60) Provisional application No. 61/222,602, filed on Jul. 2, 2009.

(51) Int. Cl.
| | | |
|---|---|---|
| *A61K 31/55* | (2006.01) |
| *A61K 31/54* | (2006.01) |
| *A61K 31/45* | (2006.01) |
| *A61K 31/535* | (2006.01) |
| *A61K 31/497* | (2006.01) |
| *A61K 31/545* | (2006.01) |
| *A61K 31/445* | (2006.01) |
| *A01N 43/40* | (2006.01) |
| *C07D 223/18* | (2006.01) |
| *C07D 279/10* | (2006.01) |
| *C07D 413/00* | (2006.01) |
| *C07D 403/00* | (2006.01) |
| *C07D 401/00* | (2006.01) |
| *C07D 217/00* | (2006.01) |
| *C07D 211/00* | (2006.01) |
| *C07D 405/00* | (2006.01) |
| *C07D 295/00* | (2006.01) |

(52) U.S. Cl.
USPC .............. 514/213; 514/227.8; 514/233.2; 514/235.5; 514/253.01; 514/254.01; 514/316; 514/323; 514/326; 540/593; 544/58.6; 544/117; 544/130; 544/141; 544/295; 544/360; 546/146; 546/188; 546/200; 546/208; 548/518

(58) Field of Classification Search
USPC ........... 514/213, 213.01, 227.8, 233.2, 235.5, 514/252.19, 253.01, 254.01, 316, 323, 326; 548/575, 518; 546/236, 237, 146, 188, 546/200, 208; 544/398, 399, 58.6, 117, 544/130, 141, 295, 360
See application file for complete search history.

(56) References Cited

U.S. PATENT DOCUMENTS

| 3,910,916 | A | 10/1975 | Protiva et al. |
| 2006/0052597 | A1 * | 3/2006 | Best et al. .............. 544/122 |
| 2007/0105838 | A1 * | 5/2007 | Best et al. ............ 514/217.01 |

FOREIGN PATENT DOCUMENTS

| FR | 2211254 | 7/1974 | |
| WO | WO0006254 A2 * | 2/2000 | ....... A61R 31/4453 |
| WO | WO 2004/035556 | 4/2004 | |
| WO | WO 2008013838 A2 * | 1/2008 | ........ C07D 217/00 |

OTHER PUBLICATIONS

Apelt, J., et al. Search for Histamine H3 receptor antagonists with combined inhibitory potency at N-methyltransferase: ether derivatives. Pharmazie vol. 60 pp. 97-106. Published 2005.*
Apelt, J. et al. Pharmazie, vol. 60, pp. 97-016. Published 2005.*
Berlin, M. et al., "Recent advances in the development of histamine H-3 antagonists", Expert Opin. Ther. Targets, Ashley Publications, 2007, 17(6), pp. 675-687.
Faghih, R. et al, "Structure-Activity Relationships of Non-imidazole H3 Receptor Ligands, Part 1", Biorg. Med. Chem. Lett. 12, 2002, pp. 2031-2034.

* cited by examiner

*Primary Examiner* — Paul Zarek
*Assistant Examiner* — George W Kosturko
(74) *Attorney, Agent, or Firm* — John P. White; Gary J. Gershik; Cooper & Dunham LLP

(57) ABSTRACT

The present invention provides compounds of formula I:

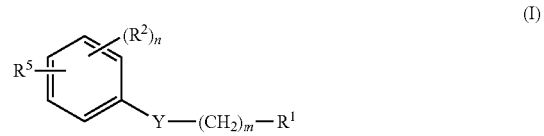

their use as $H_3$ antagonists/inverse agonists, processes for their preparation, and pharmaceutical compositions thereof.

21 Claims, No Drawings

SUBSTITUTED PHENOXYPROPYLCYCLOAMINE DERIVATIVES AS HISTAMINE-3 (H₃) RECEPTOR LIGANDS

FIELD OF THE INVENTION

The present invention is related to substituted phenoxypropylcycloamine derivatives, their use as $H_3$ antagonists/inverse agonists, processes for their preparation, and pharmaceutical compositions comprising them.

BACKGROUND OF THE INVENTION

Publications cited throughout this disclosure are incorporated in their entirety herein by reference.

Histamine is a well established modulator of neuronal activity. At least four subtypes of histamine receptors have been reported in the literature—$H_1$, $H_2$, $H_3$, $H_4$. The histamine $H_3$ receptors play a key role in neurotransmission in the central nervous system. The $H_3$ receptor was discovered in 1983 originally on histamine-containing neurons where it was shown to function presynaptically, regulating the release and synthesis of the biogenic amine histamine, now a well established neurotransmitter. (Arrang, J. M.; Garbarg, M.; Schwartz, J. C., Auto-inhibition of brain histamine release mediated by a novel class ($H_3$) of histamine receptor. *Nature* 1983, 302, (5911), 832-7) $H_3$ receptors are predominately expressed in the brain, localizing to the cerebral cortex, amygdala, hippocampus, striatum, thalamus and hypothalamus. $H_3$ receptors are also localized presynaptically on histaminergic nerve terminals and act as inhibitory autoreceptors (Alguacil L. F.; Perez-Garcia C. Histamine $H_3$ Receptor: A potential drug target for the treatment of central nervous systems disorders. *Current Drug Targets-CNS & Neurological Disorders* 2003, 2, 303-131; Passani, M. B.; Lin, J. S.; Hancock, A.; Crochet, S.; Blandina, P., The histamine $H_3$ receptor as a novel therapeutic target for cognitive and sleep disorders. *Trends Pharmacol Sci* 2004, 25, 618-25; Leurs, R.; Bakker, R. A.; Timmerman, H.; de Esch, I. J., The histamine $H_3$ receptor: from gene cloning to $H_3$ receptor drugs. *Nat Rev Drug Discov* 2005, 4, (2), 107-20; Celanire, S.; Wijtmans, M.; Talaga, P.; Leurs, R.; de Esch, I. J., Keynote review: histamine $H_3$ receptor antagonists reach out for the clinic. *Drug Discov Today* 2005, 10, (23-24), 1613-27; Witkin, J. M.; Nelson, D. L., Selective histamine $H_3$ receptor antagonists for treatment of cognitive deficiencies and other disorders of the central nervous system. *Pharmacol Ther* 2004, 103, 1-20). When these receptors are activated by histamine, histamine release is inhibited. $H_3$ receptors can also be found in the periphery (skin, lung, cardiovascular system, intestine, GI tract, etc). $H_3$ receptors are also involved in presynaptic regulation of the release of acetylcholine, dopamine, GABA, glutamate and serotonin (see Repka-Ramirez M. S. New concepts of histamine receptors and actions. Current Allergy and Asthma Reports 2003, 3, 227-231; Chazot P. L.; Hann V. $H_3$ histamine receptor isoforms: New therapeutic targets in the CNS? *Current Opinions in Investigational Drugs* 2001, 2, 1428-1431; Leurs R.; Blandina P.; Tedford C.; Timmerman H. Therapeutic potential of histamine $H_3$ receptor agonists and antagonists. *Trends in Pharmacology* 1998, 19, 177-183). The $H_3$ receptor demonstrates a high degree of constitutive or spontaneous activity (e.g., receptor is active in the absence of agonist stimulation) in vitro and in vivo, thus, ligands to the receptor can display, agonist, neutral antagonist or inverse agonist effects.

The location and function of histaminergic neurons in the CNS suggests that compounds interacting with the $H_3$ receptor may have utility in a number of therapeutic applications including narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders and epilepsy (Leurs et al, 2005; Witkin and Nelson, 2004; Hancock, A. A.; Fox, G. B. Perspectives on cognitive domains, $H_3$ receptor ligands and neurological disease. *Expert Opin. Investig. Drugs,* 2004, 13, 1237-1248; Esbenshade, T. A.; ox, G. B.; Cowart, M. D. Histamine $H_3$ receptor antagonists: Preclinical promise for treating obesity and cognitive disorders. *Molecular interventions* 2006, 6, 77-88). An $H_3$ antagonist/inverse agonist could be important for gastrointestinal disorders, respiratory disorders such as asthma, inflammation, and myocardial infarction.

Thus, there is a need for novel classes of compounds that possess the beneficial properties. It has been discovered that compounds of the present invention, referred to herein as substituted phenoxypropylcycloamine derivatives, are useful as agents for treating or preventing various diseases or disorders disclosed herein.

SUMMARY OF THE INVENTION

The present invention in one aspect is directed to novel compounds of Formula I which are useful as $H_3$ antagonists/inverse agonists. These compounds have the structure:

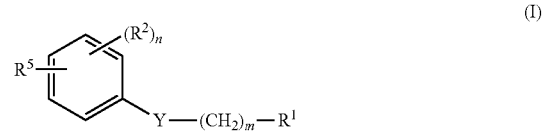

and its stereoisomeric forms, mixtures of stereoisomeric forms, or pharmaceutically acceptable salt forms thereof, wherein the constituent members are as defined herein.

The compounds of the present invention may be used to treat the following diseases and disorders: narcolepsy or other sleep/wake disorders, such as obstructive sleep apnea/hypopnea syndrome, and shift work sleep disorder; feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders (such as asthma), inflammation, and myocardial infarction.

In another aspect, the present invention is directed to a pharmaceutical composition which comprises a pharmaceutically acceptable carrier and a compound of the present invention, preferably in a therapeutically effective amount.

DETAILED DESCRIPTION OF THE INVENTION

Thus, in a first embodiment, the present invention provides novel compounds of Formula I:

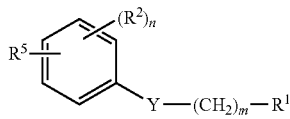

wherein:
R¹ is a 3 to 10 membered heterocycloalkyl ring containing 1 nitrogen atom and optionally a
second nitrogen atom or an oxygen atom, wherein $R^1$ is optionally substituted with one to three $R^{20}$ groups;
$R^2$ at each occurrence is independently F, Cl, Br, I, $OR^{21}$, $NR^{23}R^{24}$, $NO_2$, CN, $CF_3$, $C_1$-$C_6$ alkyl, C(=O)$R^{25}$, $CO_2R^{25}$, or C(=O)$NR^{23}R^{24}$;
$R^3$ is H or $C_1$-$C_6$ alkyl, or $R^3$ can combine with A to form a 5 or 6 membered heterocycloalkyl
ring containing 1 or 2 nitrogen atoms, wherein said heterocycloalkyl ring is optionally substituted with one to three $R^{20}$ groups;
$R^4$ is H or $C_1$-$C_6$ alkyl;
$R^5$ is

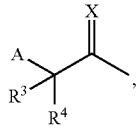

wherein $R^5$ is para or meta to Y;
X is O or $NOR^{10}$;
Y is selected from $S(O)_q$, O, and $NR^{11}$;
$R^{10}$ is H, $C_1$-$C_4$ alkyl, cycloalkyl, or arylalkyl;
$R^{11}$ is H, $C_1$-$C_6$ alkyl, C(=O)$R^{25}$, $CO_2R^{25}$;
A is selected from pyrrolidin-1-yl; piperidin-1-yl; morpholin-4-yl; piperazin-1-yl; thiomorpholin-4-yl; 2,3-dihydro-indol-1-yl; 1,3-dihydro-isoindol-2-yl; 3,4-dihydro-2H-quinolin-1-yl; 3,4-dihydro-1H-isoquinolin-2-yl; 2,3,4,5-tetrahydro-benzo[b]azepin-1-yl; indol-1-yl; and benzoimidazol-1-yl;
wherein A can be optionally substituted with one to three $R^{20}$ groups;
or A can combine with $R^3$ to form a 5 or 6 membered heterocycloalkyl ring containing 1 or 2 nitrogen
atoms, wherein said heterocycloalkyl ring is optionally substituted with one to three $R^{20}$ groups;
$R^{20}$ at each occurrence is independently, F, Cl, Br, I, $OR^{21}$, $OR^{22}$, $NR^{23}R^{24}$, NHOH, $NO_2$, CN,
$CF_3$, $C_1$-$C_6$ alkyl optionally substituted with $OR^{21}$, $C_2$-$C_6$ alkenyl, $C_2$-$C_6$ alkynyl, $C_3$-$C_7$ cycloalkyl, 3-7 membered heterocycloalkyl, aryl, 5 or 6 membered heteroaryl, arylalkyl, (=O), C(=O)$R^{26}$, $CO_2R^{28}$, OC(=O)$R^{25}$, C(=O)$NR^{23}R^{24}$, $NR^{27}C$(=O)$R^{25}$, $NR^{27}C$(=O)$OR^{25}$, OC(=O)$NR^{23}R^{24}$, $NR^{27}C$(=S)$R^{25}$, or $S(O)_qR^{25}$, wherein said aryl groups are optionally substituted with one to three $R^{30}$ groups;
$R^{21}$ at each occurrence is independently H, $C_1$-$C_6$ alkyl, aryl, or arylalkyl;
$R^{22}$ at each occurrence is independently the residue of an amino acid after the hydroxyl group
of the carboxyl group is removed;
$R^{23}$ and $R^{24}$ at each occurrence are each independently selected from H, $C_1$-$C_6$ alkyl, and aryl,
or $R^{23}$ and $R^{24}$, together with the nitrogen atom to which they are attached, form a 3 to 7 membered heterocyclic ring optionally substituted with =O;
$R^{25}$ at each occurrence is independently $C_1$-$C_6$ alkyl, aryl, or arylalkyl;
$R^{26}$ at each occurrence is independently $NR^{23}R^{24}$, $CF_3$, $C_1$-$C_6$ alkyl, $C_3$-$C_7$ cycloalkyl, 3-7 membered heterocycloalkyl, aryl, 5-10 membered heteroaryl, or arylalkyl, wherein said alkyl, cycloalkyl, heterocycloalkyl, aryl, and heteroaryl groups are optionally substituted with one to three $R^{30}$ groups;
$R^{27}$ at each occurrence is independently H or $C_1$-$C_6$ alkyl;
$R^{28}$ at each occurrence is independently $C_1$-$C_6$ alkyl, aryl, or arylalkyl, wherein said groups
are optionally substituted with one to three $R^{30}$ groups;
$R^{30}$ at each occurrence is independently F, Cl, Br, I, $OR^{21}$, $OR^{22}$, $NR^{23}R^{24}$, NHOH, $NO_2$, CN,
$CF_3$, $C_1$-$C_6$ alkyl, aryl, or arylalkyl;
n is 0, 1, 2, 3, or 4;
m is 0, 1, 2, 3, 4, or 5;
q is 0, 1, or 2;
or a stereoisomer or a pharmaceutically acceptable salt thereof.

In another embodiment, the present invention provides novel compounds of Formula Ia:

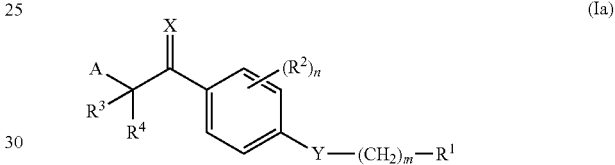

wherein:
R¹ is a 3 to 10 membered heterocycloalkyl ring containing 1 nitrogen atom and optionally a
second nitrogen atom or an oxygen atom, wherein $R^1$ is optionally substituted with one to three $R^{20}$ groups;
$R^2$ at each occurrence is independently F, Cl, Br, I, $OR^{21}$, $NR^{23}R^{24}$, $NO_2$, CN, $CF_3$, $C_1$-$C_6$ alkyl, C(=O)$R^{25}$, $CO_2R^{25}$, or C(=O)$NR^{23}R^{24}$;
$R^3$ is H or $C_1$-$C_6$ alkyl, or $R^3$ can combine with A to form a 5 or 6 membered heterocycloalkyl
ring containing 1 or 2 nitrogen atoms, wherein said heterocycloalkyl ring is optionally substituted with one to three $R^{20}$ groups;
$R^4$ is H or $C_1$-$C_6$ alkyl;
X is O or $NOR^{10}$;
Y is selected from $S(O)_q$, O, and $NR^{11}$;
$R^{10}$ is H, $C_1$-$C_4$ alkyl, cycloalkyl, or arylalkyl;
$R^{11}$ is H, $C_1$-$C_6$ alkyl, C(=O)$R^{25}$, $CO_2R^{25}$;
A is selected from pyrrolidin-1-yl; piperidin-1-yl; morpholin-4-yl; piperazin-1-yl; thiomorpholin-4-yl; 2,3-dihydro-indol-1-yl; 1,3-dihydro-isoindol-2-yl; 3,4-dihydro-2H-quinolin-1-yl; 3,4-dihydro-1H-isoquinolin-2-yl; 2,3,4,5-tetrahydro-benzo[b]azepin-1-yl; indol-1-yl; and benzoimidazol-1-yl;
wherein A can be optionally substituted with one to three $R^{20}$ groups;
or A can combine with $R^3$ to form a 5 or 6 membered heterocycloalkyl ring containing 1 or 2 nitrogen
atoms, wherein said heterocycloalkyl ring is optionally substituted with one to three $R^{20}$ groups;
$R^{20}$ at each occurrence is independently, F, Cl, Br, I, $OR^{21}$, $OR^{22}$, $NR^{23}R^{24}$, NHOH, $NO_2$, CN,
$CF_3$, $C_1$-$C_6$ alkyl optionally substituted with $OR^{21}$, $C_2$-$C_6$ alkenyl, $C_2$-$C_6$ alkynyl, $C_3$-$C_7$ cycloalkyl, 3-7 membered heterocycloalkyl, aryl, 5 or 6 membered heteroaryl, arylalkyl, (=O), C(=O)R$^{26}$, CO$_2$R$^{28}$, OC(=O)R$^{25}$, C(=O)NR$^{23}$R$^{24}$, NR$^{27}$C(=O)R$^{25}$, NR$^{27}$C(=O)OR$^{25}$, OC(=O)NR$^{23}$R$^{24}$, NR$^{27}$C(=S)R$^{25}$, or S(O)$_q$R$^{25}$, wherein said aryl groups are optionally substituted with one to three R$^{30}$ groups;

R$^{21}$ at each occurrence is independently H, C$_1$-C$_6$ alkyl, aryl, or arylalkyl;

R$^{22}$ at each occurrence is independently the residue of an amino acid after the hydroxyl group
of the carboxyl group is removed;

R$^{23}$ and R$^{24}$ at each occurrence are each independently selected from H, C$_1$-C$_6$ alkyl, and aryl,
or R$^{23}$ and R$^{24}$, together with the nitrogen atom to which they are attached, form a 3 to 7 membered heterocyclic ring optionally substituted with =O;

R$^{25}$ at each occurrence is independently C$_1$-C$_6$ alkyl, aryl, or arylalkyl;

R$^{26}$ at each occurrence is independently NR$^{23}$R$^{24}$, CF$_3$, C$_1$-C$_6$ alkyl, C$_3$-C$_7$ cycloalkyl, 3-7
membered heterocycloalkyl, aryl, 5-10 membered heteroaryl, or arylalkyl, wherein said alkyl, cycloalkyl, heterocycloalkyl, aryl, and heteroaryl groups are optionally substituted with one to three R$^{30}$ groups;

R$^{27}$ at each occurrence is independently H or C$_1$-C$_6$ alkyl;

R$^{28}$ at each occurrence is independently C$_1$-C$_6$ alkyl, aryl, or arylalkyl, wherein said groups
are optionally substituted with one to three R$^{30}$ groups;

R$^{30}$ at each occurrence is independently F, Cl, Br, I, OR$^{21}$, OR$^{22}$, NR$^{23}$R$^{24}$, NHOH, NO$_2$, CN,
CF$_3$, C$_1$-C$_6$ alkyl, aryl, or arylalkyl;

n is 0, 1, 2, 3, or 4;

m is 0, 1, 2, 3, 4, or 5;

q is 0, 1, or 2;

or a stereoisomer or a pharmaceutically acceptable salt thereof.

In yet another embodiment, the present invention provides novel compounds of Formula Ib:

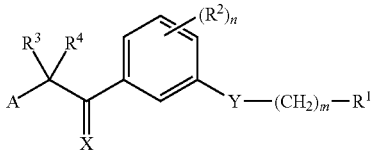

(Ib)

wherein:

R$^1$ is a 3 to 10 membered heterocycloalkyl ring containing 1 nitrogen atom and optionally a
second nitrogen atom or an oxygen atom, wherein R$^1$ is optionally substituted with one to three R$^{20}$ groups;

R$^2$ at each occurrence is independently F, Cl, Br, I, OR$^{21}$, NR$^{23}$R$^{24}$, NO$_2$, CN, CF$_3$, C$_1$-C$_6$
alkyl, C(=O)R$^{25}$, CO$_2$R$^{25}$, or C(=O)NR$^{23}$R$^{24}$;

R$^3$ is H or C$_1$-C$_6$ alkyl, or R$^3$ can combine with A to form a 5 or 6 membered heterocycloalkyl
ring containing 1 or 2 nitrogen atoms, wherein said heterocycloalkyl ring is optionally substituted with one to three R$^{20}$ groups;

R$^4$ is H or C$_1$-C$_6$ alkyl;

X is O or NOR$^{10}$;

Y is selected from S(O)$_q$, O, and NR$^{11}$;

R$^{10}$ is H, C$_1$-C$_4$ alkyl, cycloalkyl, or arylalkyl;

R$^{11}$ is H, C$_1$-C$_6$ alkyl, C(=O)R$^{25}$, CO$_2$R$^{25}$;

A is selected from pyrrolidin-1-yl; piperidin-1-yl; morpholin-4-yl; piperazin-1-yl; thiomorpholin-4-yl; 2,3-dihydro-indol-1-yl; 1,3-dihydro-isoindol-2-yl; 3,4-dihydro-2H-quinolin-1-yl; 3,4-dihydro-1H-isoquinolin-2-yl; 2,3,4,5-tetrahydro-benzo[b]azepin-1-yl; indol-1-yl; and benzoimidazol-1-yl;

wherein A can be optionally substituted with one to three R$^{20}$ groups;

or A can combine with R$^3$ to form a 5 or 6 membered heterocycloalkyl ring containing 1 or 2 nitrogen
atoms, wherein said heterocycloalkyl ring is optionally substituted with one to three R$^{20}$ groups;

R$^{20}$ at each occurrence is independently, F, Cl, Br, I, OR$^{21}$, OR$^{22}$, NR$^{23}$R$^{24}$, NHOH, NO$_2$, CN,
CF$_3$, C$_1$-C$_6$ alkyl optionally substituted with OR$^{21}$, C$_2$-C$_6$ alkenyl, C$_2$-C$_6$ alkynyl, C$_3$-C$_7$ cycloalkyl, 3-7 membered heterocycloalkyl, aryl, 5 or 6 membered heteroaryl, arylalkyl, (=O), C(=O)R$^{26}$, CO$_2$R$^{28}$, OC(=O)R$^{25}$, C(=O)NR$^{23}$R$^{24}$, NR$^{27}$C(=O)R$^{25}$, NR$^{27}$C(=O)OR$^{25}$, OC(=O)NR$^{23}$R$^{24}$, NR$^{27}$C(=S)R$^{25}$, or S(O)$_q$R$^{25}$, wherein said aryl groups are optionally substituted with one to three R$^{30}$ groups;

R$^{21}$ at each occurrence is independently H, C$_1$-C$_6$ alkyl, aryl, or arylalkyl;

R$^{22}$ at each occurrence is independently the residue of an amino acid after the hydroxyl group
of the carboxyl group is removed;

R$^{23}$ and R$^{24}$ at each occurrence are each independently selected from H, C$_1$-C$_6$ alkyl, and aryl,
or R$^{23}$ and R$^{24}$, together with the nitrogen atom to which they are attached, form a 3 to 7 membered heterocyclic ring optionally substituted with =O;

R$^{25}$ at each occurrence is independently C$_1$-C$_6$ alkyl, aryl, or arylalkyl;

R$^{26}$ at each occurrence is independently NR$^{23}$R$^{24}$, CF$_3$, C$_1$-C$_6$ alkyl, C$_3$-C$_7$ cycloalkyl, 3-7
membered heterocycloalkyl, aryl, 5-10 membered heteroaryl, or arylalkyl, wherein said alkyl, cycloalkyl, heterocycloalkyl, aryl, and heteroaryl groups are optionally substituted with one to three R$^{30}$ groups;

R$^{27}$ at each occurrence is independently H or C$_1$-C$_6$ alkyl;

R$^{28}$ at each occurrence is independently C$_1$-C$_6$ alkyl, aryl, or arylalkyl, wherein said groups
are optionally substituted with one to three R$^{30}$ groups;

R$^{30}$ at each occurrence is independently F, Cl, Br, I, OR$^{21}$, OR$^{22}$, NR$^{23}$R$^{24}$, NHOH, NO$_2$, CN,
CF$_3$, C$_1$-C$_6$ alkyl, aryl, or arylalkyl;

n is 0, 1, 2, 3, or 4;

m is 0, 1, 2, 3, 4, or 5;

q is 0, 1, or 2;

or a stereoisomer or a pharmaceutically acceptable salt thereof.

In preferred embodiments, X is O. In other preferred embodiments, X is NOR$^{10}$. In other embodiments, Y is O and m is 3. In still other embodiments, X is O, Y is O, and m is 3.

Certain preferred embodiments of the present invention include compounds where R$^1$ is a
pyrrolidin-1-yl, piperidin-1-yl, piperazin-1-yl or morpholin-4-yl group, wherein said groups are optionally substituted with 1 to 3 R$^{20}$ groups. In other preferred embodiments, R$^1$ is a pyrrolidin-1-yl or piperidin-1-yl group, wherein said groups are optionally substituted with 1 to 3 R$^{20}$ groups. In other embodiments, R$^1$ is 2-methyl-pyrrolidin-1-yl.

In most preferred embodiments, A is pyrrolidin-1-yl, piperidin-1-yl, morpholin-4-yl, piperazin-1-yl, or thiomorpholin-4-yl wherein said groups are optionally substituted with 1 to 3 R$^{20}$ groups. In other preferred embodiments of the present invention, Y is O, m is 3 and A is pyrrolidin-1-yl, piperidin-1-yl, morpholin-4-yl, or piperazin-1-yl.

In still other embodiments, A is 3,4-dihydro-1H-isoquinolin-2-yl; 1,3-dihydro-isoindol-2-yl; 3,4-dihydro-2H-quinolin-1-yl; 2,3,4,5-tetrahydro-benzo[b]azepin-1-yl; or 2-methyl-benzoimidazol-1-yl. In other embodiments, X is O, Y is O, and m is 0. In other preferred embodiments, $R^1$ is piperidin-4-yl.

In some preferred embodiments of the present invention, $R^1$ is 1,3-dihydro-isoindol-2-yl; hexahydro-pyrrolo[1,2-a]pyrazin-2-yl; or octahydro-pyrido[1,2-a]pyrazin-2-yl.

Another embodiment of the present invention is directed to novel compounds of Formula Ic:

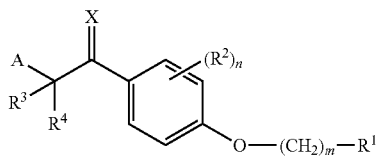

(Ic)

wherein:
$R^1$ is pyrrolidin-1-yl, piperidin-1-yl, piperazin-1-yl, morpholin-4-yl, 1,3-dihydroisoindol-2-yl,
hexahydro-pyrrolo[1,2-a]pyrazin-2-yl, or octahydro-pyrido[1,2-a]pyrazin-2-yl, wherein $R^1$ is optionally substituted with one to three $R^{20}$ groups;
$R^2$ at each occurrence is independently F, Cl, $OR^{21}$, or $C_1$-$C_6$ alkyl;
$R^3$ is H or $C_1$-$C_6$ alkyl, or $R^3$ can combine with A to form a 5 or 6 membered heterocycloalkyl
ring containing 1 or 2 nitrogen atoms, wherein said heterocycloalkyl ring is optionally substituted with one to three $R^{20}$ groups;
$R^4$ is H or $C_1$-$C_6$ alkyl;
X is O or $NOR^{16}$;
$R^{10}$ is H, $C_1$-$C_4$ alkyl, cycloalkyl, or arylalkyl;
A is selected from pyrrolidin-1-yl; piperidin-1-yl; morpholin-4-yl; piperazin-1-yl; thiomorpholin-4-yl; 1,3-dihydroisoindol-2-yl; 3,4-dihydro-2H-quinolin-1-yl; 3,4-dihydro-1H-isoquinolin-2-yl; 2,3,4,5-tetrahydro-benzo[b]azepin-1-yl; and benzoimidazol-1-yl;
wherein A can be optionally substituted with one to three $R^{20}$ groups;
or A can combine with $R^3$ to form a 5 or 6 membered heterocycloalkyl ring containing 1 or 2 nitrogen atoms, wherein said heterocycloalkyl ring is optionally substituted with one to three $R^{20}$ groups;
$R^{20}$ at each occurrence is independently, F, CN, $CF_3$, $C_1$-$C_6$ alkyl optionally substituted with
$OR^{21}$, phenyl, 5 or 6 membered heteroaryl, (=O), C(=O) $R^{26}$, $CO_2R^{28}$, C(=O)$NR^{23}R^{24}$, or $S(O)_2R^{25}$, wherein said phenyl group is optionally substituted with one to three $R^{30}$ groups;
$R^{21}$ at each occurrence is independently H, $C_1$-$C_6$ alkyl, aryl, or arylalkyl;
$R^{23}$ and $R^{24}$ at each occurrence are each independently H or $C_1$-$C_6$ alkyl;
$R^{25}$ at each occurrence is independently $C_1$-$C_6$ alkyl, aryl, or arylalkyl;
$R^{26}$ at each occurrence is independently $NR^{23}R^{24}$, $CF_3$, $C_1$-$C_6$ alkyl, $C_3$-$C_7$ cycloalkyl, 3-7
membered heterocycloalkyl, aryl, 5-10 membered heteroaryl, or arylalkyl, wherein said alkyl, cycloalkyl, heterocycloalkyl, aryl, and heteroaryl groups are optionally substituted with one to three $R^{30}$ groups;
$R^{28}$ at each occurrence is independently $C_1$-$C_6$ alkyl, aryl, or arylalkyl, wherein said groups
are optionally substituted with one to three $R^{30}$ groups;

$R^{30}$ at each occurrence is independently F, Cl, $CF_3$, $C_1$-$C_6$ alkyl or phenyl;
n is 0, 1, or 2;
m is 0, 1, 2, or 3;
or a stereoisomer or a pharmaceutically acceptable salt thereof.

In preferred embodiments, X is O. In other preferred embodiments, X is $NOR^{10}$. In other embodiments, m is 3. In still other embodiments, X is O and m is 3.

In some preferred embodiments of the present invention, $R^1$ is a pyrrolidin-1-yl or piperidin-1-yl group, wherein said group is optionally substituted with 1 to 3 $R^{20}$ groups. In other preferred embodiments, A is pyrrolidin-1-yl, piperidin-1-yl, morpholin-4-yl, piperazin-1-yl, or thiomorpholin-4-yl wherein said groups are optionally substituted with 1 to 3 $R^{20}$ groups.

In certain preferred embodiments, $R^1$ is pyrrolidin-1-yl, piperidin-1-yl, piperazin-1-yl or morpholin-4-yl and A is pyrrolidin-1-yl, piperidin-1-yl, morpholin-4-yl, piperazin-1-yl, or thiomorpholin-4-yl, wherein said $R^1$ and A are each optionally substituted with 1 to 3 $R^{20}$ groups. In still other embodiments of the present invention, m is 3, $R^1$ is pyrrolidin-1-yl or piperidin-1-yl, and A is pyrrolidin-1-yl, piperidin-1-yl, morpholin-4-yl, or piperazin-1-yl, wherein said $R^1$ and A are each optionally substituted with 1 to 3 $R^{20}$ groups.

Another embodiment of the present invention is directed to compounds of Formula Id:

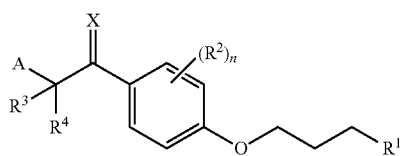

(Id)

wherein:
$R^1$ is pyrrolidin-1-yl, piperidin-1-yl, piperazin-1-yl, or morpholin-4-yl, wherein $R^1$ is
optionally substituted with one to three $R^{20}$ groups;
$R^2$ at each occurrence is independently F, Cl, Br, I, $OR^{21}$, $NR^{23}R^{24}$, $NO_2$, CN, $CF_3$, $C_1$-$C_6$
alkyl, C(=O)$R^{25}$, $CO_2R^{25}$, or C(=O)$NR^{23}R^{24}$;
$R^3$ is H or $C_1$-$C_6$ alkyl;
$R^4$ is H or $C_1$-$C_6$ alkyl;
X is O or $NOR^{10}$;
$R^{10}$ is H, $C_1$-$C_4$ alkyl, cycloalkyl, or arylalkyl;
A is selected from pyrrolidin-1-yl; piperidin-1-yl; morpholin-4-yl; piperazin-1-yl; thiomorpholin-4-yl; 1,3-dihydroisoindol-2-yl; 3,4-dihydro-2H-quinolin-1-yl; 3,4-dihydro-1H-quinolin-1-yl; 2,3,4,5-tetrahydro-benzo[b]azepin-1-yl; and benzoimadazol-1-yl;
wherein A can be optionally substituted with one to three $R^{20}$ groups;
$R^{20}$ at each occurrence is independently, F, CN, $CF_3$, $C_1$-$C_6$ alkyl optionally substituted with
$OR^{21}$, phenyl, 5 or 6 membered heteroaryl, (=O), C(=O) $R^{26}$, $CO_2R^{28}$, or $S(O)_2R^{25}$, wherein said phenyl group is optionally substituted with one to three $R^{30}$ groups;
$R^{21}$ at each occurrence is independently H, $C_1$-$C_6$ alkyl, aryl, or arylalkyl;
$R^{23}$ and $R^{24}$ at each occurrence are each independently selected from H, $C_1$-$C_6$ alkyl, and aryl,
or $R^{23}$ and $R^{24}$, together with the nitrogen atom to which they are attached, form a 3 to 7 membered heterocyclic ring optionally substituted with =O;

$R^{25}$ at each occurrence is independently $C_1$-$C_6$ alkyl, aryl, or arylalkyl;

$R^{26}$ at each occurrence is independently $NR^{23}R^{24}$, $CF_3$, $C_1$-$C_6$ alkyl, $C_3$-$C_7$ cycloalkyl, 3-7 membered heterocycloalkyl, aryl, 5-10 membered heteroaryl, or arylalkyl, wherein said alkyl, cycloalkyl, heterocycloalkyl, aryl, and heteroaryl groups are optionally substituted with one to three $R^{30}$ groups;

$R^{28}$ at each occurrence is independently $C_1$-$C_6$ alkyl, aryl, or arylalkyl, wherein said groups are optionally substituted with one to three $R^{30}$ groups;

$R^{30}$ at each occurrence is independently F, Cl, Br, I, $OR^{21}$, $NR^{23}R^{24}$, NHOH, $NO_2$, CN, $CF_3$, $C_1$-$C_6$ alkyl, aryl, or arylalkyl;

n is 0, 1, or 2;

or a stereoisomer or a pharmaceutically acceptable salt thereof.

In certain preferred embodiments, X is O. In other embodiments, X is $NOR^{10}$. In still other embodiments, $R^1$ is a pyrrolidin-1-yl or piperidin-1-yl group, wherein said group is optionally substituted with 1 to 3 $R^{20}$ groups. In preferred embodiments, A is pyrrolidin-1-yl, piperidin-1-yl, morpholin-4-yl, piperazin-1-yl, or thiomorpholin-4-yl wherein said groups are optionally substituted with 1 to 3 $R^{20}$ groups.

In some preferred embodiments of the present invention, $R^1$ is pyrrolidin-1-yl, piperidin-1-yl, piperazin-1-yl or morpholin-4-yl and A is pyrrolidin-1-yl, piperidin-1-yl, morpholin-4-yl, piperazin-1-yl, or thiomorpholin-4-yl, wherein said $R^1$ and A are each optionally substituted with 1 to 3 $R^{20}$ groups. In further preferred embodiments, $R^1$ is pyrrolidin-1-yl or piperidin-1-yl, and A is pyrrolidin-1-yl, piperidin-1-yl, morpholin-4-yl, or piperazin-1-yl, wherein said $R^1$ and A are each optionally substituted with 1 to 3 $R^{20}$ groups.

Particularly preferred compounds of the present invention are those selected from Examples 1 through 171, and the pharmaceutically acceptable salts thereof. In some embodiments, the compounds are selected from Examples 1 through 158, and the pharmaceutically acceptable salts thereof. In other embodiments, the compounds are selected from Examples 159 through 171, and the pharmaceutically acceptable salts thereof.

Also within the scope of the invention are pharmaceutical compositions comprising a compound of Formula I and one or more pharmaceutically acceptable excipients.

In certain preferred embodiments of the invention, there is provided a method for treating a disorder selected from the group consisting of narcolepsy, obstructive sleep apnea/hypopnea syndrome, shift work sleep disorder, wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders, inflammation, and myocardial infarction. comprising administering to a subject in need of such treatment a therapeutically effective amount of a compound of Formula I. In further preferred embodiments, the disorder is narcolepsy, obstructive sleep apnea/hypopnea syndrome, or shift work sleep disorder. In a particularly preferred embodiment, the disorder is attention deficit hyperactivity disorder.

Definitions

In the formulas described and claimed herein, it is intended that when any symbol appears more than once in a particular formula or substituent, its meaning in each instance is independent of the other.

The following terms and expressions have the indicated meanings.

As used herein, the term "about" refers to a range of values from ±10% of a specified value. For example, the phrase "about 50" includes ±10% of 50, or from 45 to 55. The phrase "from about 10 to 100" includes ±10% of 10 and ±10% of 100, or from 9 to 110.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, "substituted" refers to any one or more hydrogen atoms on the indicated atom being replaced with a selected group referred to herein as a "substituent", provided that the substituted atom's valency is not exceeded, and that the substitution results in a stable compound. A substituted group has 1 to 5, preferably 1 to 3, and more preferably 1 independently selected substituents. Preferred substituents include, but are not limited to F, Cl, Br, I, OH, OR, $NH_2$, $NR_2$, NHOH, $NO_2$, CN, $CF_3$, $CF_2CF_3$, $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, heterocyclyl, $C_6$-$C_{10}$ aryl, heteroaryl, arylalkyl, =O, C(=O)R, COOH, $CO_2R$, O—C(=O)R, C(=O)NRR', NRC(=O)R', $NRCO_2R'$, OC(=O)NRR', —NRC(=O)NRR', —NRC(=S)NRR', and —$SO_2NRR'$, wherein R and R' are each independently hydrogen, $C_1$-$C_6$ alkyl, or $C_6$-$C_{10}$ aryl.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Preferred alkyl groups contain 1 to 6 carbons. A designation such as "$C_1$-$C_6$ alkyl" refers to an alkyl radical containing from 1 to 6 carbon atoms.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" refers to a straight chain, or branched hydrocarbon chains of 2 to 8 carbon atoms having at least one carbon-carbon triple bond. A designation "$C_2$-$C_8$ alkynyl" refers to an alkynyl radical containing from 2 to 8 carbon atoms. Examples include ethynyl, propynyl, isopropynyl, 3,5-hexadiynyl, etc.

As used herein, the term "cycloalkyl" refers to a substituted or unsubstituted saturated or partially saturated mono- or bicyclic alkyl ring system containing 3 to 10 carbon atoms. Certain embodiments contain 3 to 7 carbon atoms, and other embodiments contain 5 or 6 carbon atoms. A designation such as "$C_3$-$C_7$ cycloalkyl" refers to a cycloalkyl radical containing from 3 to 7 ring carbon atoms. Examples of cycloalkyl groups include such groups as cyclopropyl, cyclobutyl, cyclopentyl, cyclohexyl, cycloheptyl, cyclooctyl, pinenyl, and adamantanyl.

As used herein, the term "aryl" refers to a substituted or unsubstituted, mono- or bicyclic hydrocarbon aromatic ring system having 6 to 12 ring carbon atoms. Examples include phenyl and naphthyl. Preferred aryl groups include unsubstituted or substituted phenyl and naphthyl groups.

As used herein, the terms "heterocycle", "heterocyclic" or "heterocyclyl" refer to a substituted or unsubstituted unsaturated, saturated or partially saturated carbocyclic group in which one or more ring carbon atoms are replaced by at least one hetero atom such as —O—, —N—, or —S—. Certain embodiments include 3 to 10 membered rings, and other embodiments include 3 to 7 membered rings. Further embodiments include 5 or 6 membered rings. The nitrogen and sulfur heteroatoms may be optionally oxidized, and the nitrogen may be optionally substituted in non-aromatic rings. Heterocycles are intended to include heteroaryl and heterocycloalkyl groups.

As used herein, the term "heteroaryl" refers to a substituted or unsubstituted aromatic group containing 5 to 10 ring carbon atoms in which one or more ring carbon atoms are replaced by at least one hetero atom such as —O—, —N—, or —S—. Certain embodiments include 5 or 6 membered rings. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl.

As used herein, the term "heterocycloalkyl" refers to a substituted or unsubstituted, saturated or partially saturated cycloalkyl group in which one or more ring carbon atoms are replaced by at least one hetero atom such as —O—, —N—, or —S—. Certain embodiments include 3 to 10 membered rings, and other embodiments include 3 to 7 membered rings. Certain preferred embodiments include 5 or 6 membered rings. Examples of heterocycloalkyl groups include pyrrolidinyl, pyrrolinyl, imidazolidinyl, imidazolinyl, pirazolidinyl, pirazolinyl, pyrazalinyl, piperidyl, piperazinyl, hexahydropyrimidinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl. Included within the definition of "heterocycloalkyl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl, etc.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-NH$_2$. The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, 2$^{nd}$ ed.; Worth Publishers: New York, 1975; 71-77. Non-naturally occurring amino acids also include α-amino acids wherein the side chains are replaced with synthetic derivatives. In certain embodiments, substituent groups for the compounds of the present invention include the residue of an amino acid after removal of the hydroxyl moiety of the carboxyl group thereof; i.e., groups of formula —C(=O)CH (side chain)-NH$_2$.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker New York, 1992.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981.

It is further recognized that functional groups present on intermediates used for the synthesis of the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

Synthesis

The compounds of the present invention may be prepared in a number of methods well known to those skilled in the art, or by methods described herein, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

The general routes to prepare the examples shown herein are shown in the General Schemes (GS) I-IV. The reagents and starting materials are commercially available, or readily synthesized by well-known techniques by one of ordinary skill in the arts. All substituents in the synthetic Schemes, unless otherwise indicated, are as previously defined.

General Scheme I

Synthesis of Ketone Examples "E"

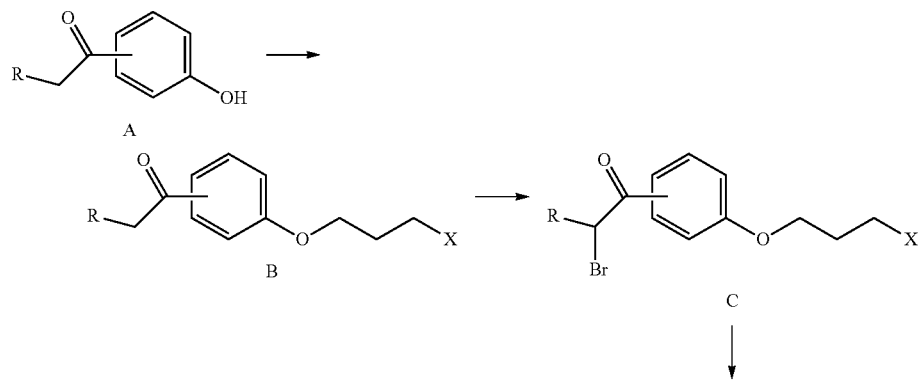

Scheme I

-continued

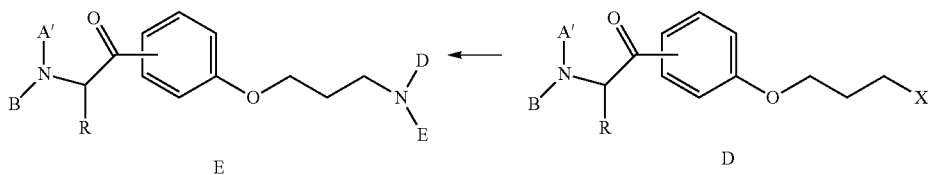

where
R is $R^4$, or a synthetic precursor thereto,
X is a synthetic precursor capable of reaction with amine

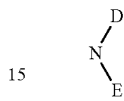

is $R^1$ or a synthetic precursor thereto.

In general, an alkyl-(hydroxy substituted)aryl ketone, (compound A) is reacted with a 1,3-dihalo-n-propane in presence of an inorganic base (e.g. potassium carbonate) in a polar solvent (acetone or acetonitrile) to generate halopropyloxyphenyl ketone, compound B. Compound B is then selectively brominated on the α-carbon atom adjacent to the carbonyl group with either elemental bromine ($Br_2$) or a metal bromide to yield the α-bromo ketone compound C. Compound C is then selectively reacted with various amines affording α-amino ketones D which may be subsequently reacted with additional amines to give final compounds E.

The application of above methodology has been exemplified in the synthesis of Example 1 (Scheme 1).

is A, where $R^3$ is H, or a synthetic precursor thereto, and

Scheme 1

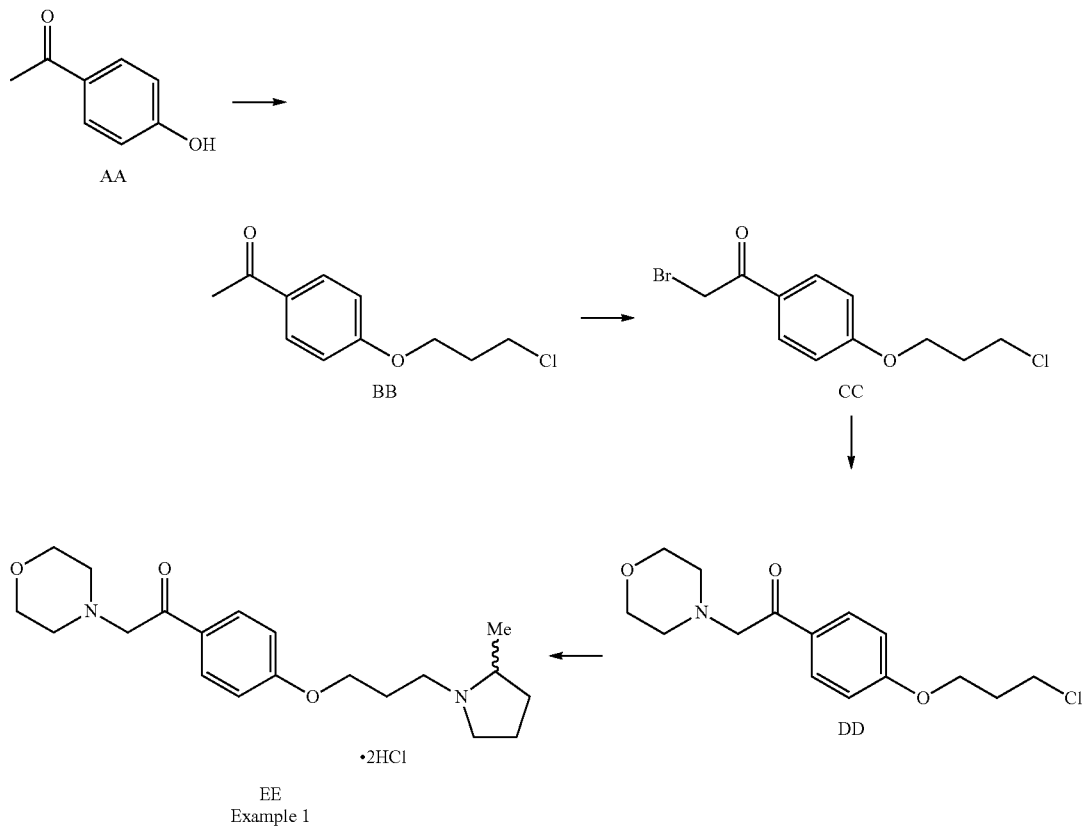

Example 1

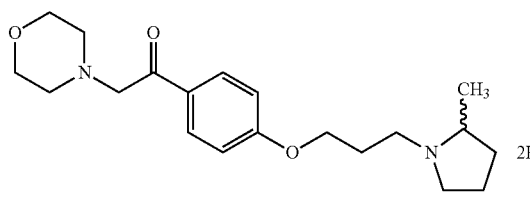

1-{4-[3-(2-Methyl-pyrrolidin-1-yl)-propoxy]-phenyl}
-2-morpholin-4-yl-ethanone dihydrochloride

Preparation of Compound BB

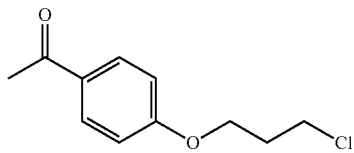

1-[4-(3-Chloro-propoxy)-phenyl]-ethanone

A mixture of commercially available 4-hydroxyacetophenone (compound AA, 27.00 g, 0.20 mol), 3-bromo-1-chloropropane (34.30 g, 0.22 mol), potassium carbonate (30.00 g, 0.24 mol), and acetone (400 mL) was refluxed overnight, cooled to room temperature, filtered, and the residue was then washed several times with acetone. The combined filtrate and washings were concentrated to give 40.00 g of crude compound BB that was taken directly to the next step without further purification.

Preparation of Compound CC

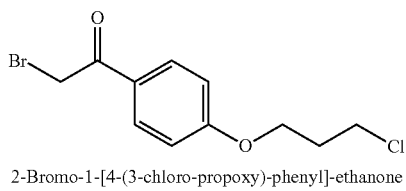 [SMILES: O=C(CBr)c1ccc(OCCCCl)cc1]

2-Bromo-1-[4-(3-chloro-propoxy)-phenyl]-ethanone

Bromine (2.67 mL, 0.052 mol) was slowly added to a stirred solution of compound BB (10.00 g, 0.05 mol) in diethyl ether (70 mL) maintained at 0° C. The cooling bath was removed and the reaction mixture was stirred overnight, filtered, diluted with additional diethyl ether, washed successively with 5% aq. $NaHSO_3$ solution, water, saturated aqueous $NaHCO_3$, water and brine. The organic layer was dried (magnesium sulfate) and concentrated to give a crude product that was purified by silica gel chromatography (eluting with 1:1 methylene chloride/hexane) to generate 10.5 g of compound CC (MS 292 (M+H)).

Preparation of Compound DD

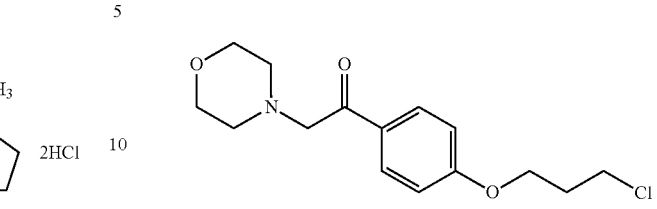

1-[4-(3-Chloro-propoxy)-phenyl]-2-morpholin-4-yl-ethanone

N,N-diisopropylethylamine (6.70 mL, 0.037 mol) was added to a stirred solution of compound CC (10.50 g, 0.04 mol) in absolute ethanol (150 mL) at room temperature followed by addition of morpholine (3.20 mL, 0.037 mol). The reaction mixture was stirred for an additional 1.5 h, concentrated and redissolved in methylene chloride. The organic layer was washed successively with water and brine, dried ($MgSO_4$), and concentrated to give 10.70 g of compound DD (MS 298 (M+H)) which was directly taken into next step without further purification.

Preparation of Compound EE

Example 1

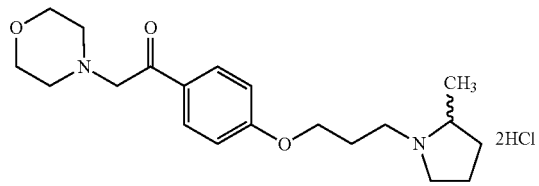

1-{4-[3-(2-Methyl-pyrrolidin-1-yl)-propoxy]-phenyl}-
2-morpholin-4-yl-ethanone dihydrochloride A mixture of compound DD (10.70 g, 0.04 mol), 2-methylpyrrolidine (7.34 mL, 0.07 mol), potassium carbonate (9.93 g, 0.07 mol) and sodium iodide (1.35 g, 0.01 mol) in 2-butanone (200 mL) was refluxed overnight, cooled and filtered. The residue was washed several times with small quantities of 2-butanone. The combined filtrate and washings were concentrated under vacuum to give a crude product that was subsequently purified on a silica gel column (eluting with 10% methanol in methylene chloride) to give a brown oil after evaporation of solvent. The oil was dissolved in methylene chloride, cooled to 0° C., treated with hydrogen chloride gas with stirring for an additional 5 minutes. The reaction mixture was then concentrated and treated with 20 ml of a 1:1 solution of ethyl acetate/methylene chloride and stirred at room temperature overnight. The precipitated solid was collected by filtration, washed with diethyl ether and dried under high vacuum to give compound EE, Example 1 (6.10 g) as the dihydrochloride salt; mp: 224° C. MS 347 (M+1, free base).

Scheme 1A depicts the synthesis of Example 21.

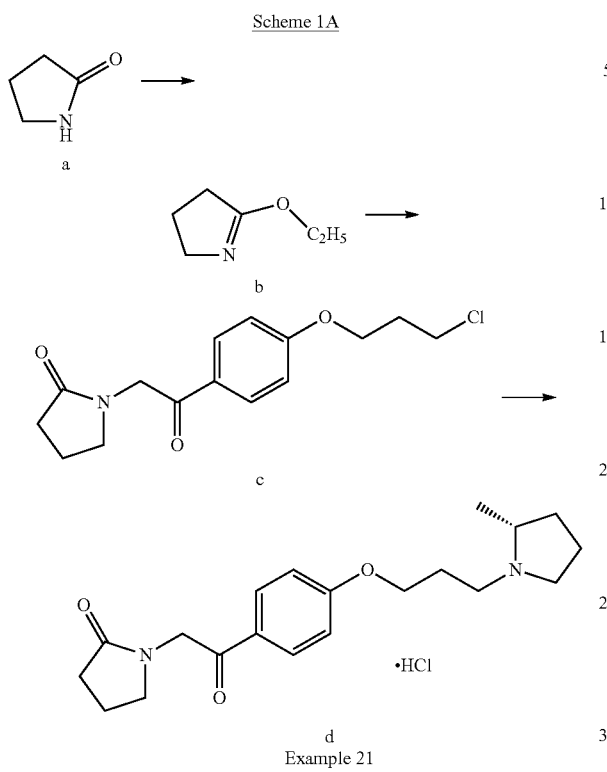

Example 21

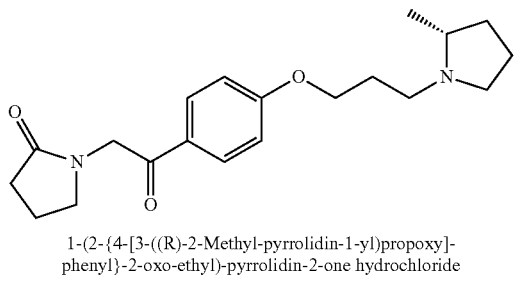 [SMILES: C[C@@H]1CCCN1CCCOc1ccc(C(=O)CN2CCCC2=O)cc1]

1-(2-{4-[3-((R)-2-Methyl-pyrrolidin-1-yl)propoxy]-phenyl}-2-oxo-ethyl)-pyrrolidin-2-one hydrochloride Preparation of Compound b

5-Ethoxy-3,4-dihydro-2H-pyrrole

A mixture of compound a (1.70 g, 20 mmol) and triethyloxonium tetrafluoroborate (8.00 g, 42 mmol) in dichloromethane (30 mL) was heated at reflux for 18 h, cooled, diluted with dichloromethane (50 mL) and washed successively with cold saturated aqueous $K_2CO_3$ (50 mL), brine, dried ($K_2CO_3$) and then concentrated to give compound b (1.6 g, colorless liquid) which was directly taken into next step without purification.

Preparation of Compound c

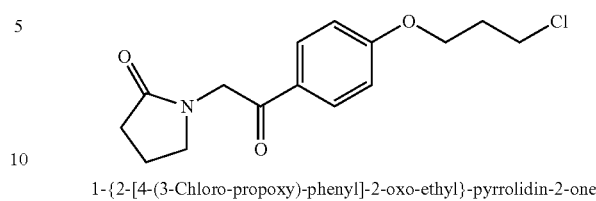

1-{2-[4-(3-Chloro-propoxy)-phenyl]-2-oxo-ethyl}-pyrrolidin-2-one

A mixture of compound b (1.60 g, 14.2 mmol) and compound CC from Scheme 1 (4.00 g, 13.70 mmol) in DMF (80 mL) was stirred at 50° C. for 18 h, evaporated to dryness and the crude residue purified by flash chromatography (silica gel; dichloromethane/methanol, 30:1) affording compound c (3.75 g) as a brown oil; MS m/z 318 (M+Na).

Preparation of Compound d

Example 21

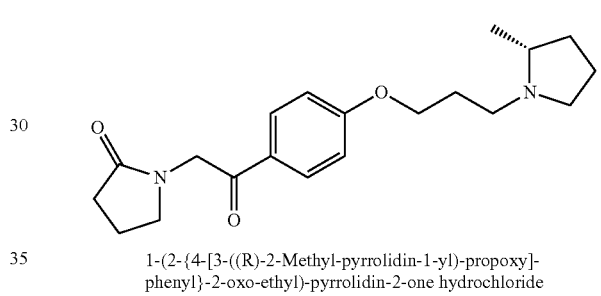

1-(2-{4-[3-((R)-2-Methyl-pyrrolidin-1-yl)-propoxy]-phenyl}-2-oxo-ethyl)-pyrrolidin-2-one hydrochloride A mixture of compound c (3.75 g, 12.7 mmol), 2-(R)-methylpyrrolidine tartrate (5.23 g, 22.30 mmol), diisopropylethylamine (6.00 g, 46.40 mmol), $K_2CO_3$ (6.00 g, 43.50 mmol) and sodium iodide (0.50 g) in 2-butanone (200 mL) was heated at reflux for 48 h, cooled, filtered and evaporated to dryness to give a crude residue that was then purified by column chromatography (silica gel; dichloromethane/methanol, 10:1) to produce 1.95 g of an oil. The oil was next dissolved in ethyl acetate (30 mL) and treated with 4 N HCl (in ethyl acetate) to give 1.86 g of compound d as the hydrochloride salt; MS m/z 345 (M+H).

In a variation of the synthetic scheme above, some of the final compounds were also prepared via an alternate general method (General Scheme II) depicted below.

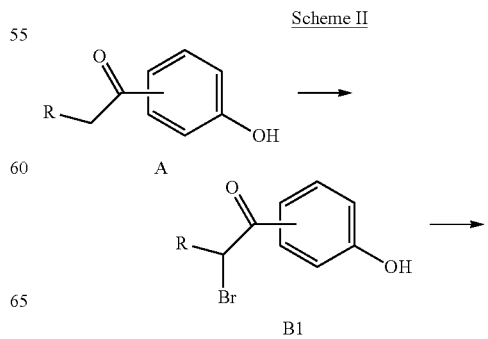

21
-continued

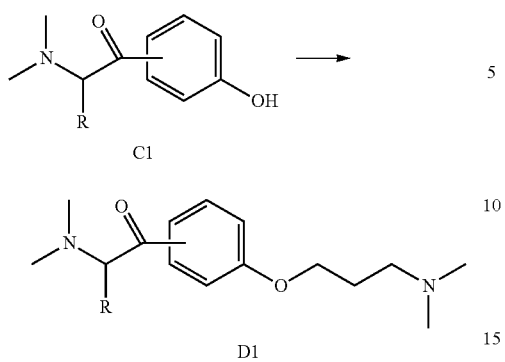

where
R is R⁴, or a synthetic precursor thereto.

In General Scheme II, compound A underwent bromination in the first step to generate α-bromoketone compound B1 that was then reacted with an amine to generate α-aminoketone compound C1. Compound C1 was in turn subjected to a Mitsunobu coupling reaction with an appropriate alcohol containing a terminal amine functionality to generate final compound D1. The application of the above methodology has been exemplified in the synthesis of the following compounds (Scheme 2).

22
Example 103

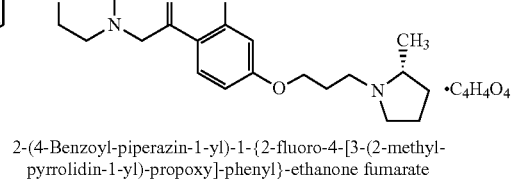

2-(4-Benzoyl-piperazin-1-yl)-1-{2-fluoro-4-[3-(2-methyl-pyrrolidin-1-yl)-propoxy]-phenyl}-ethanone fumarate Preparation of Compound BB1

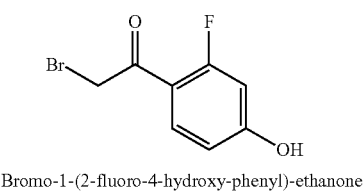

2-Bromo-1-(2-fluoro-4-hydroxy-phenyl)-ethanone

Scheme 2

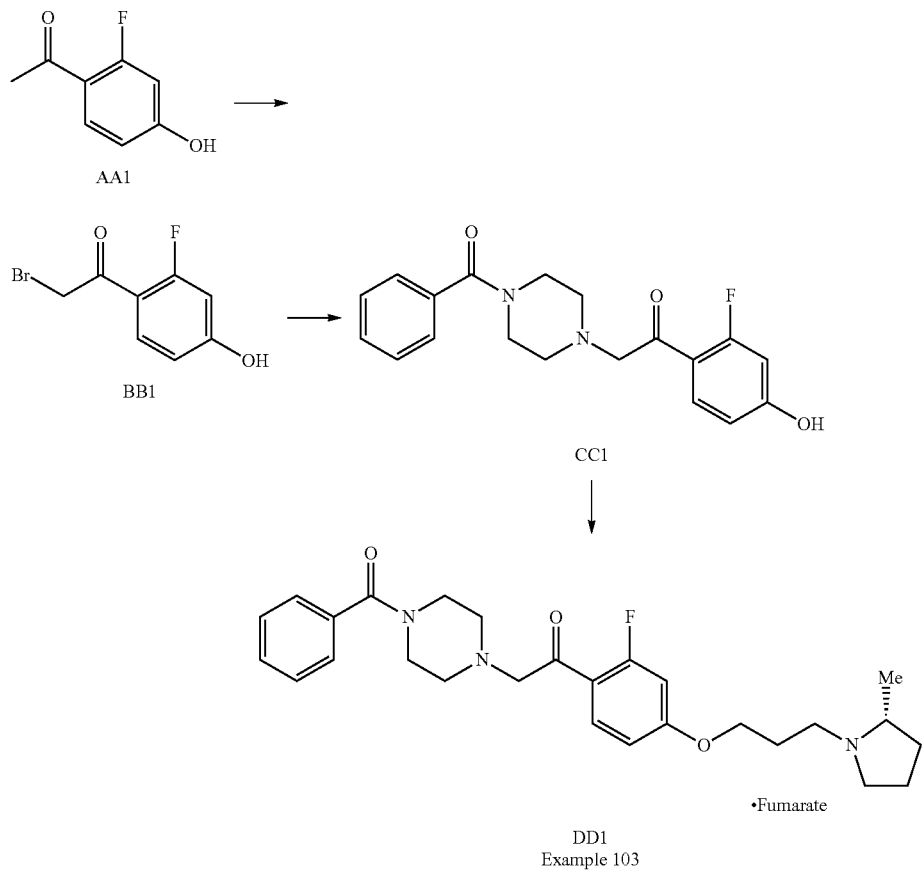

Commercially available 4-hydroxyacetophenone derivative AA1 (10.00 g, 65 mmol) was slowly added over 15 min to a refluxing suspension of $CuBr_2$ (29.1 g, 130 mmol) in a mixture of EtOAc and $CHCl_3$ (1:1; 140 mL). The reaction mixture was refluxed under nitrogen with vigorous stirring for additional 6 h, cooled to room temperature and filtered through a pad of Celite topped by a layer of Darco/Clarion. The filtrate was concentrated affording crude compound BB1 (14.3 g) that was directly taken into next step without further purification.

Preparation of Compound CC1

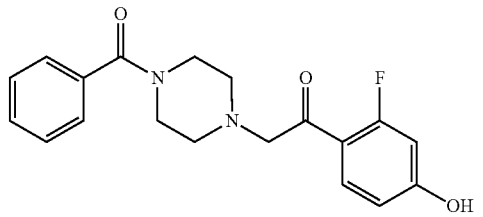

2-(4-Benzoyl-piperazin-1-yl)-1-(2-fluoro-4-hydroxy-phenyl)-ethanone

To a solution of bromoacetophenone derivative BB1 (3.06 g, 13 mmol) in absolute EtOH (50 mL) was added 1-benzoylpiperazine (2.50 g, 13 mmol) followed by diisopropylethylamine (2.30 mL, 13 mmol). The dark red reaction mixture was heated to 50° C. for 10 min, stirred at room temperature overnight and concentrated. The residue was dissolved in EtOAc (50 mL), washed with water, dilute acetic acid, water and brine; during the process, the crude product crystallized. It was collected by filtration and dried to afford compound CC1 (1.58 g) as a tan solid) that was directly used in the next step without any further purification; MS 343 [M+H].

Preparation of Compound DD1

Example 103

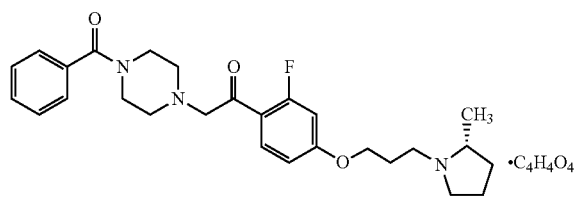

2-(4-Benzoyl-piperazin-1-yl)-1-{2-fluoro-4-[3-(2-methyl-pyrrolidin-1yl)-propoxy]-phenyl}-ethanone fumarate To a suspension of compound CC1 (1.51 g, 4.40 mmol), triphenylphosphine (2.24 g, 8.80 mmol), and 3-((R)-2-methylpyrrolidine)propan-1-ol (1.26 g, 8.80 mmol, prepared from corresponding (R)-2-methylpyrrolidine hydrochloride and 3-bromo-1-propanol) in anhydrous THF (20 mL) and anhydrous DMF (5 mL) at room temperature was added diethylazodicarboxylate (1.35 mL, 8.80 mmol) over 5 min. The brown solution was stirred at room temperature under nitrogen for 20 h, diluted with EtOAc (50 mL), and extracted into a citric acid solution (50 mL). The acidic solution was cooled (ice bath), basified with 50% aq. NaOH solution to pH~11 and extracted with EtOAc (100 mL). The organic layer was washed with water, dried ($NaSO_4$) and concentrated to afford crude product that was purified by chromatography (silica gel; gradient of 5% 4:1:0.2 $CH_2Cl_2$/MeOH/$NH_4OH$ in $CH_2Cl_2$ to 50% 4:1:0.2 $CH_2Cl_2$/MeOH/$NH_4OH$ in $CH_2Cl_2$) to yield 0.57 g (28%) of the DD1 as the free base.

The free base was then treated with fumaric acid to generate Example 103 fumaric acid salt; mp 98-101° C. MS: m/z 468 [M+H free base].

Additional examples prepared using the synthetic methodology described above are depicted in Scheme 3, depicting the preparation of Example 45 as illustrative.

Scheme 3

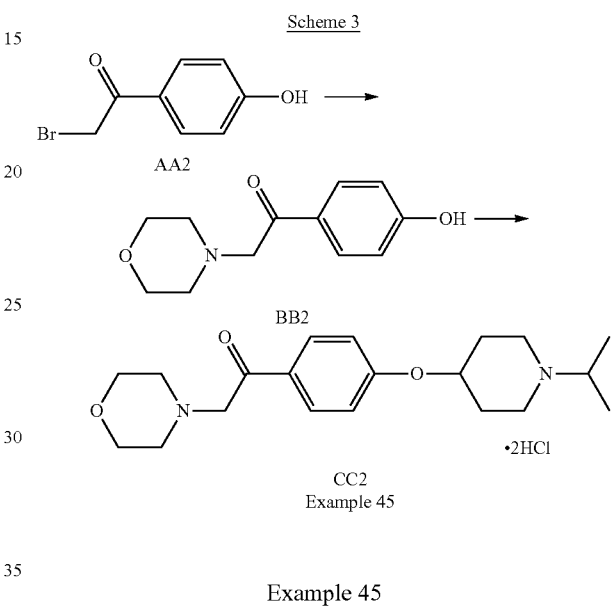

Example 45

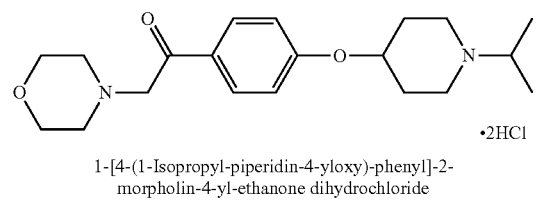

1-[4-(1-Isopropyl-piperidin-4-yloxy)-phenyl]-2-morpholin-4-yl-ethanone dihydrochloride Preparation of Compound BB2

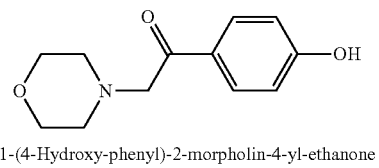 [SMILES: O=C(CN1CCOCC1)c1ccc(O)cc1]

1-(4-Hydroxy-phenyl)-2-morpholin-4-yl-ethanone

A mixture of commercially available bromoacetophenone derivative AA2 (0.50 g, 2.30 mmol) and morpholine (0.40 g, 0.47 mmol) in $CH_3CN$ was stirred at room temperature for 1 h. The mixture was concentrated at reduced pressure and triturated with water to give a white solid. The product was collected, dried and recrystallized from EtOH to give 0.49 g of compound BB2, mp 212-213° C.; MS m/z=221 (M+H).

Preparation of Compound CC2

Example 45

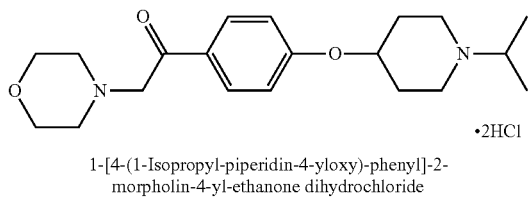 [SMILES: CC(C)N1CCC(Oc2ccc(C(=O)CN3CCOCC3)cc2)CC1]

1-[4-(1-Isopropyl-piperidin-4-yloxy)-phenyl]-2-morpholin-4-yl-ethanone dihydrochloride Diethylazodicarboxylate (0.71 g, 3.50 mmol) was added dropwise to a cooled (ice bath) solution of compound BB2 (0.50 g, 2.3 mmol), 4-hydroxy-N-isopropyl-piperidine (0.36 g, 2.5 mmol) and triphenylphosphine (0.91 g, 3.5 mmol) in dry THF (10 mL). The ice bath was removed and the reaction mixture was stirred for an additional 4 h at room temperature, concentrated and purified by ISCO silica gel chromatography (95:5:1; methylene chloride:methanol: isopropylamine) to give the free base as an oil that was then converted to the dihydrochloride acid salt followed by recrystallization from methanol-ether to give 0.11 g of Example 45 as a white solid; mp 296-298° C., MS m/z=347 (M+1).

Example 53

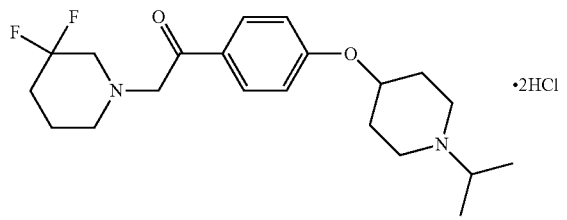

2-(3,3-Difluoro-piperidin-1-yl)-1-[4-(isopropyl-piperidin-4-yloxy)-phenyl]-ethanone dihydrochloride Example 53 was prepared following the same method as utilized to prepare Example 45, substituting 3,3-difluoropiperidine for morpholine in the initial reaction with 4-hydroxy-α-bromoacetophenone. Coupling of the intermediate phenol with 4-hydroxy-N-isopropylpiperidine afforded the final compound, Example 53; mp 160-165° C. (MeOH-ether); MS m/z=381 (M+H).

Example 87

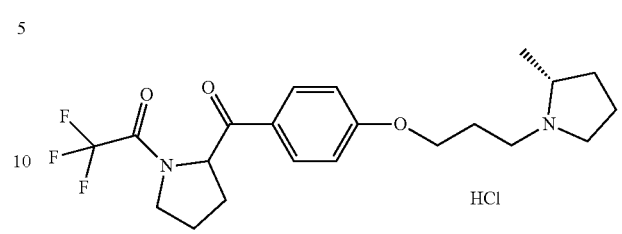

2,2,2-Trifluoro-1-(2-{4-[3-((R)-2-methyl-pyrrolidin-1-yl)-propoxy]-benzoyl}-pyrrolidin-1-yl)-ethanone hydrochloride

Preparation of Compound BB3

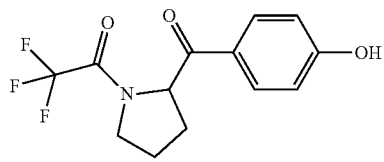

2,2,2-Trifluoro-1-[2-(4-hydroxy-benzoyl)-pyrrolidin-1-yl]-ethanone

Example 87 was prepared according to Scheme 4 described above. BBr₃ (1 M solution in dichloromethane, 6.60 mL) was added dropwise to a cooled (ice bath) solution of compound AA3 (0.40 g, 1.3 mmol, (prepared according to the literature reference: *J. Chem. Soc. Perkin Trans.*, 1987, 1465 included herein in its entirety)) in dichloromethane (5 mL). The cooling bath was removed and the solution was stirred at room temperature for 2 h. The mixture was again cooled (ice-bath) and quenched with dropwise addition of saturated NH₄Cl solution (6 mL). The solvent was removed at reduced pressure and excess water added. The solid that separated was collected and dried to give compound BB3 that was taken directly into the next step; MS m/z=288 (M+1).

Scheme 4

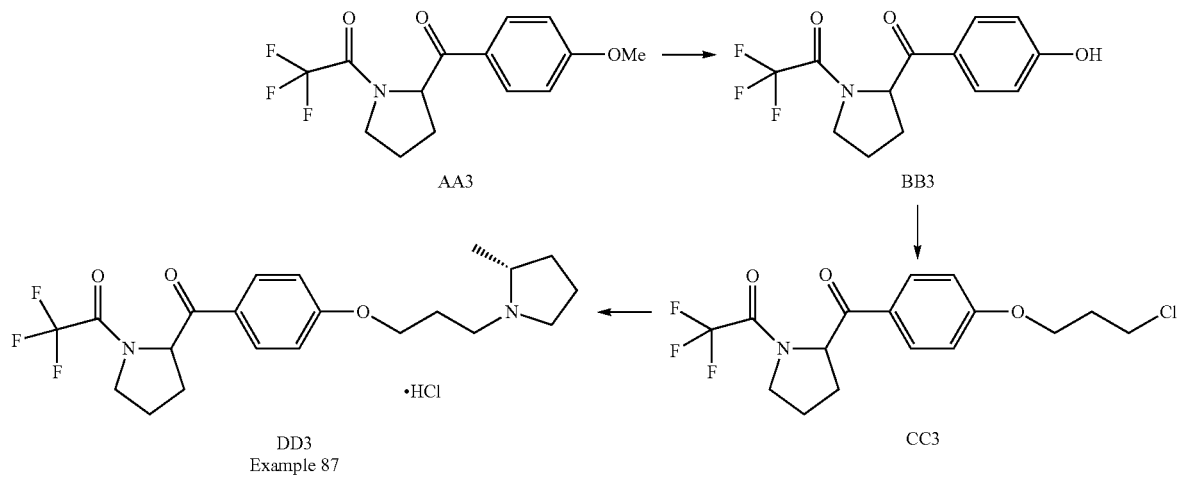

AA3 → BB3

DD3
Example 87 ← CC3

Preparation of Compound CC3

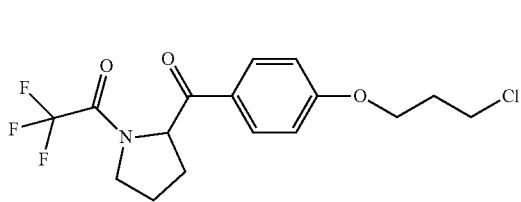

1-{2-[4-(3-Chloro-propoxy)-benzoyl]-
pyrrolidin-1-yl}-2,2,2-trifluoro-ethanone

A mixture of compound BB3 (0.33 g, 1.20 mmol), $K_2CO_3$ (0.32 g, 2.30 mmol) and 1-bromo-3-chloropropane (0.36 g, 2.30 mmol) in acetone (25 mL) was stirred at reflux for 12 h, cooled and filtered. The filtrate was concentrated under reduced pressure and the resulting oil was dissolved in ether (50 mL) and washed successively with 1 N $Na_2CO_3$, water and NaCl solution, and then dried ($MgSO_4$). The solvent was removed under vacuum to give compound CC3 as an oil (425 mg) that was directly used in the next step. MS m/z=364 (M+1).

Preparation of Compound DD3

Example 87

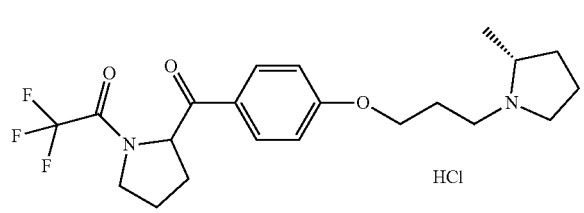

2,2,2-Trifluoro-1-(2-{4-[3-((R)-2-methyl-pyrrolidin-1-yl)-
propoxy]-benzoyl}-pyrrolidin-1-yl)-ethanone hydrochloride A mixture of compound CC3 (0.42 g, 1.20 mmol), $K_2CO_3$ (0.32 g, 2.30 mmol), NaI (0.171 g, 1.20 mmol) and R-2-methylpyrrolidine (0.21 g, 1.7 mmol) in $CH_3CN$ (50 mL) was heated at reflux for 30 h, cooled to room temperature, filtered and concentrated to give an oil that was treated with 1N HCl in ether to give the target compound; mp 98-101° C. (acetone-ether), MS m/z=413 (M+1).

For some target compounds bearing alkyl substitution alpha to the carbonyl group, additional steps were required to introduce such functionality as shown in Scheme 5.

Scheme 5

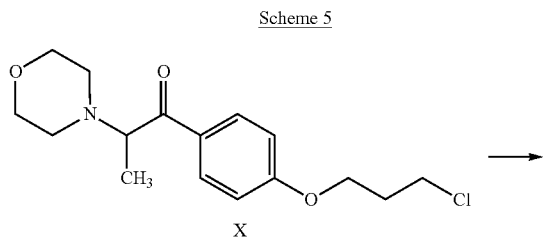

Example 54

2-Methyl-1-{4-[3-((R)-2-methyl-pyrrolidin-1-yl)-
propoxy]-phenyl}-2-morpholin-4-yl-propan-1-one fumarate

Preparation of Compound Y

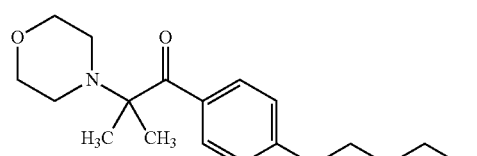

1-[4-(3-Chloro-propoxy)-phenyl]-2-methyl-2-
morpholin-4-yl-propan-1-one

2M LDA in hexane (3.80 mL, 7.70 mmol) was slowly added to a solution of compound X (2.00 g, 6.40 mmol, prepared according to Scheme I) in 25 mL of anhydrous THF at −78° C. under $N_2$. The reaction mixture was stirred for 5 min followed by the addition of MeI (0.80 mL, 12.80 mmol) to the flask. The reaction mixture was allowed to warm to room temperature, quenched with dilute $NH_4Cl$ solution (100 mL) and extracted with EtOAc (100 ml). The organic phase was dried ($Na_2SO_4$) and concentrated in vacuo to give the crude product which was purified by gradient flash chromatography (silica gel; 4:1 hexane/EtOAc to 2:1 hexane/EtOAc) affording 0.85 g of compound Y as a viscous, pale yellow oil; MS 326 (M+H).

Preparation of Compound Z

Example 54

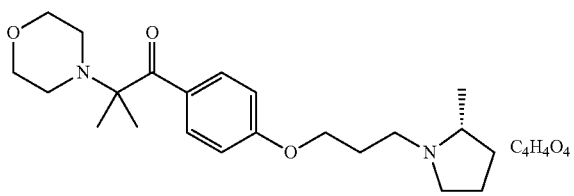

2-Methyl-1-{4-[3-((R)-2-methyl-pyrrolidin-1-yl)-propoxy]-phenyl}-2-morpholin-4-yl-propan-1-one fumarate A suspension of compound Y (0.24 g, 0.7 mmol), (R)-2-methylpyrrolidine hydrochloride (0.107 g, 0.9 mmol), NaI (0.06 g, 0.4 mmol), and diisopropylethylamine (0.52 g, 1.4 mmol) in 2-butanone (2 mL) was subjected to microwave irradiation for 20 min (180° C.). After cooling, an additional amount of (R)-2-methylpyrrolidine hydrochloride (0.107 g, 0.9 mmol) and diisopropylethylamine (0.52 g, 1.4 mmol) were added, and the reaction mixture was resubjected to microwave irradiation for another 20 min (180° C.). The crude reaction mixture was then adsorbed onto silica gel (5 g), and the solvents were removed under reduced pressure. Flash chromatography of the above material (silica gel; 3% MeOH in CH$_2$Cl$_2$) afforded Example 54 (0.24 g) as a colorless oil. The free base was then converted to the fumaric acid salt to give 0.113 g of product as off-white foam; mp 45-50° C. MS m/z 375 [M+H free-base].

Piperazine derivatives as utilized for the preparation of Example 103 in Scheme 2 that are not commercially available, were prepared according to General Scheme III (shown below). Thus, a monoprotected piperazine compound AAA was either acylated by an acyl halide or sulfonated by a sulfonyl halide to generate an intermediate compound BBB that was deprotected to generate the desired reagent CCC.

Scheme III

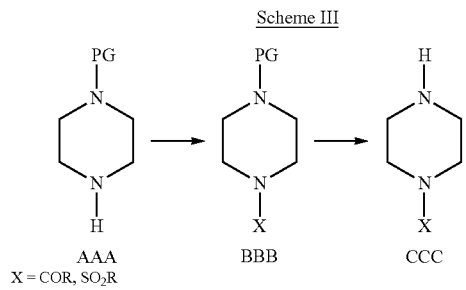

X = COR, SO$_2$R where
PG is a Protecting Group, and
R is halo.

An application of the above-mentioned methodology has been exemplified in Scheme 6 that was utilized to generate the piperazine CCCC.

Scheme 6

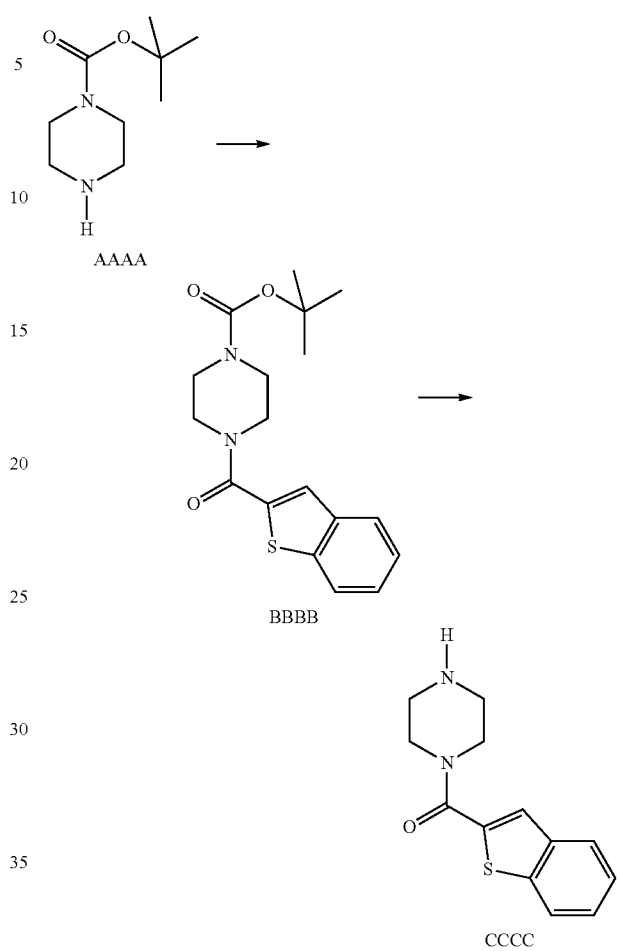

Preparation of Compound CCCC

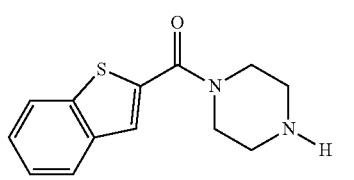

Benzo[b]thiophen-2-yl-piperazin-1-yl-methanone

To a stirring solution of commercially available t-Boc-piperazine (compound AAAA, 1 g, 5.37 mmol) in CH$_2$Cl$_2$ (10 mL) at room temperature was sequentially added benzo[b]thiophene-carbonyl chloride (1 g, 5.37 mmol) and triethylamine (2.2 mL, 16.1 mmol). The reaction mixture was stirred for an additional 1 h and quenched with cold water. The organic layer was washed with aq. NaCl, dried (Na$_2$SO$_4$), and concentrated to give 1.6 g of compound BBBB that was redissolved in CHCl$_3$ (15 mL) and treated with conc. HCl (1.9 mL). The reaction mixture was then refluxed for 5 h, cooled and basified. The basic aqueous layer was extracted with methylene chloride and the organic layer was washed with H$_2$O and brine, dried (Na$_2$SO$_4$,) and concentrated to generate 0.80 g of compound CCCC that was subsequently utilized in the preparation of Example 124.

The following ketone examples were prepared using the procedures described above.

| Example | Structure | mp (° C.) | MS m/z | Scheme |
|---|---|---|---|---|
| 1 | 1-{4-[3-(2-Methyl-pyrrolidin-1-yl)-propoxy]-phenyl}-2-morpholin-4-yl-ethanone | 224 | 347 (M + H) | 1 |
| 2 | 2-Piperidin-1-yl-1-[4-(3-piperidin-1-yl-propoxy)-phenyl]-ethanone | NA | 345 (M + H) | GS I |
| 3 | 2-Piperidin-1-yl-1-[4-(3-pyrrolidin-1-yl-propoxy)-phenyl]-ethanone | NA | 331 (M + H) | GSI |
| 4 | 2-(3,4-Dihydro-1H-isoquinolin-2-yl)-1-[4-(3-piperidin-1-yl-propoxy)-phenyl]-ethanone | NA | 393 (M + H) | GS I |
| 5 | 2-(3,4-Dihydro-1H-isoquinolin-2-yl)-1-[4-(3-pyrrolidin-1-yl-propoxy)-phenyl]-ethanone | NA | 379 (M + H) | GS I |

-continued

| Example | Structure | mp (° C.) | MS m/z | Scheme |
|---|---|---|---|---|
| 6 | 2-(1,3-Dihydro-isoindol-2-yl)-1-[4-(3-piperidin-1-yl-propoxy)-phenyl]-ethanone | NA | 379 (M + H) | GS I |
| 7 | 2-(3,4-Dihydro-2H-quinolin-1-yl)-1-[4-(3-piperidin-1-yl-propoxy)-phenyl]-ethanone | NA | 393 (M + H) | GS I |
| 8 | 1-{4-[3-((R)-2-Methyl-pyrrolidin-1-yl)-propoxy]-phenyl}-2-piperidin-1-yl-ethanone | NA | 345 (M + H) 2M + Na = 711 | GS I |
| 9 | 2-(3,4-Dihydro-1H-isoquinolin-2-yl)-1-{4-[3-((R)-2-methyl-pyrrolidin-1-yl)-propoxy]-phenyl}-ethanone | NA | 393 (M + H) 2M + Na = 807 | GS I |
| 10 | 1-{4-[3-(2-Methyl-piperidin-1-yl)-propoxy]-phenyl}-2-piperidin-1-yl-ethanone | NA | 359 (M + H) | GS I |

-continued

| Example | Structure | mp (° C.) | MS m/z | Scheme |
|---|---|---|---|---|
| 11 | 1-{4-[3-(2,6-Dimethyl-piperidin-1-yl)-propoxy]-phenyl}-2-piperidin-1-yl-ethanone | NA | 373 (M + H) | GS I |
| 12 | 1-{4-[3-((2R,5R)-2,5-Dimethyl-pyrrolidin-1-yl)-propoxy]-phenyl}-2-piperidin-1-yl-ethanone | NA | 359 (M + H) | GS I |
| 13 | 1-{4-[3-((S)-2-Methyl-pyrrolidin-1-yl)-propoxy]-phenyl}-2-piperidin-1-yl-ethanone | NA | 345 (M + H) | GS I |
| 14 | 2-Piperidin-1-yl-1-[4-(3-pyrrolidin-1-yl-propoxy)-phenyl]-propan-1-one | NA | 345 (M + H) | GS I |
| 15 | 2-Morpholin-4-yl-1-[4-(3-pyrrolidin-1-yl-propoxy)-phenyl]-ethanone | NA | 333 (M + H) | GS I |

| Example | Structure | mp (° C.) | MS m/z | Scheme |
|---|---|---|---|---|
| 16 | 1-{4-[3-(4-Isopropyl-piperazin-1-yl)-propoxy]-phenyl}-2-piperidin-1-yl-ethanone | NA | 388 (M + H) | GS I |
| 17 | 2-(4-Phenyl-piperazin-1-yl)-1-[4-(3-pyrrolidin-1-yl-propoxy)-phenyl]-ethanone | NA | 408 (M + H) | GS I |
| 18 | 1-{4-[3-(2-Methyl-pyrrolidin-1-yl)-propoxy]-phenyl}-2-(4-phenyl-piperazin-1-yl)-ethanone | NA | 422 (M + H) | GS I |
| 19 | 2-Piperidin-1-yl-1-[4-(3-piperidin-1-yl-propoxy)-phenyl]-propan-1-one | >240 | 359 (M + H) | GS I |
| 20 | 1-{4-[3-((S)-2-Methyl-pyrrolidin-1-yl)-propoxy]-phenyl}-2-piperidin-1-yl-propan-1-one | >230 | 359 (M + H) | GS I |

-continued

| Example | Structure | mp (° C.) | MS m/z | Scheme |
|---|---|---|---|---|
| 21 | 1-(2-{4-[3-((R)-2-Methyl-pyrrolidin-1-yl)-propoxy]-phenyl}-2-oxo-ethyl)-pyrrolidin-2-one | NA | 345 (M + H) | 1A |
| 22 | 1-(2-{4-[3-((R)-2-Methyl-pyrrolidin-1-yl)-propoxy]-phenyl}-2-oxo-ethyl)-piperidin-2-one | NA | 359 (M + H) | GS I |
| 23 | 2-Pyrrolidin-1-yl-1-[4-(3-pyrrolidin-1-yl-propoxy)-phenyl]-propan-1-one | NA | 331 (M + H) 2M + Na = 683 | GS I |
| 24 | 1-{4-[3-(2-Methyl-pyrrolidin-1-yl)-propoxy]-phenyl}-2-pyrrolidin-1-yl-propan-1-one | NA | 345 (M + H) | GS I |
| 25 | 2-Morpholin-4-yl-1-[4-(3-pyrrolidin-1-yl-propoxy)-phenyl]-propan-1-one | NA | 347 (M + H) 2M + Na = 714 | GS I |

| Example | Structure | mp (° C.) | MS m/z | Scheme |
|---|---|---|---|---|
| 26 | 2-Morpholin-4-yl-1-[4-(3-piperidin-1-yl-propoxy)-phenyl]-propan-1-one | NA | 361 (M + H) 2M + Na = 743 | GS I |
| 27 | 1-{4-[3-(2-Methyl-pyrrolidin-1-yl)-propoxy]-phenyl}-2-morpholin-4-yl-propan-1-one | NA | 361 (M + H) 2M + Na = 743 | GS I |
| 28 | 1-{4-[3-(2-Methyl-pyrrolidin-1-yl)-propoxy]-phenyl}-2-(4-phenyl-piperazin-1-yl)-propan-1-one | NA | 436 (M + H) | GS I |
| 29 | 1-{4-[3-((R)-2-Methyl-pyrrolidin-1-yl)-propoxy]-phenyl}-2-(2-phenyl-morpholin-4-yl)-ethanone | NA | 423 (M + H) | GS I |
| 30 | 2-(4-Phenyl-piperazin-1-yl)-1-[4-(3-pyrrolidin-1-yl-propoxy)-phenyl]-propan-1-one | NA | 422 (M + H) 2 M + Na = 865 | GS I |

-continued

| Example | Structure | mp (° C.) | MS m/z | Scheme |
|---|---|---|---|---|
| 31 | 2-(4-Phenyl-piperazin-1-yl)-1-[4-(3-piperidin-1yl-propoxy)-phenyl]-propan-1-one | NA | 436 (M + H) 2M + Na = 893 | GS I |
| 32 | 2-(4-Acetyl-piperazin-1-yl)-1-[4-(3-piperidin-1-yl-propoxy)-phenyl]-propan-1-one | NA | 402 (M + H) | GS I |
| 33 | 2-(4-Acetyl-piperazin-1-yl)-1-{4-[3-(2-methyl-pyrrolidin-1-yl)-propoxy]-phenyl}-propan-1-one | NA | 402 (M + H) | GS I |
| 34 | 1-[4-(3-Piperidin-1-yl-propoxy)-phenyl]-2-thiomorpholin-4-yl-propan-1-one | NA | 377 (M + H) | GS I |

-continued

| Example | Structure | mp (° C.) | MS m/z | Scheme |
|---------|-----------|-----------|--------|--------|
| 35 | 1-{4-[3-(2-Methyl-pyrrolidin-1-yl)-propoxy]-phenyl}-2-thiomorpholin-4-yl-propan-1-one | NA | 377 (M + H) | GS I |
| 36 | 1-(1-Methyl-2-{4-[3-((S)-2-methyl-pyrrolidin-1-yl)-propoxy]-phenyl}-2-oxo-ethyl)-piperidin-2-one | NA | 373 (M + H) 2M + Na = 767 | GS I |
| 37 | 1-{4-[3-((R)-2-Methyl-pyrrolidin-1-yl)-propoxy]-phenyl}-2-morpholin-4-yl-propan-1-one | 231 | 361 (M + H) | GS I |
| 38 | 2-((2R,6S)-2,6-Dimethyl-morpholin-4-yl)-1-{4-[3-((R)-2-methyl-pyrrolidin-1-yl)-propoxy]-phenyl}-ethanone | NA | 375 (M + H) | GS I |
| 39 | 1-{4-[3-((R)-2-Methyl-pyrrolidin-1-yl)-propoxy]-phenyl}-2-((S)-2-phenyl-morpholin-4-yl)-ethanone | NA | 423 (M + H) | GS I |

-continued

| Example | Structure | mp (° C.) | MS m/z | Scheme |
|---|---|---|---|---|
| 40 | 1-{4-[3-((R)-2-Methyl-pyrrolidin-1-yl)-propoxy]-phenyl}-2-((R)-2-phenyl-morpholin-4-yl)-ethanone | NA | 423 (M + H) | GS I |
| 41 | 1-{4-[3-((R)-2-Methyl-pyrrolidin-1-yl)-propoxy]-phenyl}-2-morpholin-4-yl-ethanone | 226 | 347 (M + H) | GS I |
| 42 | 1-{4-[3-((S)-2-Methyl-pyrrolidin-1-yl)-propoxy]-phenyl}-2-morpholin-4-yl-ethanone | 107 (dec) | 347 (M + H) | GS I |
| 43 | 1-(2-{4-[3-((R)-2-Methyl-pyrrolidin-1-yl)-propoxy]-phenyl}-2-oxo-ethyl)-piperidine-4-carbonitrile | 138-141 | 370 (M + H) | GS I |
| 44 | 2-(4,4-Difluoro-piperidin-1-yl)-1-{4-[3-((R)-2-methyl-pyrrolidin-1-yl)-propoxy]-phenyl}-ethanone | 127-140 | 381 (M + H) | GS I |

-continued

| Example | Structure | mp (° C.) | MS m/z | Scheme |
|---|---|---|---|---|
| 45 | 1-[4-(1-Isopropyl-piperidin-4-yloxy)-phenyl]-2-morpholin-4-yl-ethanone | 296-298 | 347 (M + H) | 3 |
| 46 | 1-{4-[3-(1,3-Dihydro-isoindol-2-yl)-propoxy]-phenyl}-2-morpholin-4-yl-ethanone | 139.0-139.5 | 381 (M + H) | GS I |
| 47 | 1-{4-[3-((R)-2-Methyl-pyrrolidin-1-yl)-propoxy]-phenyl}-2-(4-trifluoro-methyl-piperidin-1-yl)-ethanone | 122-128 | 413 (M + H) | GS I |
| 48 | 2-Morpholin-4-yl-1-[4-(3-morpholin-4-yl-propoxy)-phenyl]-propan-1-one | 258 | 363 (M + H) | GS I |
| 49 | 1-{4-[3-(4-Acetyl-piperazin-1-yl)-propoxy]-phenyl}-2-morpholin-4-yl-ethanone | 247 | 390 (M + H) | GS I |

-continued

| Example | Structure | mp (° C.) | MS m/z | Scheme |
|---|---|---|---|---|
| 50 | 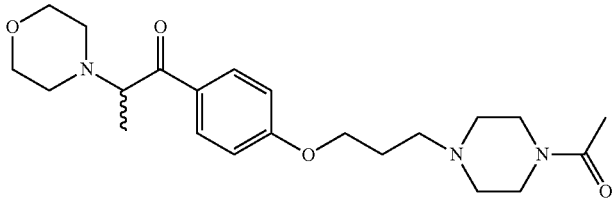  1-{4-[3-(4-Acetyl-piperazin-1-yl)-propoxy]-phenyl}-2-morpholin-4-yl-propan-1-one | 240 | 404 (M + H) | GS I |
| 51 | 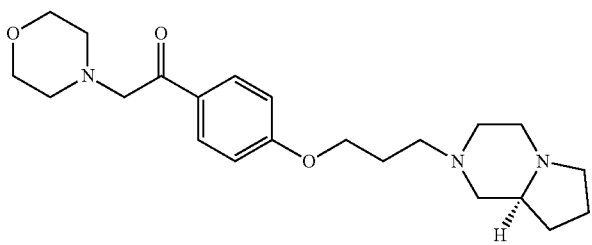  1-{4-[(S)-3-(Hexahydro-pyrrolo[1,2-a]pyrazin-2-yl)-propoxy]-phenyl}-2-morpholin-4-yl-ethanone | 238 | 388 (M + H) | GS I |
| 52 | 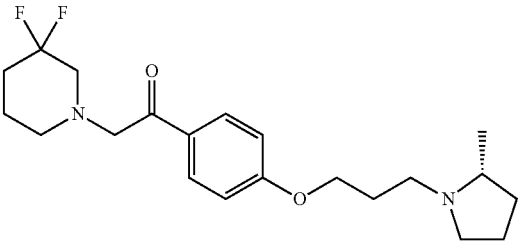  2-(3,3-Difluoro-piperidin-1-yl)-1-{4-[3-((R)-2-methyl-pyrrolidin-1-yl)-propoxy]-phenyl}-ethanone | 80-90 | 381 M + H | GS I |
| 53 | 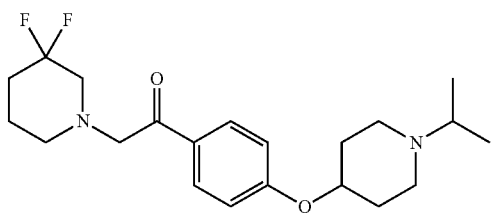  2-(3,3-Difluoro-piperidin-1-yl)-1-[4-(1-isopropyl-piperidin-4-yloxy)-phenyl]-ethanone | 160-165 dec | 381 (M + H) | GS II |
| 54 | 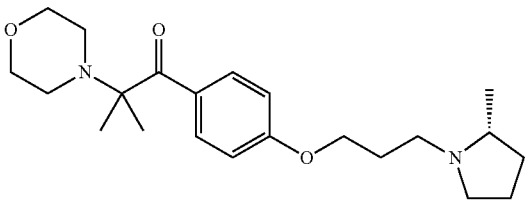  2-Methyl-1-{4-[3-((R)-2-methyl-pyrrolidin-1-yl)-propoxy]-phenyl}-2-morpholin-4-yl-propan-1-one | 45-50 | 375 (M + H) | 5 |

-continued

| Example | Structure | mp (° C.) | MS m/z | Scheme |
|---|---|---|---|---|
| 55 | 2-(3,3-Dimethyl-piperidin-1-yl)-1-{4-[3-((R)-2-methyl-pyrrolidin-1-yl)-propoxy]-phenyl}-ethanone | 108-120 | 373 (M + H) | GS I |
| 56 | 1-{4-[3-(3,3-Difluoro-pyrrolidin-1-yl)-propoxy]-phenyl}-2-morpholin-4-yl-propan-1-one | 254 | 383 (M + H) | GS I |
| 57 | 4-{3-[4-(2-Morpholin-4-yl-acetyl)-phenoxy]-propyl}-piperazin-2-one | 230 | 362 (M + H) | GS I |
| 58 | 2-(2,5-Dimethyl-pyrrolidin-1-yl)-1-{4-[3-((R)-2-methyl-pyrrolidin-1-yl)-propoxy]-phenyl}-ethanone | 100-106 | 359 (M + H) | GS I |

-continued

| Example | Structure | mp (° C.) | MS m/z | Scheme |
|---|---|---|---|---|
| 59 | 1-{4-[3-(4-Methanesulfonyl-piperazin-1-yl)-propoxy]-phenyl}-2-morpholin-4-yl-ethanone | 246-248 | 426 (M + H) | GS I |
| 60 | 2-(3,3-Difluoro-pyrrolidin-1-yl)-1-{4-[3-((R)-2-methyl-pyrrolidin-1-yl)-propoxy]-phenyl}-ethanone | 100-107 | 367 (M + H) | GS I |
| 61 | 2-(2,6-Dimethyl-piperidin-1-yl)-1-{4-[3-((R)-2-methyl-pyrrolidin-1-yl)-propoxy]-phenyl}-ethanone | 127-135 | 373 (M + H) | GS I |
| 62 | 2-Morpholin-4-yl-1-{4-[3-(octahydro-pyrido[1,2-a]pyrazin-2-yl)-propoxy]-phenyl}-ethanone | 251 | 402 (M + H) | GS I |

| Example | Structure | mp (° C.) | MS m/z | Scheme |
|---|---|---|---|---|
| 63 | 2-(4-Acetyl-piperazin-1-yl)-1-{4-[3-((R)-2-methyl-pyrrolidin-1-yl)-propoxy]-phenyl}-ethanone | 125-133 | 388 (M + H) | GS I |
| 64 | 2,2,2-Trifluoro-1-[4-(2-{4-[3-((R)-2-methyl-pyrrolidin-1-yl)-propoxy]-phenyl}-2-oxo-ethyl)-piperazin-1-yl]-ethanone | 115-126 | 442 (M + H) | GS I |
| 65 | 1-[2-Fluoro-4-(3-piperidin-1-yl-propoxy)-phenyl]-2-morpholin-4-yl-ethanone | 170-172 | 365 (M + H) | GS I |
| 66 | 2-(4-Methanesulfonyl-piperazin-1-yl)-1-{4-[3-((R)-2-methyl-pyrrolidin-1-yl)-propoxy]-phenyl}-ethanone | 120-126 | 424 (M + H) | GS I |

-continued

| Example | Structure | mp (° C.) | MS m/z | Scheme |
|---|---|---|---|---|
| 67 | 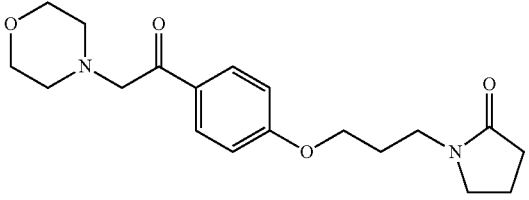 1-{3-[4-(2-Morpholin-4-yl-acetyl)-phenoxy]-propyl}-pyrrolidin-2-one | oil | 347 (M + H) | GS I |
| 68 | 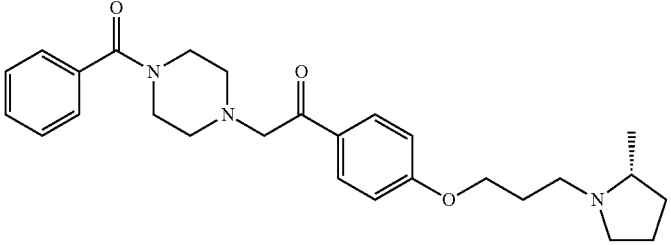 2-(4-Benzoyl-piperazin-1-yl)-1-{4-[3-((R)-2-methyl-pyrrolidin-1-yl)-propoxy]-phenyl}-ethanone | 228-229 | 450 (M + H) | GS I |
| 69 | 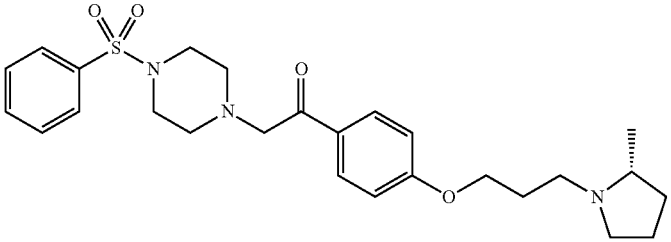 2-(4-Benzenesulfonyl-piperazin-1-yl)-1-{4-[3-((R)-2-methyl-pyrrolidin-1-yl)-propoxy]-phenyl}-ethanone | 124-135 | 486 (M + H) | GS I |
| 70 | 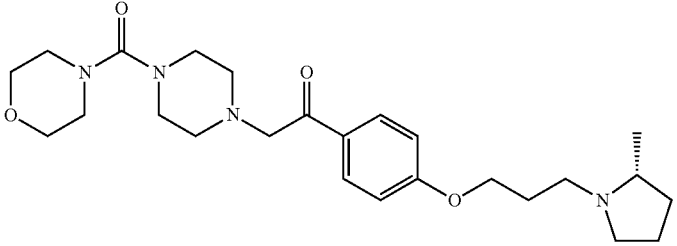 1-{4-[3-((R)-2-Methyl-pyrrolidin-1-yl)-propoxy]-phenyl}-2-[4-(morpholine-4-carbonyl)-piperazin-1-yl]-ethanone | 116-125 | 459 (M + H) | GS I |
| 71 | 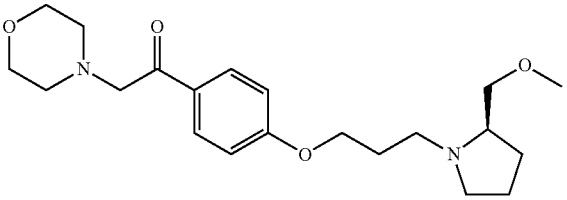 1-{4-[3-((R)-2-Methoxymethyl-pyrrolidin-1-yl)-propoxy]-phenyl}-2-morpholin-4-yl-ethanone | >200 dec | 377 (M + H) | GS I |

-continued

| Example | Structure | mp (° C.) | MS m/z | Scheme |
|---|---|---|---|---|
| 72 | 1-[2-Methyl-4-(3-piperidin-1-yl-propoxy)-phenyl]-2-morpholin-4-yl-ethanone | 206-215 | 361 (M + H) | GS I |
| 73 | 2-(1,3-Dihydro-isoindol-2-yl)-1-{4-[3-((R)-2-methyl-pyrrolidin-1-yl)-propoxy]-phenyl}-ethanone | oil | | GS I |
| 74 | 1-{2-Methyl-4-[3-((R)-2-methyl-pyrrolidin-1-yl)-propoxy]-phenyl}-2-morpholin-4-yl-ethanone | oil | 361 (M + H) | GSI |
| 75 | 1-{4-[3-((R)-2-Methyl-pyrrolidin-1-yl)-propoxy]-phenyl}-2-[4-(pyrrolidine-1-carbonyl)-piperazin-1-yl]-ethanone | 118-130 | 443 (M + H) | GS I |
| 76 | 1-{4-[3-((S)-2-Methoxymethyl-pyrrolidin-1-yl)-propoxy]-phenyl}-2-morpholin-4-yl-ethanone | 74-76 | 377 (M + H) | GS I |

-continued

| Example | Structure | mp (° C.) | MS m/z | Scheme |
|---|---|---|---|---|
| 77 | 2-Methyl-1-[4-(2-{4-[3-((R)-2-methyl-pyrrolidin-1-yl)-propoxy]-phenyl}-2-oxo-ethyl)piperazin-1-yl]-propan-1-one | 220-226 | 416 (M + H) | GS I |
| 78 | 2-Morpholin-4-yl-1-[4-(3-piperidin-1-yl-propoxy)-phenyl]-ethanone | 236-243 | 347 (M + H) | GS I |
| 79 | 4-(2-{4-[3-((R)-2-Methyl-pyrrolidin-1-yl)-propoxy]-phenyl}-2-oxo-ethyl)-piperazine-1-carboxylic acid dimethylamide | 120-126 | 417 (M + H) | GS I |
| 80 | 1-{4-[3-((R)-2-Methyl-pyrrolidin-1-yl)-propoxy]-phenyl}-2-[4-(thiophene-2-carbonyl)-piperazin-1-yl]-ethanone | 152-156 | 456 (M + H) | GS I |

-continued

| Example | Structure | mp (° C.) | MS m/z | Scheme |
|---|---|---|---|---|
| 81 | 2-[4-(Furan-2-carbonyl)-piperazin-1-yl]-1-{4-[3-((R)-2-methyl-pyrrolidin-1-yl)-propoxy]-phenyl}-ethanone | 130-135 | 440 (M + H) | GS I |
| 82 | 4-(2-{4-[3-((R)-2-Methyl-pyrrolidin-1-yl)-propoxy]-phenyl}-2-oxo-ethyl)-piperazine-1-carboxylic acid methyl ester | 208-210 | 404 (M + H) | GS I |
| 83 | 1-{4-[3-((R)-2-Methyl-pyrrolidin-1-yl)-propoxy]-phenyl}-2-[4-(tetrahydro-furan-2-carbonyl)-piperazin-1-yl]-ethanone | 185-190 | 444 (M + H) | GS I |
| 84 | 2-[4-(1-Methyl-1H-pyrrole-2-carbonyl)-piperazin-1-yl]-1-{4-[3-((R)-2-methyl-pyrrolidin-1-yl)-propoxy]-phenyl}-ethanone | 221-224 | 453 (M + H) | GS I |

-continued

| Example | Structure | mp (° C.) | MS m/z | Scheme |
|---|---|---|---|---|
| 85 | 4-(2-{4-[3-((R)-2-Methyl-pyrrolidin-1-yl)-propoxy]-phenyl}-2-oxo-ethyl)-piperazin-2-one | 137-145 | 360 (M + H) | GS I |
| 86 | 2-(5-Fluoro-1,3-dihydro-isoindol-2-yl)-1-{4-[3-((R)-2-methyl-pyrrolidin-1-yl)-propoxy]-phenyl}-ethanone | 68-152 (d) | 397 (M + H) | GSI |
| 87 | 2,2,2-Trifluoro-1-((R)-2-{4-[3-((R)-2-methyl-pyrrolidin-1-yl)-propoxy]-benzoyl}-pyrrolidin-1-yl)-ethanone | 98-101 | 413 (M + H) | 4 |
| 88 | 1-{4-[3-(2,2-Dimethyl-pyrrolidin-1-yl)-propoxy]-phenyl}-2-morpholin-4-yl-ethanone | 117-120 | 361 (M + H) | GS I |

-continued

| Example | Structure | mp (° C.) | MS m/z | Scheme |
|---|---|---|---|---|
| 89 | 2-(4-Cyclopropanecarbonyl-piperazin-1-yl)-1-{4-[3-((R)-2-methyl-pyrrolidin-1-yl)-propoxy]-phenyl}-ethanone | 202-204 | 414 (M + H) | GS I |
| 90 | 1-{4-[3-((R)-2-Methyl-pyrrolidin-1-yl)-propoxy]-phenyl}-2-(4-pyrimidin-2-yl-piperazin-1-yl)-ethanone | 112-114 | 424 (M + H) | GS I |
| 91 | 1-{4-[3-((R)-2-Methyl-pyrrolidin-1-yl)-propoxy]-phenyl}-2-(4-phenyl-piperazin-1-yl)-ethanone | 145-150 | 422 (M + H) | GS I |
| 92 | 1-{4-[3-((R)-2-Methyl-pyrrolidin-1-yl)-propoxy]-phenyl}-2-[4-(4-trifluoromethyl-benzoyl)-piperazin-1-yl]-ethanone | 227-230 | 518 (M + H) | GS I |

-continued

| Example | Structure | mp (° C.) | MS m/z | Scheme |
|---|---|---|---|---|
| 93 | 2-(4-Cyclohexanecarbonyl-piperazin-1-yl)-1-{4-[3-((R)-2-methyl-pyrrolidin-1-yl)-propoxy]-phenyl}-ethanone | 230-232 | 456 (M + H) | GS I |
| 94 | 2-[4-(4-Fluoro-phenyl)-piperazin-1-yl]-1-{4-[3-((R)-2-methyl-pyrrolidin-1-yl)-propoxy]-phenyl}-ethanone | 140-145 | 440 (M + H) | GS I |
| 95 | 2-(4,4-Difluoro-piperidin-1-yl)-1-{3,5-dimethyl-4-[3-((R)-2-methyl-pyrrolidin-1-yl)-propoxy]-phenyl}-ethanone | 140-142 | 409 (M + H) | GS I |
| 96 | 2-(4-Benzoyl-piperazin-1-yl)-1-{3,5-dichloro-4-[3-((R)-2-methyl-pyrrolidin-1-yl)-propoxy]-phenyl}ethanone | 111 | 518 (M) | GS I |

-continued

| Example | Structure | mp (° C.) | MS m/z | Scheme |
|---|---|---|---|---|
| 97 | 2-(4-Acetyl-piperazin-1-yl)-1-{3,5-dimethyl-4-[3-((R)-2-methyl-pyrrolidin-1-yl)-propoxy]-phenyl}-ethanone | 118-119 | 416 (M + H) | GS I |
| 98 | 1-{3,5-Dichloro-4-[3-((R)-2-methyl-pyrrolidin-1-yl)-propoxy]-phenyl}-2-(4,4-difluoro-piperidin-1-yl)-ethanone | 102 | 449 (M) | GS I |
| 99 | 2-(4-Cyclohexanecarbonyl-piperazin-1-yl)-1-{3,5-dichloro-4-[3-((R)-2-methyl-pyrrolidin-1-yl)-propoxy]-phenyl}-ethanone | 168 | 524 (M) | GS I |
| 100 | 2-[4-(4-Chloro-benzoyl)-piperazin-1-yl]-1-{4-[3-((R)-2-methyl-pyrrolidin-1-yl)-propoxy]-phenyl}-ethanone | 233-236 | 485 (M + H) | GS I |

-continued

| Example | Structure | mp (° C.) | MS m/z | Scheme |
|---|---|---|---|---|
| 101 | 2-[4-(4-Fluoro-benzoyl)-piperazin-1-yl]-1-{4-[3-((R)-2-methyl-pyrrolidin-1-yl-propoxy]-phenyl}-ethanone | 225-229 | 468 (M + H) | GS I |
| 102 | 1-{3,5-Dichloro-4-[3-((R)-2-methyl-pyrrolidin-1-yl)-propoxy]-phenyl}-2-(4-phenyl-piperazin-1-yl)-ethanone | 168 | 490 (M) | GS I |
| 103 | 2-(4-Benzoyl-piperazin-1-yl)-1-{2-fluoro-4-[3-((R)-2-methyl-pyrrolidin-1-yl)-propoxy]-phenyl}-ethanone | 98-101 | 468 (M + H) | 2 |
| 104 | 1-{3,5-Dimethyl-4-[3-((R)-2-methyl-pyrrolidin-1-yl)-propoxy]-phenyl}-2-(4-pyrimidin-2-yl-piperazin-1-yl)-ethanone | 155-160 dec. | 452 (M + H) | GS I |

-continued

| Example | Structure | mp (° C.) | MS m/z | Scheme |
|---|---|---|---|---|
| 105 | 1-{4-[3-((R)-2-Methyl-pyrrolidin-1-yl)-propoxy]-phenyl}-2-[4-(4-trifluoromethyl-phenyl)-piperazin-1-yl]-ethanone | 230-233 | 490 (M + H) | GS I |
| 106 | 2-(4-Benzoyl-piperazin-1-yl)-1-{3,5-dimethyl-4-[3-((R)-2-methyl-pyrrolidin-1-yl)-propoxy]-phenyl}-ethanone | 110-120 | 478 (M + H) | GS I |
| 107 | 2-(4-Benzoyl-piperazin-1-yl)-1-{3-methyl-4-[3-((R)-2-methyl-pyrrolidin-1-yl)-propoxy]-phenyl}-ethanone | oil | 464 (M + H) | GS I |
| 108 | 2-(3,4-Dihydro-2H-quinolin-1-yl)-1-{4-[3-((R)-2-methyl-pyrrolidin-1-yl)-propoxy]-phenyl}-ethanone | 166-168 | 393 (M + H) | GS I |

-continued

| Example | Structure | mp (° C.) | MS m/z | Scheme |
|---|---|---|---|---|
| 109 | 1-{4-[3-((R)-2-Methyl-pyrrolidin-1-yl)-propoxy]-phenyl}-2-[4-(naphthalene-2-carbonyl)-piperazin-1-yl]-ethanone | 100.5–109.5 | 500 (M + H) | GS I |
| 110 | 2-(4-Acetyl-piperazin-1-yl)-1-{3,5-dichloro-4-[3-((R)-2-methyl-pyrrolidin-1-yl)-propoxy]-phenyl}-ethanone | 115 | 456 (M) | GS I |
| 111 | 1-{3,5-Dichloro-4-[3-((R)-2-methyl-pyrrolidin-1-yl)-propoxy]-phenyl}-2-(4-pyrimidin-2-yl-piperazin-1-yl)-ethanone | 177 | 492 (M) | GS I |
| 112 | 2-(4-Benzoyl-piperazin-1-yl)-1-{3-methoxy-4-[3-((R)-2-methyl-pyrrolidin-1-yl)-propoxy]-phenyl}-ethanone | oil | 480 (M + H) | GS I |

-continued

| Example | Structure | mp (° C.) | MS m/z | Scheme |
|---|---|---|---|---|
| 113 | 2-(4-Benzoyl-piperazin-1-yl)-1-{3-chloro-4-[3-((R)-2-methyl-pyrrolidin-1-yl)-propoxy]-phenyl}-ethanone | 130-137 | 484 (M + H) | GS I |
| 114 | 1-{4-[3-((R)-2-Methyl-pyrrolidin-1-yl)-propoxy]-phenyl}-2-(2,3,4,5-tetrahydro-benzo[b]azepin-1-yl)-ethanone | 90-96 | 407 (M + H) | GS I |
| 115 | 4-(2-{4-[3-((R)-2-Methyl-pyrrolidin-1-yl)-propoxy]-phenyl}-2-oxo-ethyl)-piperazine-1-carboxylic acid ethyl ester | 218-219 | 418 (M + H) | GS I |
| 116 | 1-{4-[3-((R)-2-Methyl-pyrrolidin-1-yl)-propoxy]-phenyl}-2-(4-pyridin-2-yl-piperazin-1-yl)-ethanone | 239-242 | 423 (M + H) | GS I |

-continued

| Example | Structure | mp (° C.) | MS m/z | Scheme |
|---|---|---|---|---|
| 117 | 4-(2-{4-[3-((R)-2-Methyl-pyrrolidin-1-yl)-propoxy]-phenyl}-2-oxo-ethyl)-piperazine-1-carboxylic acid tert-butyl ester | 198-199 | 446 (M + H) | GS I |
| 118 | 1-[4-(2-{3-Chloro-4-[3-((R)-2-methyl-pyrrolidin-1-yl)-propoxy]-phenyl}-2-oxo-ethyl)-piperazin-1-yl]-2-methyl-propan-1-one | 140 C. dec. | 450 (M + H) | GS I |
| 119 | 1-{3-Fluoro-4-[3-((R)-2-methyl-pyrrolidin-1-yl)-propoxy]-phenyl}-2-(4-pyrimidin-2-yl-piperazin-1-yl)-ethanone | 219 | 442 (M + H) | GS I |
| 120 | 2-(4-Benzoyl-piperazin-1-yl)-1-{3-fluoro-4-[3-((R)-2-methyl-pyrrolidin-1-yl)-propoxy]-phenyl}-ethanone | 96 | 468 (M + H) | GSI |

-continued

| Example | Structure | mp (° C.) | MS m/z | Scheme |
|---|---|---|---|---|
| 121 | 1-[4-(2-{3-Fluoro-4-[3-((R)-2-methyl-pyrrolidin-1-yl)-propoxy]-phenyl}-2-oxo-ethyl)-piperazin-1-yl]-2-methyl-propan-1-one | 75 | 434 (M + H) | GS I |
| 122 | 1-{3-Fluoro-4-[3-((R)-2-methyl-pyrrolidin-1-yl)-propoxy]-phenyl}-2-(4-methanesulfonyl-piperazin-1-yl)-ethanone | 86 | 442 (M + H) | GS I |
| 123 | 4-(2-{3-Fluoro-4-[3-((R)-2-methyl-pyrrolidin-1-yl)-propoxy]-phenyl}-2-oxo-ethyl)-piperazine-1-carboxylic acid dimethylamide | 81 | 435 (M + H) | GS I |
| 124 | 2-[4-(Benzo[b]thiophene-2-carbonyl)-piperazin-1-yl]-1-{4-[3-((R)-2-methyl-pyrrolidin-1-yl)-propoxy]-phenyl}-ethanone | 214-217 | 506 (M + H) | GS I |

-continued

| Example | Structure | mp (° C.) | MS m/z | Scheme |
|---|---|---|---|---|
| 125 | 1-{3-Chloro-4-[3-((R)-2-methyl-pyrrolidin-1-yl)-propoxy]-phenyl}-2-(4-pyrimidin-2-yl-piperazin-1-yl)-ethanone | 112-114 | 458 (M + H) | GS I |
| 126 | 2-[4-(2,4-Difluoro-benzoyl)-piperazin-1-yl]-1-{4-[3-((R)-2-methyl-pyrrolidin-1-yl)-propoxy]-phenyl}-ethanone | 115-117 | 486 (M + H) | GS I |
| 127 | 4-(2-{3-Fluoro-4-[3-((R)-2-methyl-pyrrolidin-1-yl)-propoxy]-phenyl}-2-oxo-ethyl)-piperazine-1-carboxylic acid methyl ester | 236 | 422 (M + H) | GS I |
| 128 | 4-(2-{4-[3-((R)-2-Methyl-pyrrolidin-1-yl)-propoxy]-phenyl}-2-oxo-ethyl)-piperazine-1-carboxylic acid phenyl ester | 194-199 | 466 (M + H) | GS I |

-continued

| Example | Structure | mp (° C.) | MS m/z | Scheme |
|---|---|---|---|---|
| 129 | 2-[4-(3,4-Dichloro-benzoyl)-piperazin-1-yl]-1-{4-[3-((R)-2-methyl-pyrrolidin-1-yl)-propoxy]-phenyl}-ethanone | 88-90.5 | 518 (M + H) | GS I |
| 130 | 1-{3-Methyl-4-[3-((R)-2-methyl-pyrrolidin-1-yl)-propoxy]-phenyl}-2-(4-pyrimidin-2-yl-piperazin-1-yl)-ethanone | 231.5-235.0 | 438 (M + H) | GS I |
| 131 | 4-(2-{4-[3-((R)-2-Methyl-pyrrolidin-1-yl)-propoxy]-phenyl}-2-oxo-ethyl)-piperazine-1-carboxylic acid isobutyl ester | 219-222 | 446 (M + H) | GS I |
| 132 | 4-(2-{3-Chloro-4-[3-((R)-2-methyl-pyrrolidin-1-yl)-propoxy]-phenyl}-2-oxo-ethyl)-piperazine-1-carboxylic acid methyl ester | 122-124 | 438 (M + H) | GS I |

| Example | Structure | mp (° C.) | MS m/z | Scheme |
|---|---|---|---|---|
| 133 | 1-{4-[3-((R)-2-Methyl-pyrrolidin-1-yl)-propoxy]-phenyl}-2-[4-(naphthalene-1-carbonyl)-piperazin-1-yl]-ethanone | 162-245 | 500 (M + H) | GS I |
| 134 | 1-{3-Chloro-4-[3-((R)-2-methyl-pyrrolidin-1-yl)-propoxy]-phenyl}-2-(4,4-difluoro-piperidin-1-yl)-ethanone | 130-143 | 415 (M + H) | GS I |
| 135 | 2-(4-Acetyl-piperazin-1-yl)-1-{3-chloro-4-[3-((R)-2-methyl-pyrrolidin-1-yl)-propoxy]-phenyl}-ethanone | 113-128 | 422 (M + H) | GS I |
| 136 | 2-(4,4-Difluoro-piperidin-1-yl)-1-{3-methyl-4-[3-((R)-2-methyl-pyrrolidin-1-yl)-propoxy]-phenyl}-ethanone | 212.7-215.7 | 418 (M + H) | GS I |

| Example | Structure | mp (° C.) | MS m/z | Scheme |
|---|---|---|---|---|
| 137 | 4-(2-{3-Methyl-4-[3-((R)-2-methyl-pyrrolidin-1-yl)-propoxy]-phenyl}-2-oxo-ethyl)-piperazine-1-carboxylic acid methyl ester | oil | 395 (M + H) | GS I |
| 138 | 4-(2-{4-[3-((R)-2-Methyl-pyrrolidin-1-yl)-propoxy]-phenyl}-2-oxo-ethyl)-piperazine-1-carboxylic acid benzyl ester | 183-188 | 480 (M + H) | GS I |
| 139 | 2-(3,3-Difluoro-pyrrolidin-1-yl)-1-{3-fluoro-4-[3-((R)-2-methyl-pyrrolidin-1-yl)-propoxy]-phenyl}-ethanone | 206 | 385 (M + H) | GS I |
| 140 | 2-[4-(3,5-Dimethyl-benzoyl)-piperazin-1-yl]-1-{4-[3-((R)-2-methyl-pyrrolidin-1-yl)-propoxy]-phenyl}-ethanone | oil | 478 (M + H) | GS I |

| Example | Structure | mp (° C.) | MS m/z | Scheme |
|---|---|---|---|---|
| 141 | 2-(4,4-Difluoro-piperidin-1-yl)-1-{3-fluoro-4-[3-((R)-2-methyl-pyrrolidin-1-yl)-propoxy]-phenyl}-ethanone | 220 | 399 (M + H) | GS I |
| 142 | 2-(2-Methyl-benzoimidazol-1-yl)-1-{4-[3-((R)-2-methyl-pyrrolidin-1-yl)-propoxy]-phenyl}-ethanone | oil | 392 (M + H) | GS I |
| 143 | 1-{3-Fluoro-4-[3-((R)-2-methyl-pyrrolidin-1-yl)-propoxy]-phenyl}-2-(4-phenyl-piperazin-1-yl)-ethanone | 140 | 440 (M + H) | GS I |
| 144 | 1-[4-(2-{4-[3-((R)-2-Methyl-pyrrolidin-1-yl)-propoxy]-phenyl}-2-oxo-ethyl)-piperazin-1-yl]-propan-1-one | 65-70 | 402 (M + H) | GSI |

-continued

| Example | Structure | mp (° C.) | MS m/z | Scheme |
|---|---|---|---|---|
| 145 | 1-{4-[3-((R)-2-Methyl-pyrrolidin-1-yl)-propoxy]-phenyl}-2-[4-(quinoline-2-carbonyl)-piperazin-1-yl]-ethanone | 115.4-120 | 501 (M + H) | GS I |
| 146 | 2-(4-Cyclohexanecarbonyl-piperazin-1-yl)-1-{3-fluoro-4-[3-((R)-2-methyl-pyrrolidin-1-yl)-propoxy]-phenyl}-ethanone | 232 | 474 (M + H) | GS I |
| 147 | 1-[3-Chloro-4-(3-piperidin-1-yl-propoxy)-phenyl]-2-(4,4-difluoro-piperidin-1-yl)-ethanone | 122-135 | 415 (M + H) | GS I |
| 148 | 2-(4-Cyclohexanecarbonyl-piperazin-1-yl)-1-{3-methyl-4-[3-((R)-2-methyl-pyrrolidin-1-yl)-propoxy]-phenyl}-ethanone | 161-166.5 | 470 (M + H) | GS I |

-continued

| Example | Structure | mp (° C.) | MS m/z | Scheme |
|---|---|---|---|---|
| 149 | 4-(2-{4-[3-((R)-2-Methyl-pyrrolidin-1-yl)-propoxy]-phenyl}-2-oxo-ethyl)-piperazine-1-carboxylic acid 4-fluoro-phenyl ester | 234-236 | 484 (M + H) | GS I |
| 150 | 4-(2-{3-Methyl-4-[3-((R)-2-methyl-pyrrolidin-1-yl)-propoxy]-phenyl}-2-oxo-ethyl)-piperazin-2-one | 79-85 | 374 (M + H) | GS I |
| 151 | 2-(4-Benzoyl-piperazin-1-yl)-1-[3-chloro-4-(3-piperidin-1-yl-propoxy)-phenyl]-ethanone | 120-130 | 484 (M + H) | GS I |
| 152 | 2-[4-(Biphenyl-2-carbonyl)-piperazin-1-yl]-1-{4-[3-((R)-2-methyl-pyrrolidin-1-yl)-propoxy]-phenyl}-ethanone | 117-119 | 526 (M + H) | GS I |

| Example | Structure | mp (° C.) | MS m/z | Scheme |
|---|---|---|---|---|
| 153 | 2-(4-Benzoyl-piperazin-1-yl)-1-{3-[3-((R)-2-methyl-pyrrolidin-1-yl)-propoxy]-phenyl}-ethanone | 125-135 | 450 (M + H) | 2 |
| 154 | 2-(4,4-Difluoro-piperidin-1-yl)-1-{3-[3-((R)-2-methyl-pyrrolidin-1-yl)-propoxy]-phenyl}-ethanone | 110-120 | 381 (M + H) | GS I |
| 155 | 1-Methyl-4-(2-{4-[3-((R)-2-methyl-pyrrolidin-1-yl)-propoxy]-phenyl}-2-oxo-ethyl)-piperazin-2-one | 115-120 | 374 (M + H) | GS I |
| 156 | 2-(4-Acetyl-piperazin-1-yl)-1-{3-methyl-4-[3-((R)-2-methyl-pyrrolidin-1-yl)-propoxy]-phenyl}-ethanone | 120-126 | 402 (M + H) | GS I |
| 157 | 2-[4-(2,3-Dichloro-benzoyl)-piperazin-1-yl]-1-{4-[3-((R)-2-methyl-pyrrolidin-1-yl)-propoxy]-phenyl}-ethanone | 137-150 | 518 (M); 520 (M + 2) | GS I |

| Example | Structure | mp (° C.) | MS m/z | Scheme |
|---|---|---|---|---|
| 158 | 4-(2-{4-[3-((R)-2-Methyl-pyrrolidin-1-yl)-propoxy]-phenyl}-2-oxo-ethyl)-piperazine-1-carboxylic acid isopropyl ester | 222-224 | 432 (M + H) | GS I |

Oximes

Compounds belonging to this class were synthesized according to General Scheme IV. Thus, a suitably substituted bromomethyl ketone (compound CC) was transformed into the corresponding oxime (compound L) by treatment with an appropriate hydroxylamine derivative. Sequential treatment of compound L with an amine gives α-aminooxime derivative M followed by a second amine treatment yielding target compound N.

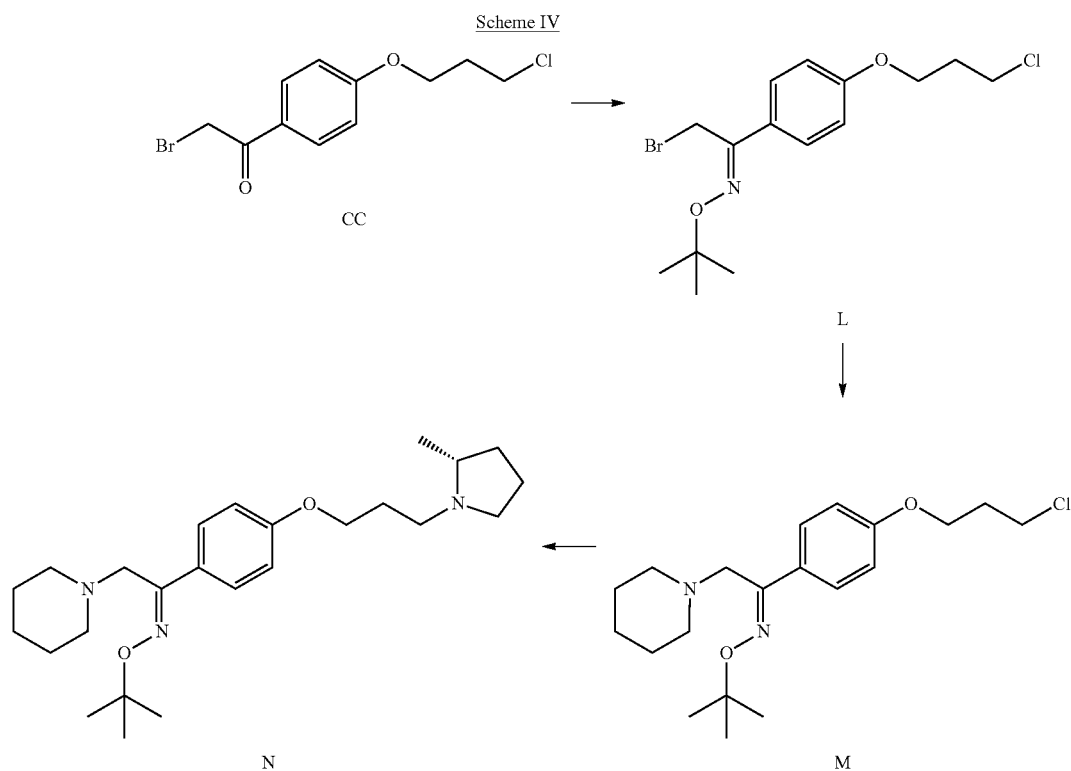

Scheme IV

Application of the above-mentioned methodology has been exemplified in the synthesis of compound N1, Example 160 described in Scheme 7.

Scheme 7

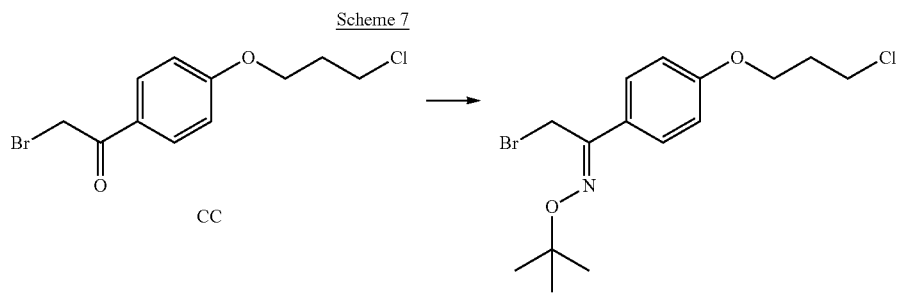

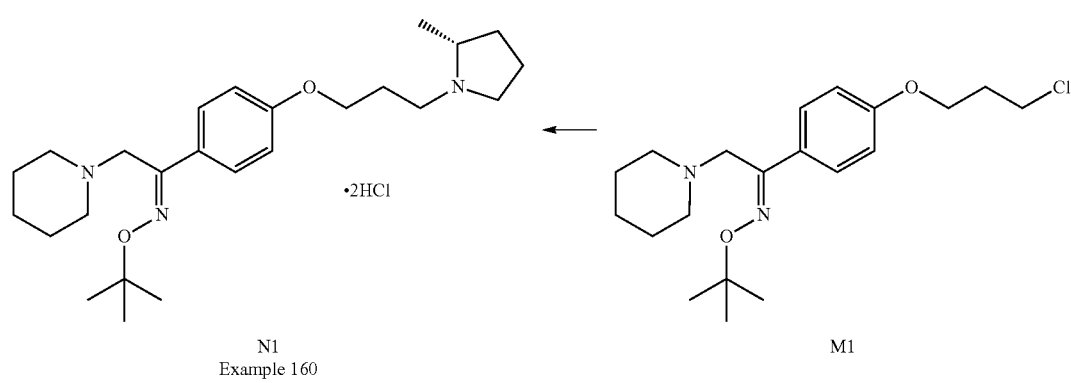

Example 160

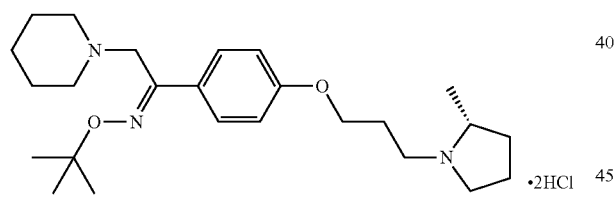

1-{4-[3-((R)-2-Methyl-pyrrolidin-1-yl)-propoxy]-
phenyl}-2-piperidin-1-yl-ethanone
O-tert-butyl-oxime dihydrochloride Preparation of Compound L1

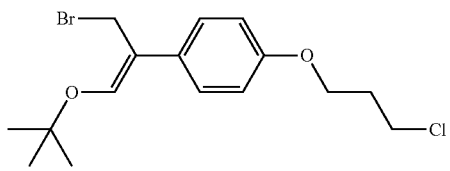

2-Bromo-1-[4-(3-chloro-propoxy)-phenyl]-
ethanone O-tert-butyl-oxime

A mixture of compound CC (2.20 g, 7.56 mmol), O-tert-butylhydroxylamine hydrochloride (1.05 g, 8.36 mmol), methanol (30 mL) and water (5 mL) was stirred at room temperature for 16 h, concentrated, and taken into dichloromethane (100 mL). The organic layer was washed with water, dried (MgSO$_4$) and concentrated to give crude compound L1 (2.45 g) as a brown oil that was directly taken into the next step.

Preparation of Compound M1

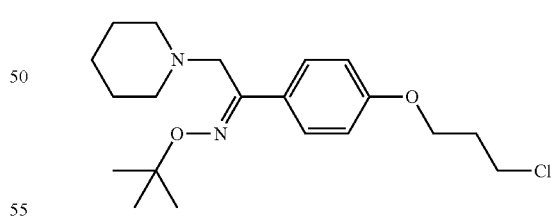

1-[4-(3-Chloro-propoxy)-phenyl]-2-piperidin-1-
yl-ethanone O-tert-butyl-oxime

A mixture of compound L1 (2.96 g, 8.20 mmol), piperidine (0.70 g, 8.2 mmol), diisopropylethylamine (1.10 g, 8.5 mmol) and ethanol (50 mL) was stirred at room temperature for 24 h and concentrated to dryness. The crude product was then purified by column chromatography (silica gel, 5% methanol in dichloromethane) to generate 2.35 g of compound M1 (2.35 g) as colorless oil.

Preparation of N1

Example 160

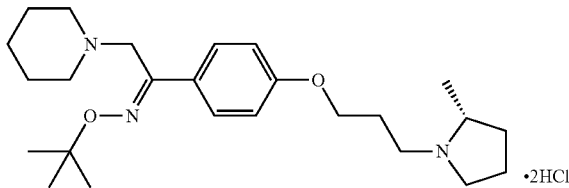

1-{4-[3-((R)-2-Methyl-pyrrolidin-1-yl)-propoxy]-phenyl}-2-piperidin-1-yl-ethanone O-tert-butyl-oxime dihydrochloride A mixture of compound M1 (2.63 g, 7.20 mmol), 2-(R)-methylpyrrolidine tartrate (3.40 g, 14.50 mmol), diisopropylethylamine (2.0 g, 15.50 mmol), $K_2CO_3$ (2.50 g, 18 mmol), sodium iodide (0.50 g) and 2-butanone (200 mL) was heated at reflux for 96 h, cooled, filtered and the residue washed several times with small amounts of 2-butanone. The combined filtrate and washings were evaporated to dryness to give a crude product that was purified by column chromatography (silica gel, 10% methanol in dichloromethane) yielding 2.70 g of an oil; The purified oil product (2.20 g) was dissolved in ethyl acetate (30 mL), cooled and treated with 4 (N) HCl in ethyl acetate. The resulting suspension produced was separated, washed successively with ethyl acetate and ethyl ether, and dried under vacuum (40° C.) to give 2.45 g of Example 160, compound N1 as the dihydrochloride salt.

Additional oxime examples tabulated below were prepared as described above.

| Example | Structure | mp (° C.) | MS m/z | Scheme |
|---|---|---|---|---|
| 159 | 1-{4-[3-((R)-2-Methyl-pyrrolidin-1-yl)-propoxy]-phenyl}-2-piperidin-1-yl-ethanone O-methyl-oxime | NA | 374 (M + H) | GS IV |
| 160 | 1-{4-[3-((R)-2-Methyl-pyrrolidin-1-yl)-propoxy]-phenyl}-2-piperidin-1-yl-ethanone O-tert-butyl-oxime | NA | 416 (M + H) | 7 |
| 161 | 1-{4-[3-((R)-2-Methyl-pyrrolidin-1-yl)-propoxy]-phenyl}-2-piperidin-1-yl-ethanone O-methyl-oxime | NA | 374 (M + H) | GS IV |

| Example | Structure | mp (° C.) | MS m/z | Scheme |
|---|---|---|---|---|
| 162 | 1-{4-[3-(2-Methyl-pyrrolidin-1-yl)-propoxy]-phenyl}-2-piperidin-1-yl-ethanone O-benzyl-oxime | NA | 450 (M + H) | GS IV |
| 163 | 2-Piperidin-1-yl-1-[4-(3-piperidin-1-yl-propoxy)-phenyl]-propan-1-one O-methyl-oxime | NA | 388 (M + H) | GS IV |
| 164 | 2-Piperidin-1-yl-1-[4-(3-piperidin-1-yl-propoxy)-phenyl]-propan-1-one O-benzyl-oxime | NA | 464 (M + H) | GS IV |
| 165 | 1-{4-[3-(2-Methyl-pyrrolidin-1-yl)-propoxy]-phenyl}-2-morpholin-4-yl-ethanone O-tert-butyl-oxime | NA | 418 (M + H) | GS IV |

| Example | Structure | mp (° C.) | MS m/z | Scheme |
|---|---|---|---|---|
| 166 | 1-{4-[3-(2-Methyl-pyrrolidin-1-yl)-propoxy]-phenyl}-2-(4-phenyl-piperazin-1-yl)-ethanone O-tert-butyl-oxime | NA | 493 (M + H) | GS IV |
| 167 | 1-(2-[(Z)-tert-Butoxyimino]-2-{4-[3-((R)-2-methyl-pyrrolidin-1-yl)-propoxy]-phenyl}-ethyl)-piperidin-2-one | NA | 430 (M + H) | GS IV |
| 168 | 1-{4-[3-((R)-2-Methyl-pyrrolidin-1-yl)-propoxy]-phenyl}-2-(2-phenyl-morpholin-4-yl)-ethanone O-tert-butyl-oxime | NA | 494 (M + H) | GS IV |
| 169 | 1-{4-[3-(2-Methyl-pyrrolidin-1-yl)-propoxy]-phenyl}-2-piperidin-1-yl-propan-1-one O-methyl-oxime | NA | 388 (M + H) | GS IV |

| Example | Structure | mp (° C.) | MS m/z | Scheme |
|---|---|---|---|---|
| 170 | 1-{4-[3-((R)-2-Methyl-pyrrolidin-1-yl)-propoxy]-phenyl}-2-morpholin-4-yl-ethanone O-cyclohexyl-oxime | NA | 444 (M + H) | GS IV |
| 171 | 1-{4-[3-((R)-2-Methyl-pyrrolidin-1-yl)-propoxy]-phenyl}-2-morpholin-4-yl-ethanone O-isopropyl-oxime | NA | 404 (M + H) | GS IV |

EXAMPLES

Other features of the invention will become apparent in the course of the following descriptions of exemplary embodiments as shown below. The compounds shown herein have activity in the targets described herein at concentrations ranging from 0.1 nM to 10 µM. These examples are given for illustration of the invention and are not intended to be limiting thereof.

The compounds of the present invention are useful, inter alia, as therapeutic agents. Particularly, the compounds are useful for interacting with the $H_3$ receptor. In one embodiment, the present invention provides a method for treating or preventing diseases and disorders, such as those disclosed herein, which comprises administering to a subject in need of such treatment or prevention a therapeutically effective amount of a compound of the present invention.

In an additional embodiment, the present invention provides a method for inhibiting $H_3$ activity comprising providing a compound of the present invention in an amount sufficient to result in effective inhibition. Particularly, the compounds of the present invention can be administered to treat such diseases and disorders such as narcolepsy or other sleep/wake disorders, such as obstructive sleep apnea/hypopnea syndrome, and shift work sleep disorder; feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders (such as asthma), inflammation, and myocardial infarction. In certain embodiments, the compounds can be administered to treat narcolepsy or other sleep/wake disorders, such as obstructive sleep apnea/hypopnea syndrome, and shift work sleep disorder; obesity, cognition, attention deficit hyperactivity disorder (ADHD), and dementia. In other embodiments, the compounds can be administered to treat narcolepsy or other sleep/wake disorders, such as obstructive sleep apnea/hypopnea syndrome, and shift work sleep disorder; or they can used to treat obesity, or they can used to treat cognition, or they can used to treat attention deficit hyperactivity disorder (ADHD), or they can used to treat dementia.

Compounds of the invention have demonstrated inhibition of $H_3$, and thereby are expected to be useful for treatment of the indications described herein. Such utilities can be determined using, for example, the following assays as set forth below. They are not intended, nor are they to be construed, as limiting the scope of the disclosure.

Rat $H_3$ Assays:

Cell Line Development and Membrane Preparation.

The rat $H_3$ receptor cDNA was PCR amplified from reverse-transcribed RNA pooled from rat thalamus, hypothalamus, striatum and prefrontal cortex with a sequence corresponding to by #338-1672 of Genbank file #NM__053506, encoding the entire 445-amino-acid rat histamine $H_3$ receptor. This was engineered into the pIRES-neo3 mammalian expression vector, which was stably transfected into the CHO-A3 cell line (Euroscreen, Belgium), followed by clonal selection by limiting dilution. Cells were harvested and cell pellets were frozen (−80° C.). Cell pellets were resuspended in 5 mM Tris-HCl, pH 7.5 with 5 nM EDTA and a cocktail of protease inhibitors (Complete Protease Inhibitor Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM $MgCl_2$ and protease inhibitors, recentrifuged as above and the final pellet resuspended in membrane buffer plus 250 mM sucrose and frozen at −80° C.

Radioligand Binding.

Membranes were resuspended in 50 mM Tris HCl (pH 7.4), 5 mM $MgCl_2$, 0.1% BSA. The membrane suspensions (10 µg protein per well) were incubated in a 96 well microtiter plate with [$^3$H]-N-alpha-methylhistamine (approximately 1 nM final concentration), test compounds at various concentrations (0.01 nM-30 µM) and scintillation proximity beads (Perkin Elmer, FlashBlueGPCR Scintillating Beads) in a final volume of 80 µl for 4 hours at room temperature, protected from light. Non-specific binding was determined in the presence of 10 µclobenpropit. Radioligand bound to receptor, and therefore in proximity to the scintillation beads, was measured using a MicroBeta scintillation counter.

GTPγS Binding.

Membranes were resuspended in 20 mM HEPES pH 7.4 containing: 1 mM EDTA, 0.17 mg/ml dithiothreitol, 100 mM NaCl, 30 µg/ml saponin and 5 mM $MgCl_2$. For measurement of inverse agonist activity, increasing concentrations of test compounds were incubated in a 96 well microtiter plate with 10 µg/well membrane protein, 5 µM GDP, scintillation proximity beads (Perkin Elmer, FlashBlueGPCR Scintillating Beads) and [$^{35}$S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 µM GTP. A decrease in bound [$^{35}$S]-GTPγS is indicative of $H_3$ receptor inverse agonist activity in this assay. Antagonist activity of test compounds was determined in a similar experiment under the following conditions. Membranes were resuspended in 20 mM HEPES pH 7.4 containing: 1 mM EDTA, 0.17 mg/ml dithiothreitol, 200 mM NaCl, 30 µg/ml saponin and 20 mM $MgCl_2$. The membranes were incubated at 10 µg/well membrane protein in a microtiter plate with increasing concentrations of test compounds, 20 µM GDP, scintillation proximity beads and [$^{35}$S]-GTPγS (0.1 nM final concentration) plus 30 nM R-alpha-methylhistamine. The microtiter plates were incubated and processed as described above. A decrease in R-alpha-methylhistamine stimulated [$^{35}$S]-GTPγS binding is indicative of $H_3$ receptor antagonist activity in this assay.

Human $H_3$ Assays:

Methods:

CHO cells stably expressing the human $H_3$ receptor (GenBank: NM_007232) were harvested and cell pellets were frozen (−80° C.). Cell pellets were resuspended in 5 mM Tris-HCl, pH 7.5 with 5 nM EDTA and a cocktail of protease inhibitors (Complete Protease Inhibitor Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM $MgCl_2$ and protease inhibitors, recentrifuged as above and the final pellet resuspended in membrane buffer plus 250 mM sucrose and frozen at −80° C.

Radioligand Binding.

Membranes were resuspended in 50 mM Tris HCl (pH 7.4), 5 mM $MgCl_2$, 0.1% BSA. The membrane suspensions (10 µg protein per well) were incubated in a 96 well microtiter plate with [$^3$H]-N-alpha-methylhistamine (approximately 1 nM final concentration), test compounds at various concentrations (0.01 nM-30 µM) and scintillation proximity beads (Perkin Elmer, FlashBlueGPCR Scintillating Beads) in a final volume of 80 µl for 4 hours at room temperature, protected from light. Non-specific binding was determined in the presence of 10 µM clobenpropit. Radioligand bound to receptor, and therefore in proximity to the scintillation beads, was measured using a MicroBeta scintillation counter.

GTPγS Binding.

Membranes were resuspended in 20 mM HEPES pH 7.4 containing: 1 mM EDTA, 0.17 mg/ml dithiothreitol, 100 mM NaCl, 30 µg/ml saponin and 5 mM $MgCl_2$. For measurement of inverse agonist activity, increasing concentrations of test compounds were incubated in a 96 well microtiter plate with 10 µg/well membrane protein, 5 µM GDP, scintillation proximity beads (Perkin Elmer, FlashBlueGPCR Scintillating Beads) and [$^{35}$S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 µM GTP. A decrease in bound [$^{35}$S]-GTPγS is indicative of $H_3$ receptor inverse agonist activity in this assay. Antagonist activity of test compounds was determined in a similar experiment under the following conditions. Membranes were resuspended in 20 mM HEPES pH 7.4 containing: 1 mM EDTA, 0.17 mg/ml dithiothreitol, 200 mM NaCl, 30 µg/ml saponin and 20 mM $MgCl_2$. The membranes were incubated at 10 µg/well membrane protein in a microtiter plate with increasing concentrations of test compounds, 20 µM GDP, scintillation proximity beads and [$^{35}$S]-GTPγS (0.1 nM final concentration) plus 30 nM R-alpha-methylhistamine. The microtiter plates were incubated and processed as described above. A decrease in R-alpha-methylhistamine stimulated [$^{35}$S]-GTPγS binding is indicative of $H_3$ receptor antagonist activity in this assay.

Other assays that may be used in connection with the present invention are set forth below. Examples of the present invention can be tested in the following in vivo models:

Evaluation of Wake Promoting Activity in Rats:

The methodology utilized for evaluating wake promoting activity of test compounds is based on that described by Edgar and Seidel, *Journal of Pharmacology and Experimental Therapeutics,* 283:757-769, 1997, and incorporated herein in its entirety by reference.

Compounds of the invention either have demonstrated or are expected to demonstrate utility for wake promoting activity.

Dipsogenia Model:

Inhibition of histamine agonist-induced water drinking in the rat. Histamine, and the $H_3$-selective agonist (R)-α-methylhistamine (RAMH) induce water drinking behavior in the rat when administered either peripherally or centrally (Kraly, F. S., June, K. R. 1982 *Physiol. Behav.* 28: 841.; Leibowitz, S. F. 1973 *Brain Res.* 63:440; Ligneau X., Lin, J-S., Vanni-Mercier G., Jouvet M., Muir J. L., Ganellin C. R., Stark H., Elz S., Schunack W., Schwartz, J-C. 1998 *J Pharmcol. Exp. Ther.* 287:658-66.; Clapham, J. and Kilpatrick G. J. 1993 *Eur. J. Pharmacol.* 232:99-103) an effect which is blocked by $H_3$ receptor antagonists thioperamide and ciproxifan. Compounds of the invention either have demonstrated or are expected to block RAMH induce water drinking behavior.

Novel Object Discrimination:

Novel object discrimination (NOD; also referred to as novel object recognition) is an assay for short-term visual recognition memory that was first described by Ennaceur and Delacour (Ennaceur, A. and Delacour, J. (1988) *Behav Brain Res* 31: 47-59).

Social Recognition:

Social recognition (SR) is an assay for short-term social (olfactory) memory that was first described by Thor and Holloway (1982). Thor, D. and Holloway, W. (1982) *J Comp Physiolog Psychcol* 96: 1000-1006.

Table A lists the Human and Rat $H_3$ binding data for Examples 1-171 of the present invention.

TABLE A $H_3$ Phenoxypropylcycloamine Binding Data

| Example | Human $H_3$ $K_i$ nM | Rat $H_3$ $K_i$ nM |
|---|---|---|
| 1 | A | A |
| 2 | A | |
| 3 | A | |
| 4 | A | |
| 5 | A | |
| 6 | A | |
| 7 | A | |
| 8 | A | A |
| 9 | A | |
| 10 | A | |
| 11 | A | |
| 12 | A | |
| 13 | A | |
| 14 | A | |
| 15 | B | C |
| 16 | A | |
| 17 | A | |
| 18 | A | |
| 19 | A | |
| 20 | A | |
| 21 | A | B |
| 22 | A | B |
| 23 | A | |
| 24 | A | |
| 25 | A | |
| 26 | A | |
| 27 | A | A |
| 28 | A | |
| 29 | A | A |
| 30 | A | |
| 31 | A | |
| 32 | A | |
| 33 | A | |
| 34 | A | |
| 35 | A | |
| 36 | B | |
| 37 | A | B |
| 38 | A | A |
| 39 | A | A |
| 40 | A | A |
| 41 | A | A |
| 42 | B | C |
| 43 | A | A |
| 44 | A | A |
| 45 | A | B |
| 46 | D | |
| 47 | A | A |
| 48 | D | |
| 49 | D | |
| 50 | D | |
| 51 | D | |
| 52 | A | A |
| 53 | A | B |
| 54 | A | A |
| 55 | A | A |
| 56 | D | |
| 57 | D | D |
| 58 | A | A |
| 59 | D | D |
| 60 | A | A |
| 61 | A | A |
| 62 | C | D |
| 63 | A | A |
| 64 | A | A |
| 65 | B | D |
| 66 | A | A |
| 67 | D | D |
| 68 | A | A |
| 69 | A | A |
| 70 | A | A |
| 71 | D | D |
| 72 | A | B |
| 73 | A | A |
| 74 | A | B |
| 75 | A | A |
| 76 | D | D |
| 77 | A | A |
| 78 | A | B |
| 79 | A | A |
| 80 | A | A |
| 81 | A | A |
| 82 | A | A |
| 83 | A | A |
| 84 | A | A |
| 85 | A | A |
| 86 | A | A |
| 87 | A | B |
| 88 | D | D |
| 89 | A | A |
| 90 | A | A |
| 91 | A | A |
| 92 | A | A |
| 93 | A | A |
| 94 | A | A |
| 95 | B | D |
| 96 | A | B |
| 97 | B | C |
| 98 | A | D |
| 99 | A | B |
| 100 | A | A |
| 101 | A | A |
| 102 | B | D |
| 103 | A | A |
| 104 | B | C |
| 105 | A | A |
| 106 | A | B |
| 107 | A | A |
| 108 | A | A |
| 109 | A | A |
| 110 | B | B |
| 111 | A | B |
| 112 | B | D |
| 113 | A | A |
| 114 | A | A |
| 115 | A | A |
| 116 | A | A |
| 117 | A | A |
| 118 | A | A |
| 119 | A | A |
| 120 | A | A |
| 121 | A | A |
| 122 | A | A |
| 123 | A | A |
| 124 | A | A |
| 125 | A | B |
| 126 | A | A |
| 127 | A | A |
| 128 | A | A |
| 129 | A | A |
| 130 | A | A |
| 131 | A | A |
| 132 | A | B |

TABLE A-continued

H₃ Phenoxypropylcycloamine Binding Data

| Example | Human H₃ $K_i$ nM | Rat H₃ $K_i$ nM |
|---|---|---|
| 133 | A | A |
| 134 | A | B |
| 135 | A | A |
| 136 | A | B |
| 137 | A | A |
| 138 | A | A |
| 139 | A | A |
| 140 | A | A |
| 141 | A | B |
| 142 | A | A |
| 143 | A | A |
| 144 | A | A |
| 145 | A | A |
| 146 | A | A |
| 147 | B | D |
| 148 | A | A |
| 149 | A | A |
| 150 | A | B |
| 151 | A | B |
| 152 | A | A |
| 153 | B | C |
| 154 | A | B |
| 155 | A | A |
| 156 | A | A |
| 157 | A | A |
| 158 | | |
| 159 | A | |
| 160 | A | A |
| 161 | A | |
| 162 | A | |
| 163 | A | |
| 164 | A | |
| 165 | A | A |
| 166 | A | |
| 167 | A | A |
| 168 | A | B |
| 169 | A | |
| 170 | A | |
| 171 | A | |

Binding constants ($K_i$) for Examples 1 to 171 in the Human H₃ and Rat H₃ methods described herein are expressed by letter descriptor to indicate the following ranges: A is 0.1-100 nM; B is 101-500 nM; C is 501-1000 nM; and D is >1000 nM.

Dosage and Formulation:

For therapeutic purposes, the compounds of the present invention can be administered by any means that results in the contact of the active agent with the agent's site of action in the body of the subject. The compounds may be administered by any conventional means available for use in conjunction with pharmaceuticals, either as individual therapeutic agents or in combination with other therapeutic agents, such as, for example, analgesics. The compounds of the present invention are preferably administered in therapeutically effective amounts for the treatment of the diseases and disorders described herein to a subject in need thereof.

A therapeutically effective amount can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A preferred daily dose for adult humans includes about 25, 50, 100 and 200 mg, and an equivalent dose in a human child. The compounds may be administered in one or more unit dose forms. The unit dose ranges from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The excipients are selected on the basis of the chosen route of administration and standard pharmaceutical practice, as described, for example, in *Remington: The Science and Practice of Pharmacy*, 20th ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations. Such controlled-release, or extended-release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the afore listed excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A compound of Formula I:

$$(I)$$

wherein:

$R^1$ is selected from pyrrolidin-1-yl, piperidin 1-yl, piperazin-1-yl, morpholin-4-yl, 1,3-dihydroisoindol-2-yl, hexahydro-pyrrolo[1,2-a]pyrazin-2-yl, or octahydro-pyrido[1,2-a]pyrazin-2-yl, wherein $R^1$ is optionally substituted with one to three $R^{20}$ groups;

$R^2$ at each occurrence is independently F, Cl, Br, I, $OR^{21}$, $NR^{23}R^{24}$, $NO_2$, CN, $CF_3$, $C_1$-$C_6$ alkyl, $C(=O)R^{25}$, $CO_2R^{25}$, or $C(=O)NR^{23}R^{24}$;

$R^3$ is H or $C_1$-$C_6$ alkyl;

$R^4$ is H or $C_1$-$C_6$ alkyl;

$R^5$ is wherein $R^5$ is para or meta to Y;

X is O;

Y is O;

$R^{10}$ is H, $C_1$-$C_4$ alkyl, cycloalkyl, or arylalkyl;

$R^{11}$ is H, $C_1$-$C_6$ alkyl, $C(=O)R^{25}$, $CO_2R^{25}$;

A is selected from pyrrolidin-1-yl; piperidin-1-yl; morpholin-4-yl; piperazin-1-yl; thiomorpholin-4-yl; 2,3-dihyro-indol-1-yl; 1,3-dihydro-isoindol-2-yl; 3,4-dihydro-2H-quinolin-1-yl; 3,4-dihydro-1H-isoquinolin-2-yl; 2,3,4,5-tetrahydro-benzo[b]azepin-1-yl; indol-1-yl; and benzoimidazol-1-yl;

wherein A can be optionally substituted with one to three $R^{20}$ groups;

$R^{20}$ at each occurrence is independently, F, Cl, Br, I, $OR^{21}$, $OR^{22}$, $NR^{23}R^{24}$, NHOH, $NO_2$, CN, $CF_3$, $C_1$-$C_6$ alkyl optionally substituted with $OR^{21}$, $C_2$-$C_6$ alkenyl, $C_2$-$C_6$ alkynyl, $C_3$-$C_7$ cycloalkyl, 3-7 membered heterocycloalkyl, aryl, 5 or 6 membered heteroaryl, arylalkyl, (=O), $C(=O)R^{26}$, $CO_2R^{28}$, $OC(=O)R^{25}$, $C(=O)NR^{23}R^{24}$, $NR^{27}C(=O)R^{25}$, $NR^{27}C(=O)OR^{25}$, $OC(=O)NR^{23}R^{24}$, $NR^{27}C(=S)R^{25}$, or $S(O)_qR^{25}$, wherein said aryl groups are optionally substituted with one to three $R^{30}$ groups;

$R^{21}$ at each occurrence is independently H, $C_1$-$C_6$ alkyl, aryl, or arylalkyl;

$R^{22}$ at each occurrence is independently the residue of an amino acid after the hydroxyl group of the carboxyl group is removed;

$R^{23}$ and $R^{24}$ at each occurrence are each independently selected from H, $C_1$-$C_6$ alkyl, and aryl, or $R^{23}$ and $R^{24}$, together with the nitrogen atom to which they are attached, form a 3 to 7 membered heterocyclic ring optionally substituted with =O;

$R^{25}$ at each occurrence is independently $C_1$-$C_6$ alkyl, aryl, or arylalkyl;

$R^{26}$ at each occurrence is independently $NR^{23}R^{24}$, $CF_3$, $C_1$-$C_6$ alkyl, $C_3$-$C_7$ cycloalkyl, 3-7 membered heterocycloalkyl, aryl, 5-10 membered heteroaryl, or arylalkyl, wherein said alkyl, cycloalkyl, heterocycloalkyl, aryl, and heteroaryl groups are optionally substituted with one to three $R^{30}$ groups;

$R^{27}$ at each occurrence is independently H or $C_1$-$C_6$ alkyl;

$R^{28}$ at each occurrence is independently $C_1$-$C_6$ alkyl, aryl, or arylalkyl, wherein said groups are optionally substituted with one to three $R^{30}$ groups;

$R^{30}$ at each occurrence is independently F, Cl, Br, I, $OR^{21}$, $OR^{22}$, $NR^{23}R^{24}$, NHOH, $NO_2$, CN, $CF_3$, $C_1$-$C_6$ alkyl, aryl, or arylalkyl;

n is 0, 1, 2, 3, or 4;

m is 3;

q is 0, 1, or 2;

or a stereoisomer or a pharmaceutically acceptable salt thereof.

2. The compound of claim 1 wherein $R^1$ is a pyrrolidin-1-yl, piperazin-1-yl or morpholin-4-yl group, wherein said groups are optionally substituted with 1 to 3 $R^{20}$ groups.

3. The compound of claim 2 wherein $R^1$ is a pyrrolidin-1-yl group, optionally substituted with 1 to 3 $R^{20}$ groups.

4. The compound of claim 3 wherein $R^1$ is 2-methyl-pyrrolidin-1-yl.

5. The compound of claim 1 wherein A is pyrrolidin-1-yl, piperidin-1-yl, morpholin-4-yl, piperazin-1-yl, or thiomorpholin-4-yl wherein said groups are optionally substituted with 1 to 3 $R^{20}$ groups.

6. The compound of claim 1 wherein A is 3,4-dihydro-1H-isoquinolin-2-yl; 1,3-dihydro-isoindol-2-yl; 3,4-dihydro-2H-quinolin-1-yl; 2,3,4,5-tetrahydro-benzo[b]azepin-1-yl; or 2-methyl-benzoimidazol-1-yl.

7. The compound of claim 1 wherein $R^1$ is 1,3-dihydro-isoindol-2-yl; hexahydro-pyrrolo[1,2-a]pyrazin-2-yl; or octahydro-pyrido[1,2-a]pyrazin-2-yl.

8. A compound of claim 1 having the structure of Formula Ic:

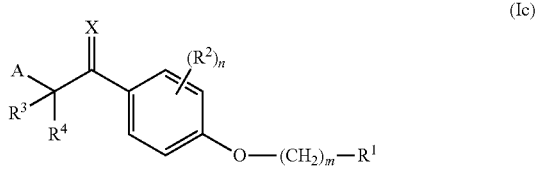

(Ic)

wherein:
$R^1$ is pyrrolidin-1-yl, piperazin-1-yl, morpholin-4-yl, 1,3-dihydroisoindol-2-yl, hexahydro-pyrrolo[1,2-a]pyrazin-2-yl, or octahydro-pyrido[1,2-a]pyrazin-2-yl, wherein $R^1$ is optionally substituted with one to three $R^{20}$ groups;
$R^2$ at each occurrence is independently F, Cl, $OR^{21}$, or $C_1$-$C_6$ alkyl;
$R^3$ is H or $C_1$-$C_6$ alkyl;
$R^4$ is H or $C_1$-$C_6$ alkyl;
X is O;
$R^{10}$ is H, $C_1$-$C_4$ alkyl, cycloalkyl, or arylalkyl;
A is selected from pyrrolidin-1-yl; piperidin-1-yl; morpholin-4-yl; piperazin-1-yl; thiomorpholin-4-yl; 1,3-dihydro-isoindol-2-yl; 3,4-dihydro-2H-quinolin-1-yl; 3,4-dihydro-1H-isoquinolin-2-yl; 2,3,4,5-tetrahydro-benzo[b]azepin-1-yl; and benzoimidazol-1-yl;
wherein A can be optionally substituted with one to three $R^{20}$ groups;
$R^{20}$ at each occurrence is independently, F, CN, $CF_3$, $C_3$-$C_6$ alkyl optionally substituted with $OR^{21}$, phenyl, 5 or 6 membered heteroaryl, (=O), C(=O)$R^{26}$, $CO_2R^{28}$, C(=O)$NR^{23}R^{24}$, or S(O)$_2R^{25}$, wherein said phenyl group is optionally substituted with one to three $R^{30}$ groups;
$R^{21}$ at each occurrence is independently H, $C_1$-$C_6$ alkyl, aryl, or arylalkyl;
$R^{23}$ and $R^{24}$ at each occurrence are each independently H or $C_1$-$C_6$ alkyl;
$R^{25}$ at each occurrence is independently $C_1$-$C_6$ alkyl, aryl, or arylalkyl;
$R^{26}$ at each occurrence is independently $NR^{23}R^{24}$, $CF_3$, $C_1$-$C_6$ alkyl, $C_3$-$C_7$ cycloalkyl, 3-7 membered heterocycloalkyl, aryl, 5-10 membered heteroaryl, or arylalkyl, wherein said alkyl, cycloalkyl, heterocycloalkyl, aryl, and heteroaryl groups are optionally substituted with one to three $R^{30}$ groups;
$R^{28}$ at each occurrence is independently $C_1$-$C_6$ alkyl, aryl, or arylalkyl, wherein said groups are optionally substituted with one to three $R^{30}$ groups;
$R^{30}$ at each occurrence is independently F, Cl, $CF_3$, $C_1$-$C_6$ alkyl or phenyl;

n is 0, 1, or 2;
m is 3; or a stereoisomer or a pharmaceutically acceptable salt thereof.

9. The compound of claim 8 wherein $R^1$ is a pyrrolidin-1-yl or group, wherein said group is optionally substituted with 1 to 3 $R^{20}$ groups.

10. The compound of claim 9 wherein A is pyrrolidin-1-yl, piperidin-1-yl, morpholin-4-yl, piperazin-1-yl, or thiomorpholin-4-yl wherein said groups are optionally substituted with 1 to 3 $R^{20}$ groups.

11. The compound of claim 8 wherein $R^1$ is pyrrolidin-1-yl, piperazin-1-yl or morpholin-4-yl and A is pyrrolidin-1-yl, piperidin-1-yl, morpholin-4-yl, piperazin-1-yl, or thiomorpholin-4-yl, wherein said $R^1$ and A are each optionally substituted with 1 to 3 $R^{20}$ groups.

12. The compound of claim 8 wherein $R^1$ is pyrrolidin-1-yl and A is pyrrolidin-1-yl, piperidin-1-yl, morpholin-4-yl, or piperazin-1-yl, wherein said $R^1$ and A are each optionally substituted with 1 to 3 $R^{20}$ groups.

13. A compound of claim 1 having the structure of Formula Id:

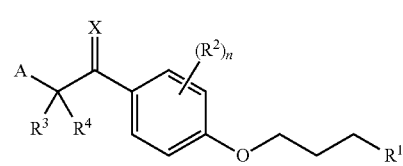

(Id)

wherein:
$R^1$ is pyrrolidin-1-yl, piperazin-1-yl, or morpholin-4-yl, wherein $R^1$ is optionally substituted with one to three $R^{20}$ groups;
$R^2$ at each occurrence is independently F, Cl, Br, I, $OR^{21}$, $NR^{23}R^{24}$, $NO_2$, CN, $CF_3$, $C_1$-$C_6$ alkyl, C(=O)$R^{25}$, $CO_2R^{25}$, or C(=O)$NR^{23}R^{24}$;
$R^3$ is H or $C_1$-$C_6$ alkyl;
$R^4$ is H or $C_1$-$C_6$ alkyl;
X is O;
$R^{10}$ is H, $C_1$-$C_4$ alkyl, cycloalkyl, or arylalkyl;
A is selected from pyrrolidin-1-yl; piperidin-1-yl; morpholin-4-yl; piperazin-1-yl; thiomorpholin-4-yl; 1,3-dihydro-isoindol-2-yl; 3,4-dihydro-2H-quinolin-1-yl; 3,4-dihydro-1H-quinolin-1-yl; 2,3,4,5-tetrahydro-benzo[b]azepin-1-yl; and benzoimadazol-1-yl;
wherein A can be optionally substituted with one to three $R^{20}$ groups;
$R^{20}$ at each occurrence is independently, F, CN, $CF_3$, $C_1$-$C_6$ alkyl optionally substituted with $OR^{21}$, phenyl, 5 or 6 membered heteroaryl, (=O), C(=O)$R^{26}$, $CO_2R^{28}$, or S(O)$_2R^{25}$, wherein said phenyl group is optionally substituted with one to three $R^{30}$ groups;
$R^{21}$ at each occurrence is independently H, $C_1$-$C_6$ alkyl, aryl, or arylalkyl;
$R^{23}$ and $R^{24}$ at each occurrence are each independently selected from H, $C_1$-$C_6$ alkyl, and aryl, or $R^{23}$ and $R^{24}$, together with the nitrogen atom to which they are attached, form a 3 to 7 membered heterocyclic ring optionally substituted with =O;
$R^{25}$ at each occurrence is independently $C_1$-$C_6$ alkyl, aryl, or arylalkyl;
$R^{26}$ at each occurrence is independently $NR^{23}R^{24}$, $CF_3$, $C_1$-$C_6$ alkyl, $C_3$-$C_7$ cycloalkyl, 3-7 membered heterocycloalkyl, aryl, 5-10 membered heteroaryl, or arylalkyl, wherein said alkyl, cycloalkyl, heterocycloalkyl, aryl, and heteroaryl groups are optionally substituted with one to three $R^{30}$ groups;

$R^{28}$ at each occurrence is independently $C_1$-$C_6$ alkyl, aryl, or arylalkyl, wherein said groups are optionally substituted with one to three $R^{30}$ groups;

$R^{30}$ at each occurrence is independently F, Cl, Br, I, $OR^{21}$, $NR^{23}R^{24}$, NHOH, $NO_2$, CN, $CF_3$, $C_1$-$C_6$ alkyl, aryl, or arylalkyl;

n is 0, 1, or 2;

or a stereoisomer or a pharmaceutically acceptable salt thereof.

14. The compound of claim 13 wherein $R^1$ is a pyrrolidin-1-yl, wherein said group is optionally substituted with 1 to 3 $R^{20}$ groups.

15. The compound of claim 13 wherein A is pyrrolidin-1-yl, piperidin-1-yl, morpholin-4-yl, piperazin-1-yl, or thiomorpholin-4-yl wherein said groups are optionally substituted with 1 to 3 $R^{20}$ groups.

16. The compound of claim 13 wherein $R^1$ is pyrrolidin-1-yl, piperazin-1-yl or morpholin-4-yl and A is pyrrolidin-1-yl, piperidin-1-yl, morpholin-4-yl, piperazin-1-yl, or thiomorpholin-4-yl, wherein said $R^1$ and A are each optionally substituted with 1 to 3 $R^{20}$ groups.

17. A compound selected from the following:

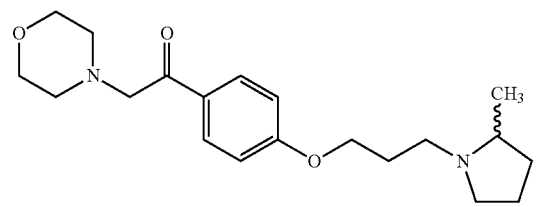 [SMILES: CC1CCCN1CCCOc1ccc(C(=O)CN2CCOCC2)cc1]

1-{4-[3-(2-Methyl-pyrrolidin-1-yl)-propoxyl]-phenyl}-2-morpholin-4-yl-ethanone

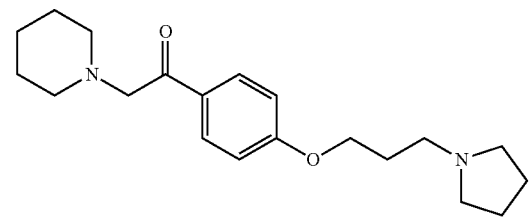 [SMILES: O=C(CN1CCCCC1)c1ccc(OCCCN2CCCC2)cc1]

2-Piperidin-1-yl-1-[4-(3-pyrrolidin-1-yl-propoxy)-phenyl]-elthanone

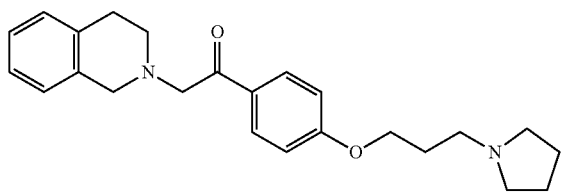 [SMILES: O=C(CN1CCc2ccccc2C1)c1ccc(OCCCN2CCCC2)cc1]

2-(3,4-Dihydro-1H-isoqunolin-2-yl)-1-[4-(3-pyrrolidin-1-yl-propoxy)-phenyl]-ethanone

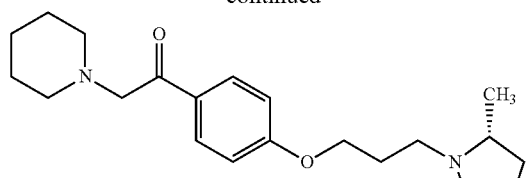

1-{4-[3-((R)-2-Methyl-pyrrolidin-1-yl)-propoxy]-phenyl}-2-piperidin-1-yl-ethanone

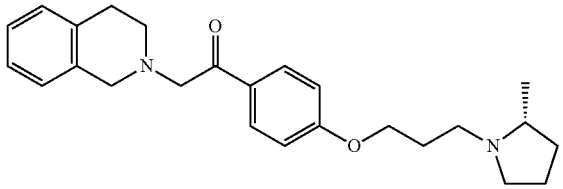 [SMILES: C[C@@H]1CCCN1CCCOc1ccc(C(=O)CN2CCc3ccccc3C2)cc1]

2-(3,4-Dihydro-1H-isoqunolin-2-yl)-1-{4-[3-((R)-2-methyl-pyrrolidin-1-yl)-propoxy]-phenyl}-ethanone

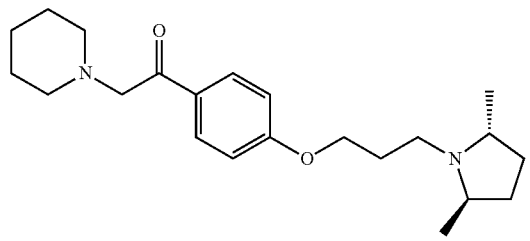 [SMILES: C[C@@H]1CC[C@@H](C)N1CCCOc1ccc(C(=O)CN2CCCCC2)cc1]

1-{4-[3-((2R,5R)-2,5-Dimethyl-pyrrolidin-1-yl)-propoxy]-phenyl}-2-piperidin-1-yl-ethanone

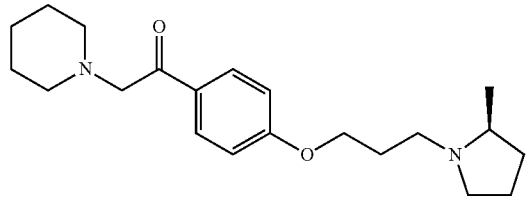 [SMILES: C[C@H]1CCCN1CCCOc1ccc(C(=O)CN2CCCCC2)cc1]

1-{4-[3-((S)-2-Methyl-pyrrolidin-1-yl)-propoxy]-phenyl}-2-piperidin-1-yl-ethanone

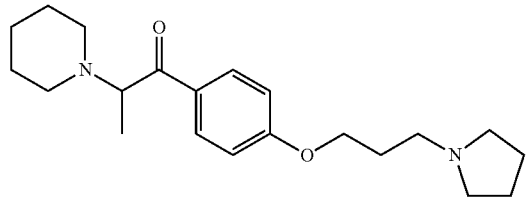 [SMILES: CC(C(=O)c1ccc(OCCCN2CCCC2)cc1)N1CCCCC1]

2-Piperidin-1-yl-1-[4-(3-pyrrolidin-1-yl-propoxy)-phenyl]-propan-1-one

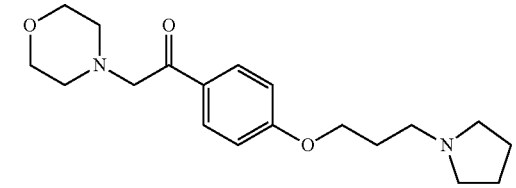 [SMILES: O=C(CN1CCOCC1)c1ccc(OCCCN2CCCC2)cc1]

2-Morpholin-4-yl-1-[4-(3-pyrrolidin-1-yl-propoxy)-phenyl]-ethanone

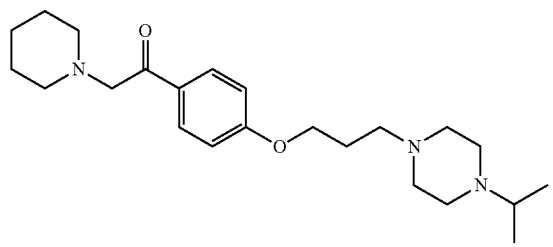 [SMILES: CC(C)N1CCN(CCCOc2ccc(C(=O)CN3CCCCC3)cc2)CC1]

1-{4-[3-(4-Isopropyl-piperazin-1-yl)-propoxy]-
phenyl}-2-piperidin-1-yl-ethanone

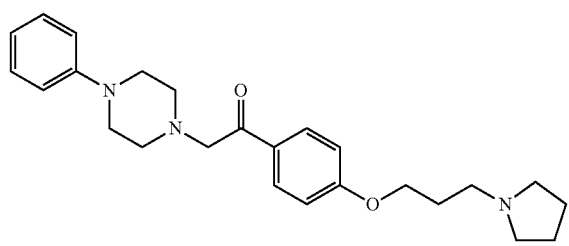 [SMILES: O=C(CN1CCN(c2ccccc2)CC1)c1ccc(OCCCN2CCCC2)cc1]

2-(4-Phenyl-piperazin-1-yl)-1-[4-(3-pyrrolidin-
1-yl-propoxyl)-phenyl]-ethanone

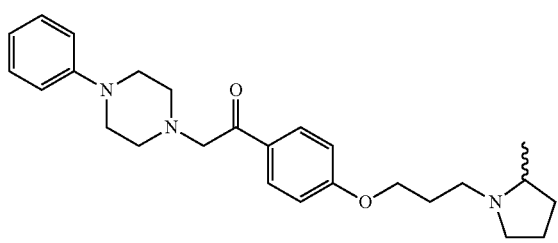 [SMILES: CC1CCCN1CCCOc1ccc(C(=O)CN2CCN(c3ccccc3)CC2)cc1]

1-{4-[3-(2-Methyl-pyrrolidin-1-yl)-propoxyl]-phenyl}-2-
(4-phenyl-piperazin-1-yl)-ethanone

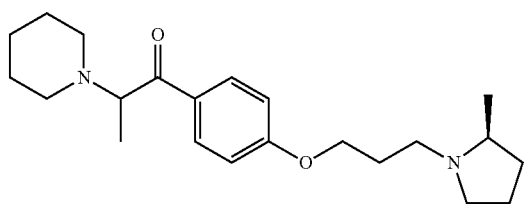 [SMILES: CC(C(=O)c1ccc(OCCCN2CCC[C@@H]2C)cc1)N1CCCCC1]

1-{4-[3-((S)-2-Methyl-pyrrolidin-1-yl)-propoxyl]-
phenyl}-2-piperidin-1-yl-propan-1-one

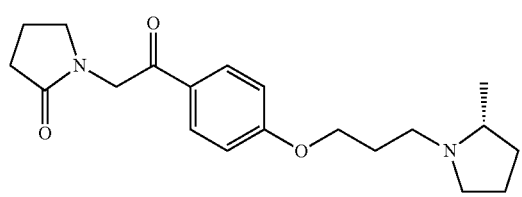 [SMILES: C[C@@H]1CCCN1CCCOc1ccc(C(=O)CN2CCCC2=O)cc1]

1-(2-{4-[3-((R)-2-Methyl-pyrrolidin-1-yl)-propoxy]-
phenyl}-2-oxo-ethyl)-pyrrolidin-2-one

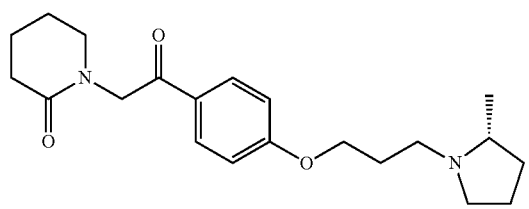 [SMILES: C[C@@H]1CCCN1CCCOc1ccc(C(=O)CN2CCCCC2=O)cc1]

1-(2-{4-[3-((R)-2-Methyl-pyrrolidin-1-yl)-propoxy]-
phenyl}-2-oxo-ethyl)-piperidin-2-one

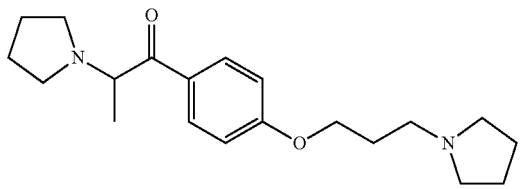 [SMILES: CC(C(=O)c1ccc(OCCCN2CCCC2)cc1)N1CCCC1]

2-Pyrrolidin-1-yl-1-[4-(3-pyrrolidin-1-yl-
propoxy)-phenyl]-propan-1-one

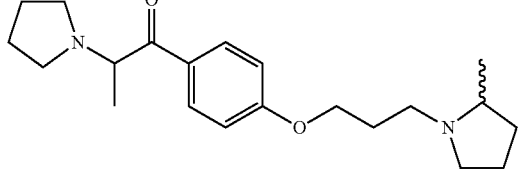

1-{4-[3-(2-Methyl-pyrrolidin-1-yl)-propoxy]-
phenyl}-2-pyrrolidin-1-yl-propan-1-one

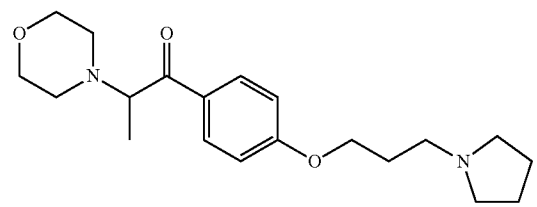 [SMILES: CC(C(=O)c1ccc(OCCCN2CCCC2)cc1)N1CCOCC1]

2-Morpholin-4-yl-1-[4-(3-pyrrolidin-
1-yl-propoxy)-phenyl]-propan-1-one

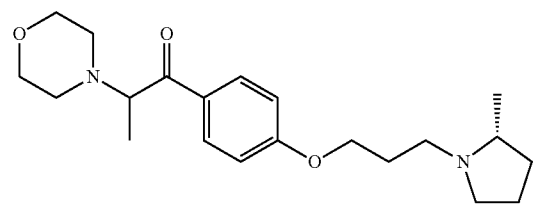

1-{4-[3-(2-Methyl-pyrrolidin-1-yl)-propoxy}-
phenyl}-2-morpholin-4-yl-propan-1-one

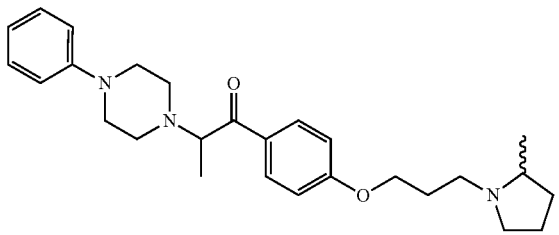 [SMILES: CC1CCCN1CCCOc1ccc(C(=O)C(C)N2CCN(c3ccccc3)CC2)cc1]

1-{4-[3-(2-Methyl-pyrrolidin-1-yl)-propoxy]-phenyl}-
2-(4-phenyl-piperazin-1-yl)-propan-1-one

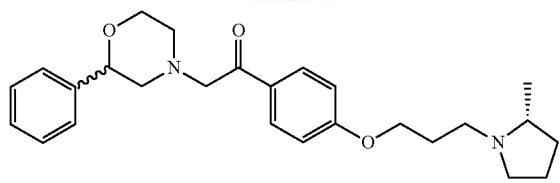 [SMILES: C[C@@H]1CCCN1CCCOc1ccc(C(=O)CN2CCOC(c3ccccc3)C2)cc1]

1-{4-[3-((R)-2-Methyl-pyrrolidin-1-yl-propoxy]-
phenyl}-2-(2-phenyl-morpholin-4-yl)-ethanone

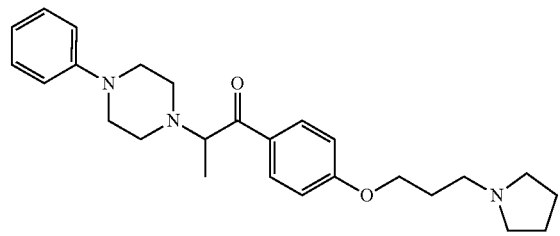 [SMILES: CC(C(=O)c1ccc(OCCCN2CCCC2)cc1)N1CCN(c2ccccc2)CC1]

2-(4-Phenyl-piperazin-1-yl)-1-[4-(3-pyrrolidin-1-yl-
propoxy)-phenyl]-propan-1-one

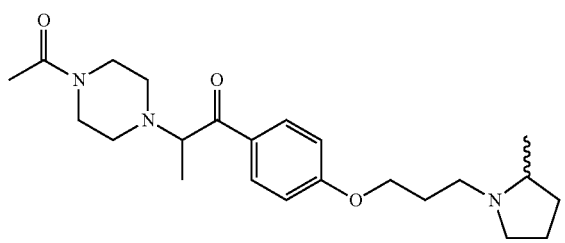 [SMILES: CC(=O)N1CCN(C(C)C(=O)c2ccc(OCCCN3CCCC3C)cc2)CC1]

2-(4-Acetyl-piperazin-1-yl)-1-{4-[3-(2-methyl-
pyrrolidin-1-yl)-propoxy]-phenyl}-propan-1-one

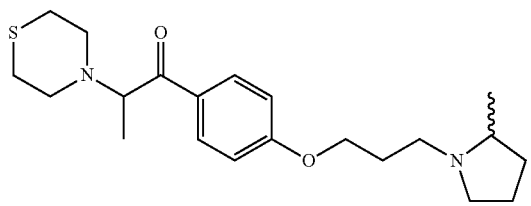 [SMILES: CC1CCCN1CCCOc1ccc(C(=O)C(C)N2CCSCC2)cc1]

1-{4-[3-(2-Methyl-pyrrolidin-1-yl)-propoxy]-
phenyl}-thiomorpholin-4-yl-propan-1-one

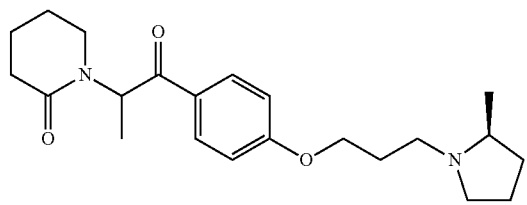 [SMILES: CC(C(=O)c1ccc(OCCCN2CCC[C@@H]2C)cc1)N1CCCCC1=O]

1-(1-Methyl-2-{4-[3-((S)-2-methyl-pyrrolidin-1-yl)-
propoxy]-phenyl}-2-oxo-ethyl)-piperidin-2-one

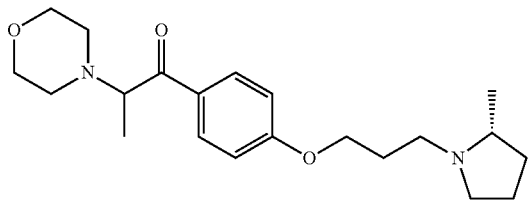 [SMILES: CC(C(=O)c1ccc(OCCCN2CCC[C@H]2C)cc1)N1CCOCC1]

1-{4-[3-((R)-2-Methyl-pyrrolidin-1-yl)-propoxy]-
phenyl]-2-morpholin-4-yl-propan-1-one

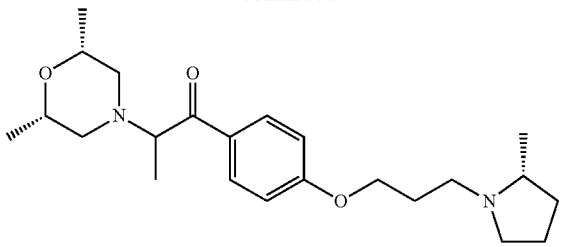 [SMILES: C[C@@H]1CN(CC(=O)c2ccc(OCCCN3CCC[C@H]3C)cc2)C[C@H](C)O1]

2-((2R,6S)-2,6-Dimethyl-morpholin-4-yl)-1-{4-[3-((R)-2-
methyl-pyrrolidin-1-yl)-propoxy]-phenyl}-ethanone

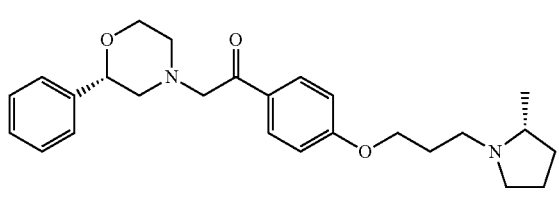 [SMILES: C[C@@H]1CCCN1CCCOc1ccc(C(=O)CN2CCO[C@@H](c3ccccc3)C2)cc1]

1-{4-[3-((R)-2-Methyl-pyrrolidin-1-yl)propoxy]-phenyl}-
2-((S)-2-phenyl-morpholin-4-yl)-ethanone

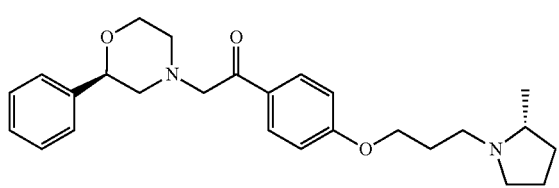 [SMILES: C[C@@H]1CCCN1CCCOc1ccc(C(=O)CN2CCO[C@H](c3ccccc3)C2)cc1]

1{4-[3-((R)-2-Methyl-pyrrolidin-1-yl)-propoxy]-
phenyl}-2-((R)-2-phenyl-morpholin-4-yl)-ethanone

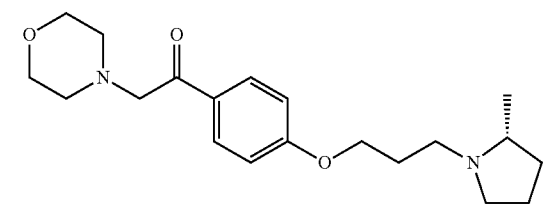 [SMILES: C[C@@H]1CCCN1CCCOc1ccc(C(=O)CN2CCOCC2)cc1]

1-{4-[3-((R)-2-Methyl-pyrrolidin-1-yl)-propoxy]-
phenyl}-2-morpholin-4-yl)-ethanone

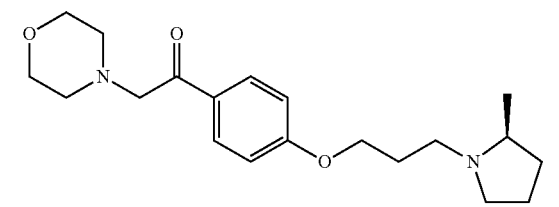

1-{4-[3-((S)-2-Methyl-pyrrolidin-1-yl)-propoxy]-
phenyl}-2-morpholin-4-yl)-ethanone

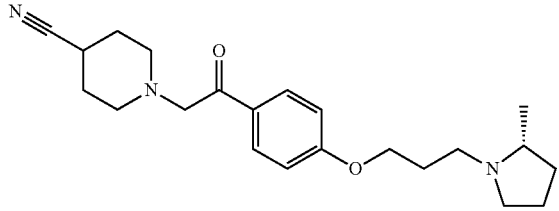 [SMILES: C[C@@H]1CCCN1CCCOc1ccc(C(=O)CN2CCC(C#N)CC2)cc1]

1-(2-{4-[3-((R)-2-Methyl-pyrrolidin-1-yl)-propoxy]-
phenyl}-2-oxo-ethyl)-piperidine-4-carbonitrile

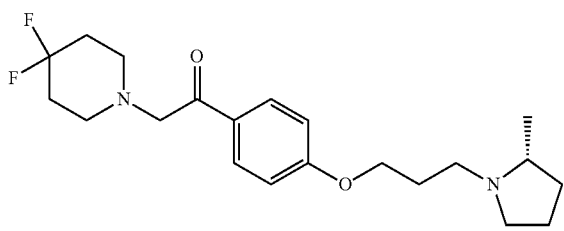

2-(4,4-Difluoro-piperidin-1-yl)-1-{4-[3-((R)-2-methyl-pyrrolidin-1-yl)-propoxy]-phenyl}-ethanone

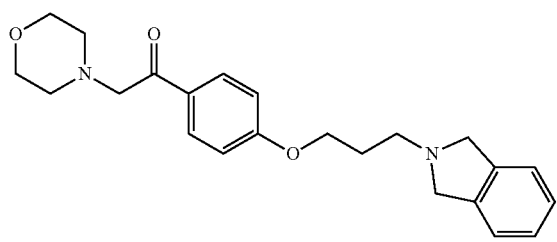 [SMILES: O=C(CN1CCOCC1)c1ccc(OCCCN2Cc3ccccc3C2)cc1]

1-{4-[3-(1,3-Dihydro-isoindol-2-yl)-propoxy]-phenyl}-2-morpholin-4-yl-ethanone

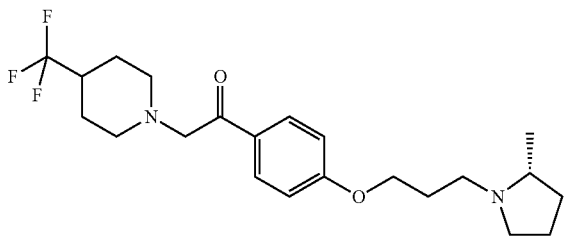 [SMILES: C[C@@H]1CCCN1CCCOc1ccc(C(=O)CN2CCC(C(F)(F)F)CC2)cc1]

1-{4-[3-((R)-2-Methyl-pyrrolidin-1-yl)-propoxy]-phenyl}-2-(4-trifluoro methyl-piperidin-1-yl)-ethanone

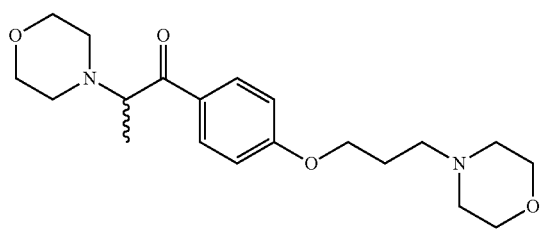 [SMILES: CC(C(=O)c1ccc(OCCCN2CCOCC2)cc1)N1CCOCC1]

2-Morpholin-4-yl-1-[4-(3-morpholin-4-yl-propoxy)-phenyl]-propan-1-one

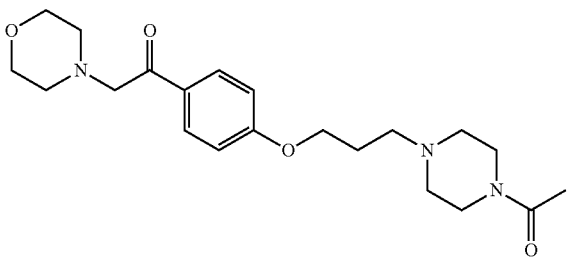 [SMILES: CC(=O)N1CCN(CCCOc2ccc(C(=O)CN3CCOCC3)cc2)CC1]

1-{4-[3-(4-Acetyl-piperazin-1-yl)-propoxy]-phenyl}-2-morpholin-4-yl-ethanone

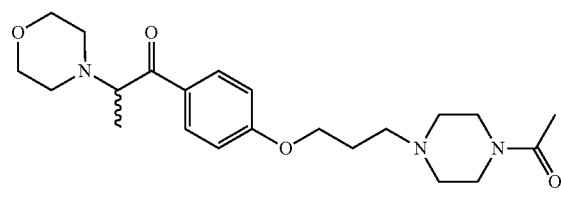 [SMILES: CC(=O)N1CCN(CCCOc2ccc(C(=O)C(C)N3CCOCC3)cc2)CC1]

1-{4-[3-(4-Acetyl-piperazin-1-yl)-propoxy]-phenyl}-2-morpholin-4-yl-propan-1-one

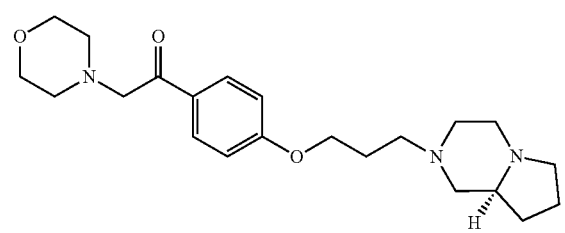

1-{4-[(S)-3-(Hezahydro-pyrrolo[1,2-a]pyrazin-2-yl)-propoxy]-phenyl}-2-morpholin-4-yl-ethanone

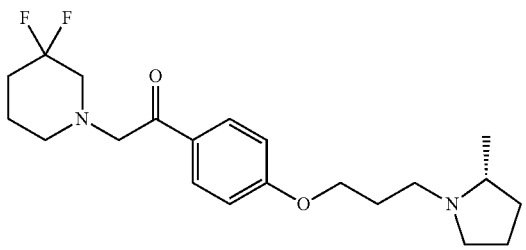 [SMILES: C[C@@H]1CCCN1CCCOc1ccc(C(=O)CN2CCCC(F)(F)C2)cc1]

2-(3,3-Difluoro-piperidin-1-yl)-1-{4-[3-((R)-2-methyl-pyrrolidin-1-yl)-propoxy]-phenyl}-ethanone

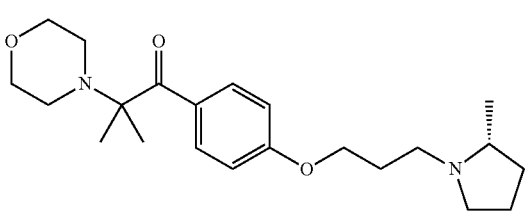 [SMILES: C[C@@H]1CCCN1CCCOc1ccc(C(=O)C(C)(C)N2CCOCC2)cc1]

2-Methyl-1-{4-[3-((R)-2-methyl-pyrrolidin-1-yl)-propoxy]-phenyl}-2-morpholin-4-yl-propan-1-one

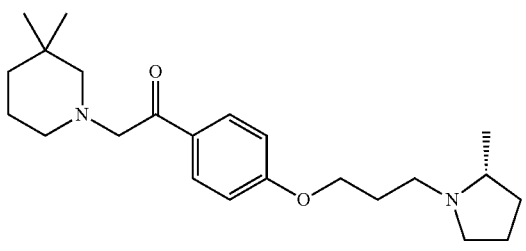 [SMILES: C[C@@H]1CCCN1CCCOc1ccc(C(=O)CN2CCCC(C)(C)C2)cc1]

2-(3,3-Dimethyl-piperidin-1-yl)-1-{4-[3-((R)-2-methyl-pyrrolidin-1-yl)-propoxy]-phenyl}-ethanone

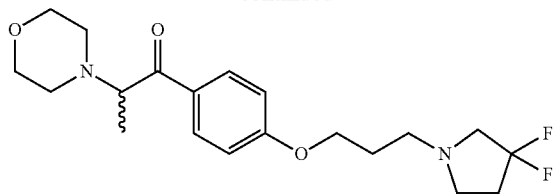 [SMILES: CC(C(=O)c1ccc(OCCCN2CCC(F)(F)C2)cc1)N1CCOCC1]

1-{4-[3-(3,3-Difluoro-pyrrolidin-1-yl)-propoxy]-
phenyl}-2-morpholin-4-yl-propan-1-one

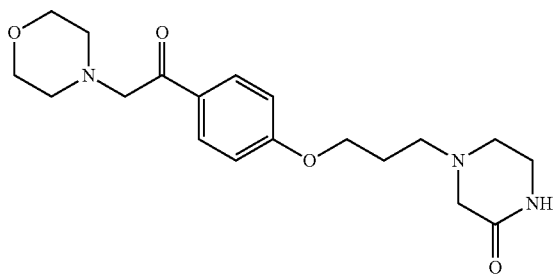 [SMILES: O=C1CN(CCCOc2ccc(C(=O)CN3CCOCC3)cc2)CCN1]

4-{3-[4-(2-Morpholin-4-yl)-acetyl)-
phenoxy]-propyl}-piperazin-2-one

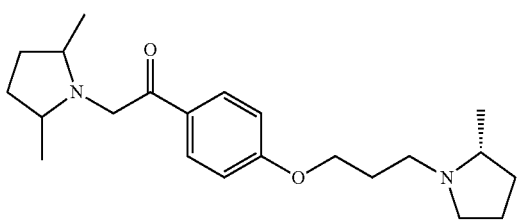 [SMILES: CC1CCC(C)N1CC(=O)c1ccc(OCCCN2CCC[C@H]2C)cc1]

2-(2,5-Dimethyl-pyrrolidin-1-yl)-1-{4-[3((R)-2-methyl
pyrrolidin-1-yl)-propoxy]-phenyl}-ethanone

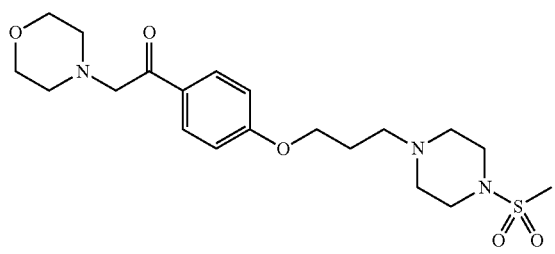 [SMILES: CS(=O)(=O)N1CCN(CCCOc2ccc(C(=O)CN3CCOCC3)cc2)CC1]

1-{4-[3-(4-Methanesulfonyl-piperazin-1-yl)-propoxy]-
phenyl}-2-morpholin-4-yl-ethanone

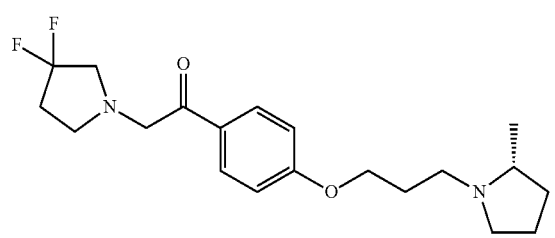 [SMILES: C[C@@H]1CCCN1CCCOc1ccc(C(=O)CN2CCC(F)(F)C2)cc1]

2-(3,3-Difluoro-pyrrolidin-1-yl)-1-{4-[3((R)-
methyl-pyrrolidin-1-yl)-propoxy]-phenyl}-ethanone

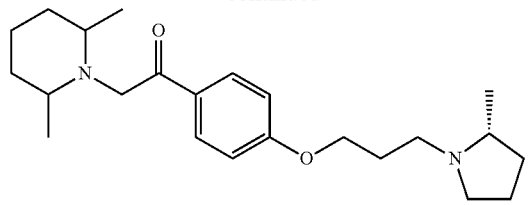 [SMILES: CC1CCCC(C)N1CC(=O)c1ccc(OCCCN2CCC[C@H]2C)cc1]

2-(2,6-Dimethyl-piperidin-1-yl)-1-{4-[3-((R)-2-methyl-
pyrrolidin-1-yl)-propoxy]-phenyl}-ethanone

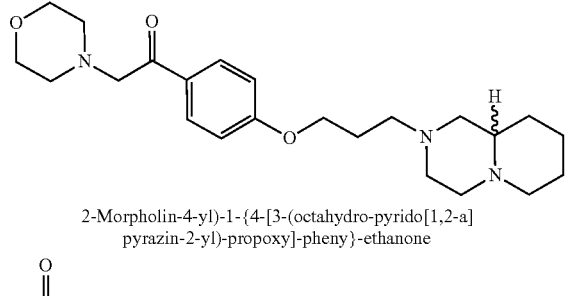

2-Morpholin-4-yl)-1-{4-[3-(octahydro-pyrido[1,2-a]
pyrazin-2-yl)-propoxy]-pheny}-ethanone

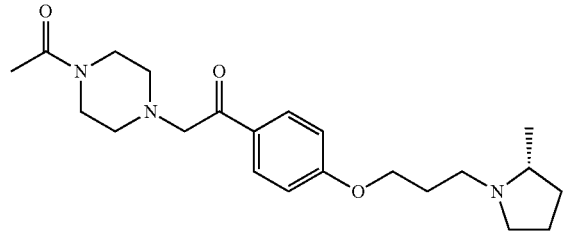 [SMILES: CC(=O)N1CCN(CC(=O)c2ccc(OCCCN3CCC[C@H]3C)cc2)CC1]

2-(4-Acetyl-piperazin-1-yl)-1-{4-{3-((R)-2-methyl-
pyrrolidin-1-yl)-propoxy]-phenyl}-ethanone

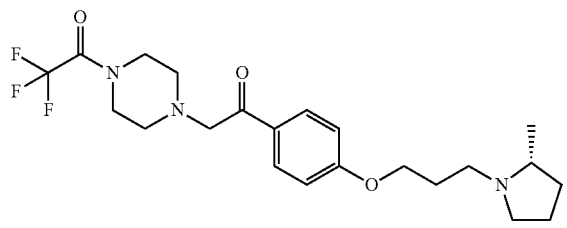 [SMILES: C[C@@H]1CCCN1CCCOc1ccc(C(=O)CN2CCN(C(=O)C(F)(F)F)CC2)cc1]

2,2,2-Trifluoro-1-[4-(2-{4-[3-((R)-2-methyl-pyrrolidin-1-yl)-
propoxy]-phenyl}-2-oxo-ethyl)-piperazin-1-yl]-ethanone

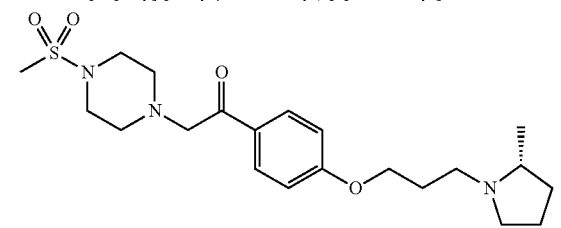

2-(4-Methanesulfonyl-piperazin-1-yl)-1-{4-[3-((R)-2-
methyl-pyrrolidin-1-yl)-propoxy]-phenyl}-ethanone

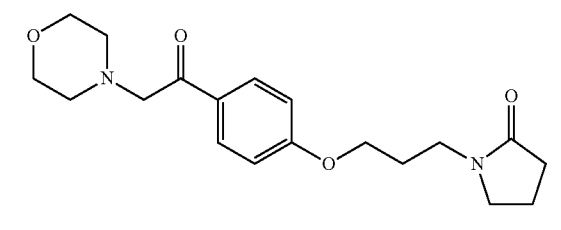 [SMILES: O=C(CN1CCOCC1)c1ccc(OCCCN2CCCC2=O)cc1]

1-{3-[4-(2-Morpholin-4-yl)-acetyl)-
phenoxy]-propyl}-pyrrolidin-2-one

-continued

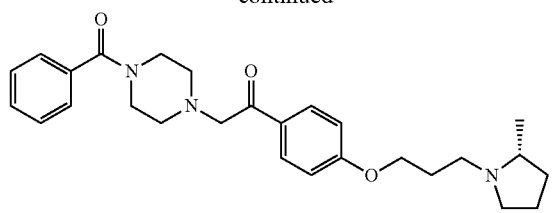

2-(4-Benzoyl-piperazin-1-yl)-1-{4-[3-((R)-2-methyl-pyrrolidin-1-yl)-propoxy]-phenyl}-ethanone

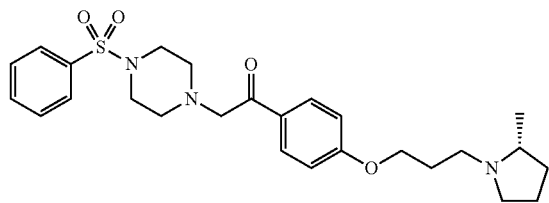 [SMILES: C[C@@H]1CCCN1CCCOc1ccc(C(=O)CN2CCN(S(=O)(=O)c3ccccc3)CC2)cc1]

2-(4-Benzenesulfonyl-piperazin-1-yl)-1-{4-[3-((R)-2-methyl-pyrrolidin-1-yl)-propoxy]-phenyl}-ethanone

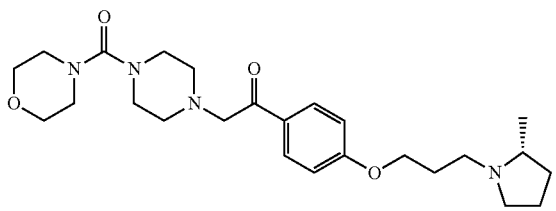

1-{4-[3-((R)-2-Methyl-pyrrolidin-1-yl)-propoxy]-phenyl}-2-[4-(morpholine-4-carbonyl)-piperazin-1-yl]-ethanone

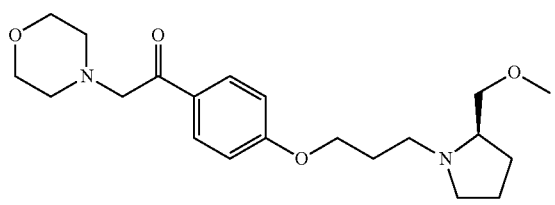 [SMILES: COC[C@H]1CCCN1CCCOc1ccc(C(=O)CN2CCOCC2)cc1]

1-{4-[3-((R)-2-Methoxymethyl-pyrrolidin-1-yl)-propoxy}-phenyl}-2-morpholin-4-yl-ethanone

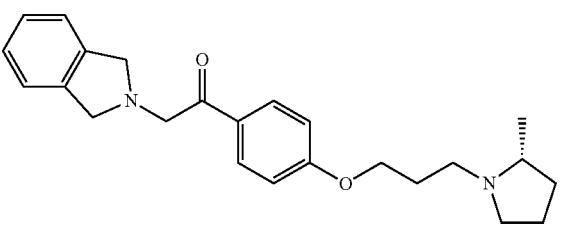 [SMILES: C[C@@H]1CCCN1CCCOc1ccc(C(=O)CN2Cc3ccccc3C2)cc1]

2-(1,3-Dihydro-isoindol-2-yl)-1-{4-[3-((R)-2-methyl-pyrrolidin-1-yl)-propoxy}-phenyl}-ethanone

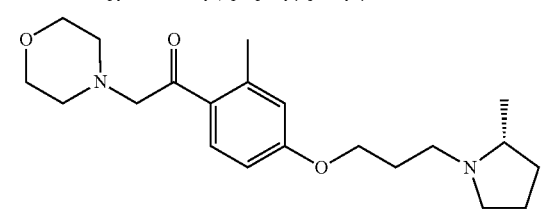

1-{2-Methyl-4-[3-((R)-2-methyl-pyrrolidin-1-yl)-propoxy}-phenyl}-2-morpholin-4-yl-ethanone -continued

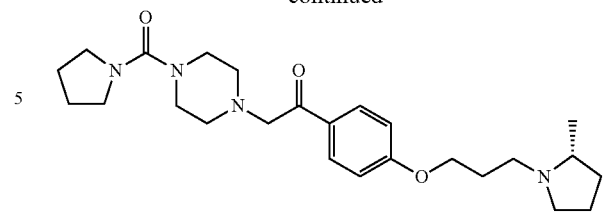

1-{4-[3-((R)-2-Methyl-pyrrolidin-1-yl)propoxy]-phenyl}-2-[4-(pyrrolidine-1-carbonyl)-piperazin-1-yl]ethanone

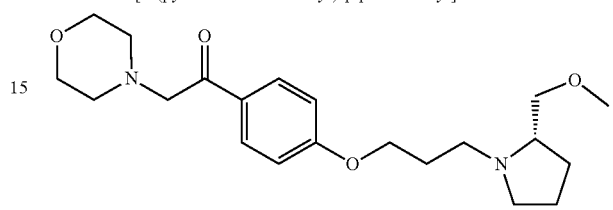

1-{4-[3-((S)-2-Methoxymethyl-pyrrolidin-1-yl)-propoxy]-phenyl}-2-morpholin-4-yl-ethanone

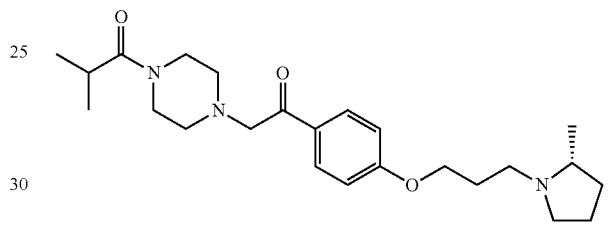

2-Methyl-1-[4-(2-{4-[3-((R)-2-methyl-pyrrolidin-1-yl)-propoxy}-phenyl}-2-oxo-ethyl)-piperazin-1-yl]-propan-1-one

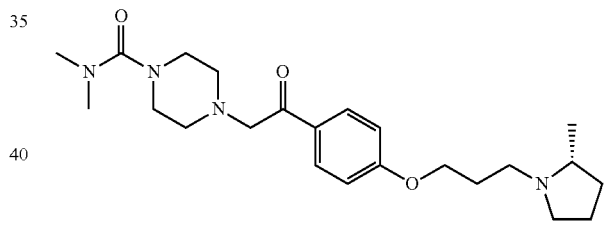

4-(2-{4-[3-((R)-2-Methyl-pyrrolidin-1-yl)-propoxy]-phenyl}-2-oxo-ethyl)-piperazine-1-carboxylic acid dimethylamide

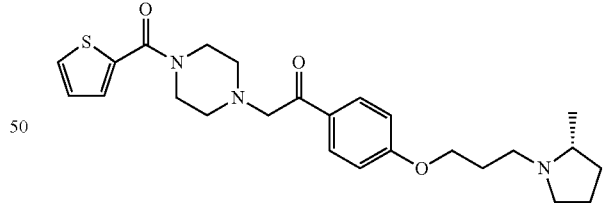

1-{4-[3-((R)-2-Methyl-pyrrolidin-1-yl)-propoxy]-phenyl}-2-[4-(thiophene-2-carbonyl)-piperazin-1-yl]-ethanone

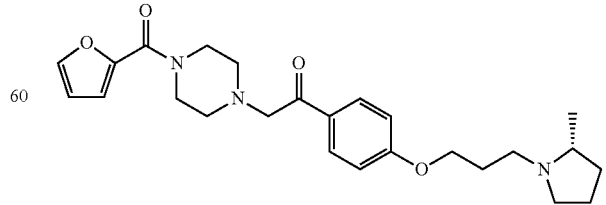

2-[4-(Furan-2-carbonyl)-piperazin-1-yl]-1-{4-[3-((R)-2-methyl-pyrrolidin-1-yl)-propoxy]-phenyl}-ethanone

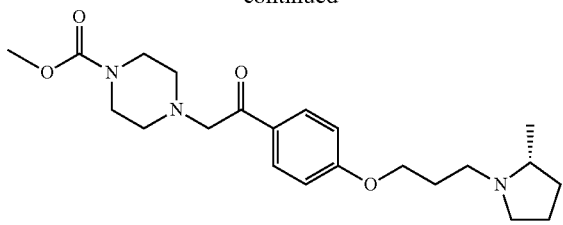

4-(2-{4-[3-((R)-2-Mehtyl-pyrrolidin-1-yl)-propoxy]-phenyl}-2-oxo-ethyl)-piperazine-1-carboxylic acid methyl ester

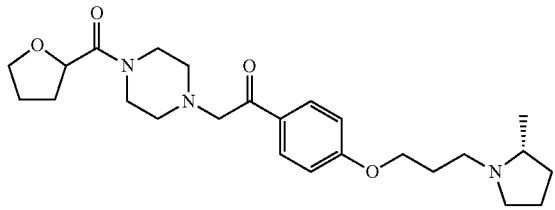 [SMILES: C[C@@H]1CCCN1CCCOc1ccc(C(=O)CN2CCN(C(=O)N3CCCC3)CC2)cc1]

1-{4-[3-((R)-2-Mehtyl-pyrrolidin-1-yl)-propoxy]-phenyl}-2-[4-(tetrahydro-furan-2-carbonyl)-piperazin-1-yl]-ethanone

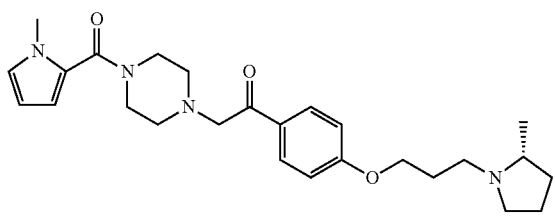 [SMILES: C[C@@H]1CCCN1CCCOc1ccc(C(=O)CN2CCN(C(=O)c3cccn3C)CC2)cc1]

2-[4-(1-Methyl-1H-pyrrole-2-carbonyl)-piperazin-1-yl]-1-{4-[3-((R)-2-methyl-pyrrolidin-1-yl)-propoxy]-phenyl}-ethanone

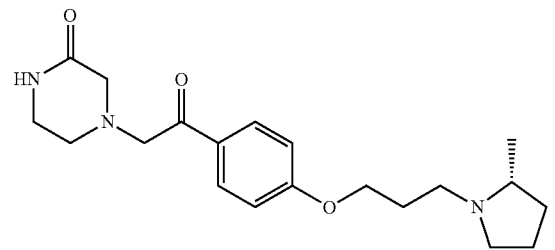 [SMILES: C[C@@H]1CCCN1CCCOc1ccc(C(=O)CN2CCNC(=O)C2)cc1]

4-(2-{4-[3-((R)-2-Methyl-pyrrolidin-1-yl)-propoxy]-phenyl}-2-oxo-ethyl)-piperazin-2-one

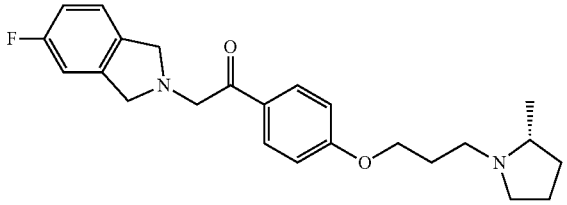

2-(5-Fluoro-1,3-dihydro-isoindol-2-yl)-1-{4-[3-((R)-2-methyl-pyrrolidin-1-yl)-propoxy]-phenyl}-ethanone

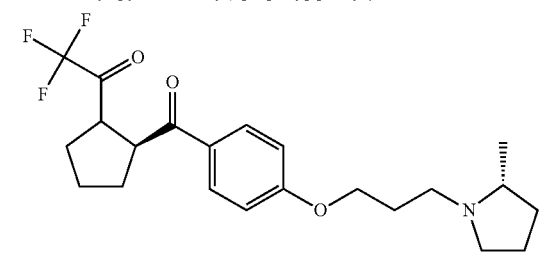

2,2,2-Trifluoro-1-((R)-2-{4-[3((R)-2-methyl-pyrrolidin-1-yl)-propoxy]-benzoyl}-pyrrolidin-1-yl)-ethanone

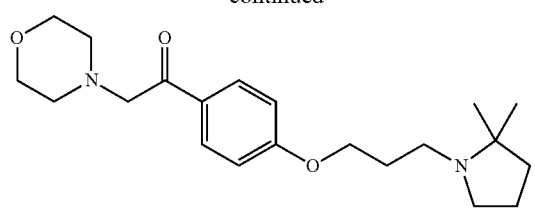

1-{4-[3-(2,2-Dimethyl-pyrrolidin-1-yl)-propoxy}-phenyl}-2-morpholin-4-yl-ethanone

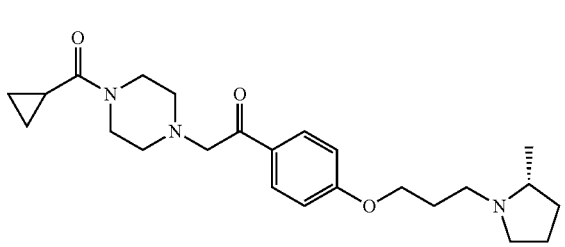 [SMILES: C[C@@H]1CCCN1CCCOc1ccc(C(=O)CN2CCN(C(=O)C3CC3)CC2)cc1]

2-(4-Cyclopropanecarbonyl-piperazin-1-yl)-1-{4-[3-((R)-2-methyl-pyrrolidin-1-yl)-propoxy]-phenyl}-ethanone

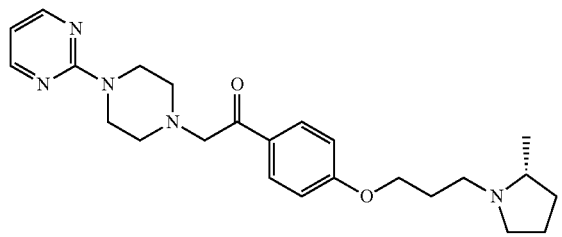 [SMILES: C[C@@H]1CCCN1CCCOc1ccc(C(=O)CN2CCN(c3ncccn3)CC2)cc1]

1-{4-[3-((R)-2-Methyl-pyrrolidin-1-yl)-propoxy}-phenyl}-2-(4-pyrimidin-2-yl-piperazin-1-yl)-ethanone

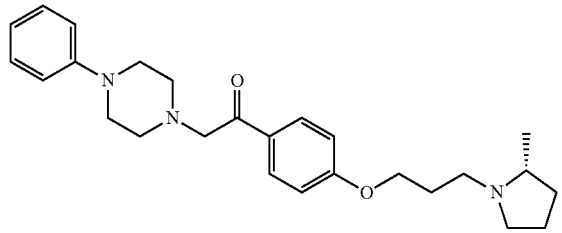 [SMILES: C[C@@H]1CCCN1CCCOc1ccc(C(=O)CN2CCN(c3ccccc3)CC2)cc1]

1{4-[3-((R)-2-Methyl-pyrrolidin-1-yl)-propoxy]-phenyl}-2-(4-phenyl-piperazin-1-yl)-ethanone

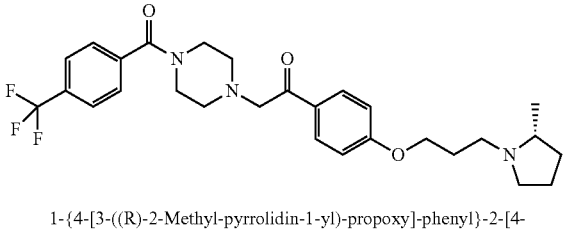

1-{4-[3-((R)-2-Methyl-pyrrolidin-1-yl)-propoxy]-phenyl}-2-[4-(4-trifluoromethyl-benzoyl)-piperazin-1-yl]-ethanone

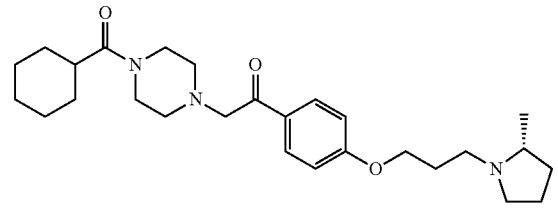 [SMILES: C[C@@H]1CCCN1CCCOc1ccc(C(=O)CN2CCN(C(=O)C3CCCCC3)CC2)cc1]

2-(4-Cyclohexanecarbonyl-piperazin-1-yl)-1-{4-[3-((R)-2-methyl-pyrrolidin-1-yl)-propoxy]-phenyl}-ethanone

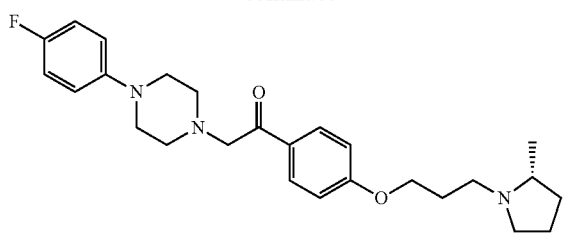 [SMILES: C[C@@H]1CCCN1CCCOc1ccc(C(=O)CN2CCN(c3ccc(F)cc3)CC2)cc1]

2-[4-(4-Fluoro-phenyl)-piperazin-1-yl]-1-{4-[3-((R)-2-methyl-pyrrolidin-1-yl)-propoxy]-phenyl}-ethanone

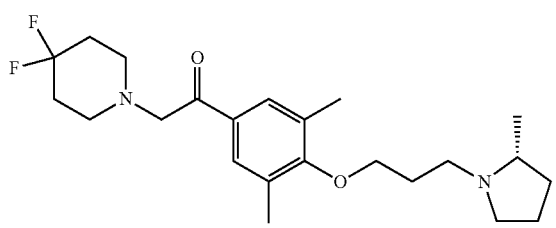

2-(4,4-Difluoro-piperidin-1-yl)-1-{3,5-dimethyl-4-[3-((R)-2-methyl-pyrolidin-1-yl)-propoxy}-phenyl}-ethanone

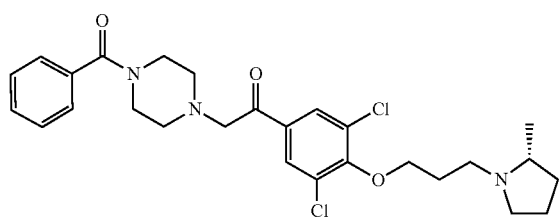

2-(4-Benzoyl-piperazin-1-yl)-1-{3,5-dichloro-4-[3-((R)-2-methyl-pyrrolidin-1-yl)-propoxy}-phenyl}-ethanone

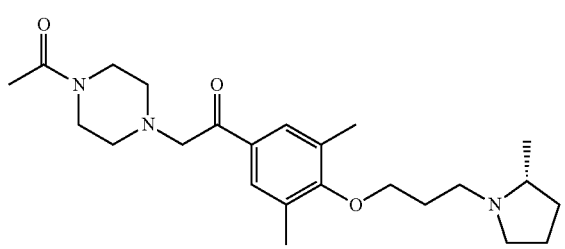 [SMILES: CC(=O)N1CCN(CC(=O)c2cc(C)c(OCCCN3CCC[C@H]3C)c(C)c2)CC1]

2-(4-Acetyl-piperazin-1-yl)-1-{3,5-dimethyl-4-[3-((R)-2-methyl-pyrrolidin-1-yl)-propoxy]-phenyl}-ethanone

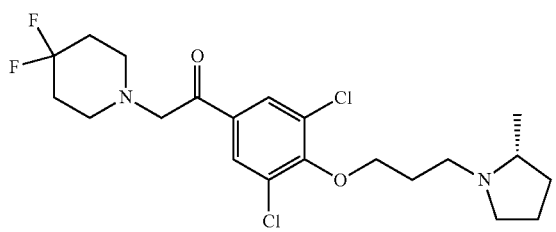 [SMILES: C[C@@H]1CCCN1CCCOc1c(Cl)cc(C(=O)CN2CCC(F)(F)CC2)cc1Cl]

1-{3,5-Dichloro-4-[3-((R)-2-methyl-pyrrolidin-1-yl)-propoxy]-phenyl}-2-(4,4-difluoro-piperidin-1-yl)-ethanone

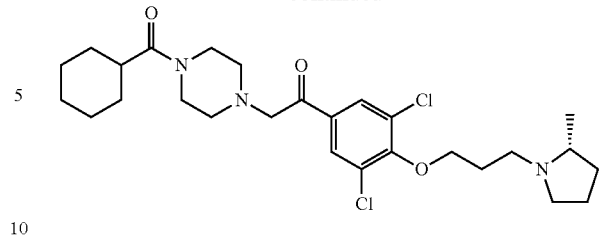

2-(4-Cyclohexanecarbonyl-piperazin-1-yl)-1-{3,5-dichloro-4-[3-((R)-2-methyl-pyrrolidin-1-yl)propoxy]-phenyl}-ethanone

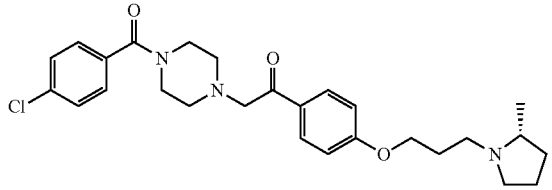 [SMILES: C[C@@H]1CCCN1CCCOc1ccc(C(=O)CN2CCN(C(=O)c3ccc(Cl)cc3)CC2)cc1]

2-[4-(4-Chloro-benzoyl)-piperazin-1-yl]-1-{4-[3-((R)-2-methyl-pyrrolidin-1-yl)-propoxy]-phenyl}-ethanone

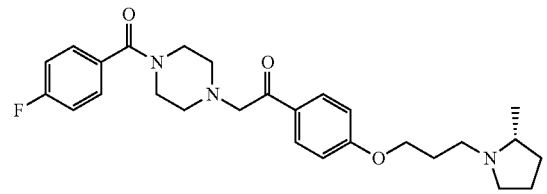 [SMILES: C[C@@H]1CCCN1CCCOc1ccc(C(=O)CN2CCN(C(=O)c3ccc(F)cc3)CC2)cc1]

2-[4-(4-Fluoro-benzoyl)-piperazin-1-yl]-1-{4-[3-((R)-2-methyl-pyrrolidin-1-yl)-propoxy]-phenyl}-ethanone

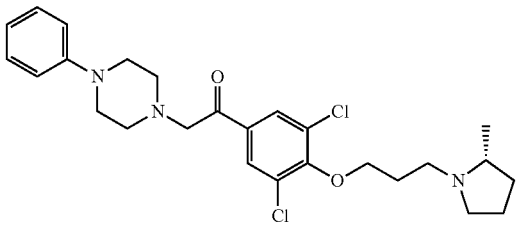 [SMILES: C[C@@H]1CCCN1CCCOc1c(Cl)cc(C(=O)CN2CCN(c3ccccc3)CC2)cc1Cl]

1-{3,5-Dichloro-4-[3-((R)-2-methyl-pyrrolidin-1-yl)-propoxy}-phenyl}-2-(4-phenyl-piperazin-1-yl)-ethanone

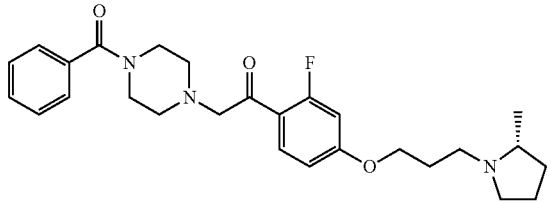

2-(4-Benzoyl-piperazin-1-yl)-1-{2-fluoro-4-[3-((R)-2-methyl-pyrrolidin-1-yl-propoxy]-phenyl}-ethanone

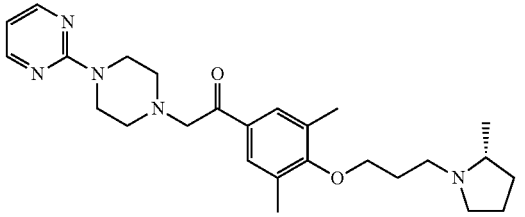 [SMILES: Cc1cc(C(=O)CN2CCN(c3ncccn3)CC2)cc(C)c1OCCCN1CCC[C@H]1C]

1-{3,5-Dimethyl-4-[3-((R)-2-methyl-pyrrolidin-1-yl)-propoxy]-phenyl}-2-(4-pyrimidin-2-yl-piperazin-1-yl)-ethanone

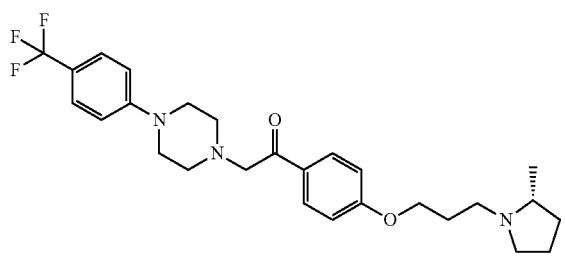 [SMILES: C[C@@H]1CCCN1CCCOc1ccc(C(=O)CN2CCN(c3ccc(C(F)(F)F)cc3)CC2)cc1]

1-{4-[3-((R)-2-Methyl-pyrrolidin-1-yl)-propoxy]-phenyl}-2-[4-(4-trifluoromethyl-phenyl)-piperazin-1-yl]-ethanone

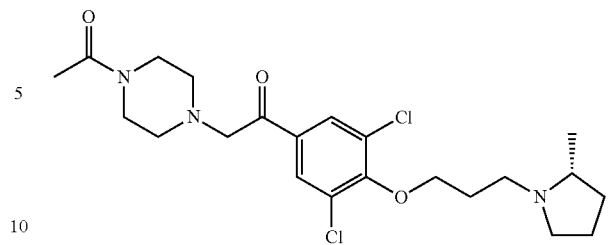

2-(4-Acetyl-piperazin-1-yl)-1-{3-5-dichloro-4-[3-((R)-2-methyl-pyrrolidin-1-yl)-propoxy]-phenyl}-ethanone

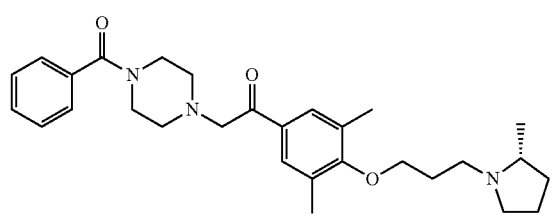 [SMILES: Cc1cc(C(=O)CN2CCN(C(=O)c3ccccc3)CC2)cc(C)c1OCCCN1CCC[C@H]1C]

2-(4-Benzoyl-piperazin-1-yl)-1-{3,5-dimethyl-4-[3-((R)-2-methyl-pyrrolidin-1-yl)-propoxy]-phenyl}-ethanone

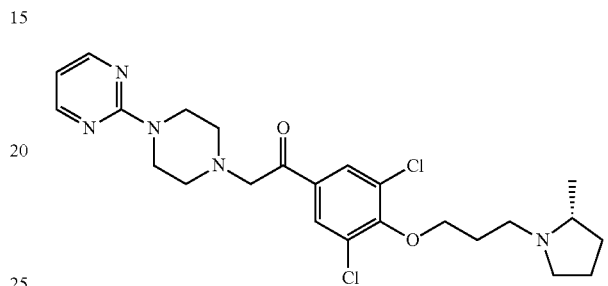

1-{3,5-Dichloro-4-[3-((R)-2-methyl-pyrrolidin-1-yl)-propoxy]-phenyl}-2-(4-pyrimidin-2-yl-piperazin-1-yl)-ethanone

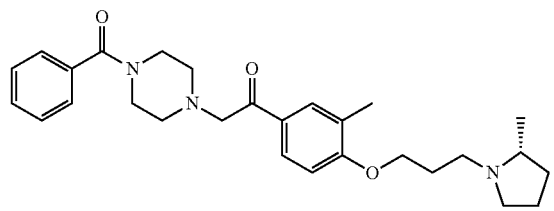

2-(4-Benzoyl-piperazin-1-yl)-1-{3,methyl-4-[3-((R)-2-methyl-pyrrolidin-1-yl)-propoxy]-phenyl}-ethanone

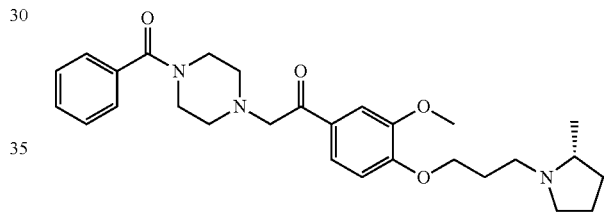

2-(4-Benzoyl-piperazin-1-yl)-1-{3-methoxy-4-[3-((R)-2-methyl-pyrrolidin-1-yl)-propoxy}-phenyl}-ethanone

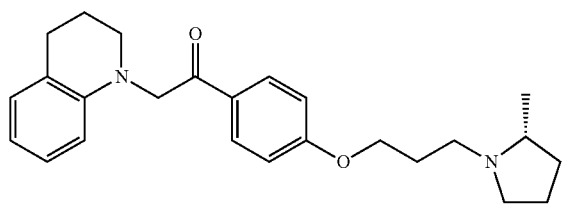 [SMILES: C[C@@H]1CCCN1CCCOc1ccc(C(=O)CN2CCCc3ccccc32)cc1]

2-(3,4-Dihydro-2H-quinolin-1-yl)-1-{4-[3-((R)-2-methyl-pyrrolidin-1-yl)-propoxy]-phenyl}-ethanone

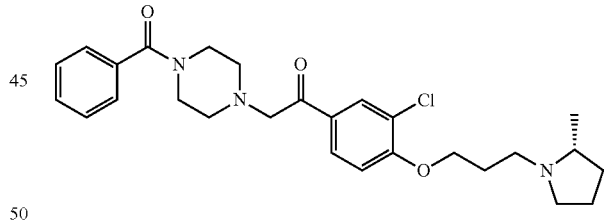

2-(4-Benzoyl-piperazin-1-yl)-1-{3-chloro-4-[3-((R)-2-methyl-pyrrolidin-1-yl)-propoxy]-phenyl}-ethanone

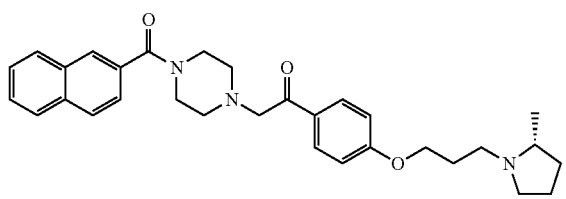

1-{4-[3-((R)-2-Methyl-pyrrolidin-1-yl)-propoxy]-phenyl}-2-[4-(naphthalene-2-carbonyl)-piperazin-1-yl]-ethanone

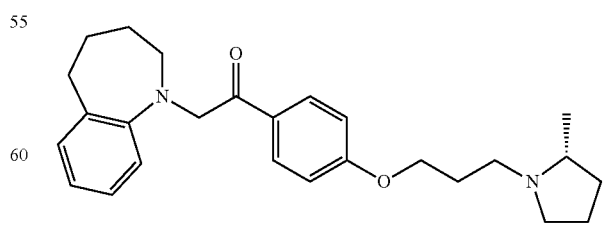

1-{4-[3-((R)-2-Methyl-pyrrolidin-1-yl)-propoxy]-phenyl}-2-(2,3,4,5-tetrahydro-benzo[b]azepin-1-yl)-ethanone -continued

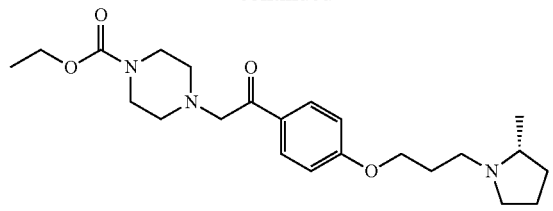 [SMILES: CCOC(=O)N1CCN(CC(=O)c2ccc(OCCCN3CCC[C@H]3C)cc2)CC1]

4-(2-{4-[3-((R)-2-Methyl-pyrrolidin-1-yl)-propoxyl]-phenyl}-2-oxo-ethyl)-piperazine-1-carboxylic acid ethyl ester

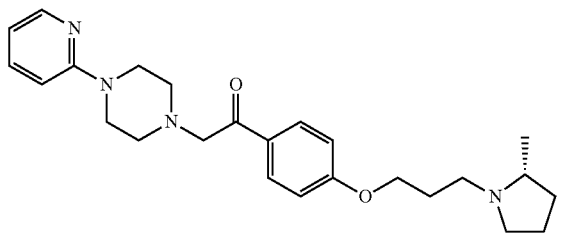

1-{4-[3-((R)-2-Methyl-pyrrolidin-1-yl)-propoxy]-phenyl}-2-(4-pyridin-2-yl-piperazin-1-yl)-ethanone

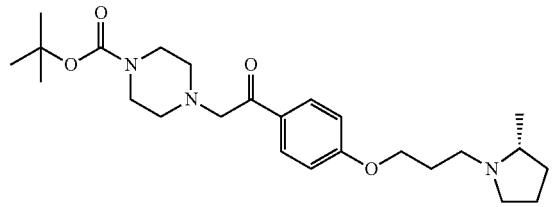 [SMILES: C[C@@H]1CCCN1CCCOc1ccc(C(=O)CN2CCN(C(=O)OC(C)(C)C)CC2)cc1]

4-(2-{4-[3((R)-2-Methyl-pyrrolidin-1-yl)-propoxy]-phenyl}-2-oxo-ethyl)-piperazine-1-carboxylic acid tert-butyl ester

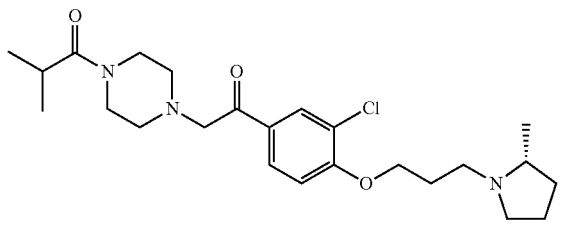

1-[4-(2-{3-Chloro-4-[3-((R)-2-methyl-pyrrolidin-1-yl)-propoxy]-phenyl}-2-oxo-ethyl)-piperazin-1-yl]-2-methyl-propan-1-one

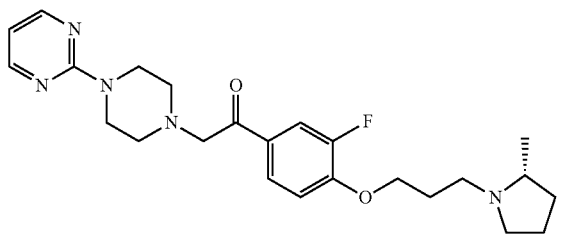

1{3-Fluoro-4-[3-((R)-2-methyl-pyrrolidin-1-yl)-propoxy]-phenyl}-2-(4-pyrimidin-2-yl-piperazin-1-yl)-ethanone

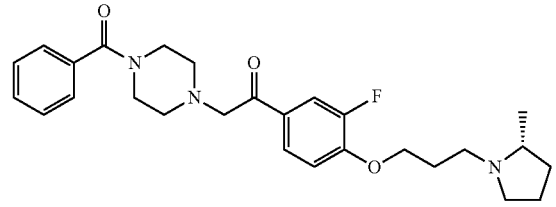 [SMILES: C[C@@H]1CCCN1CCCOc1ccc(C(=O)CN2CCN(C(=O)c3ccccc3)CC2)cc1F]

2-(4-Benzoyl-piperazin-1-yl)-1-{3-fluoro-4-[3-((R)-2-methyl-pyrrolidin-1-yl)-propoxy]-phenyl}-ethanone -continued

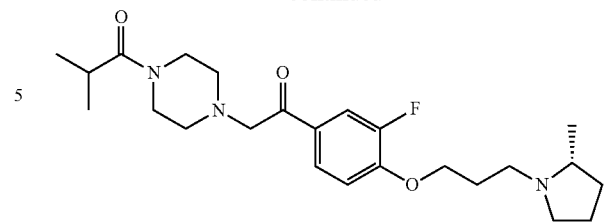

1-[4-(2-{3-Fluoro-4-[3-((R)-2-methyl-pyrrolidin-1-yl)-propoxy]-phenyl}-2-oxo-ethyl)-piperazin-1-yl]-2-methyl-propan-1-one

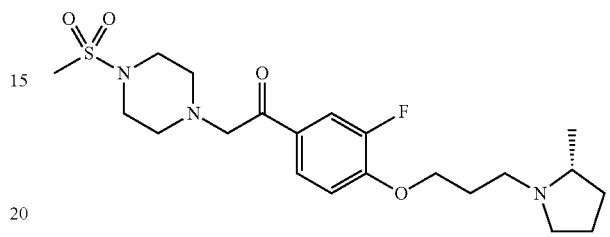

1-{3-Fluoro-4-[3-((R)-2-methyl-pyrrolidin-1-yl)-propoxy]-phenyl)-2-(4-methanesulfonyl-piperazin-1-yl)-ethanone

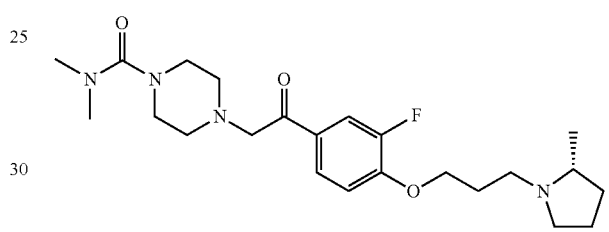

4-(2-{3-Fluoro-4-[3-((R)-2-methyl-pyrrolidin-1-yl)-propoxy]-phenyl}-2-oxo-ethyl)-piperazine-1-carboxylic acid dimethylamide

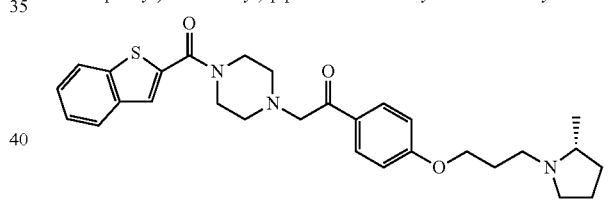

2-[4-(Benzo[b]thiophene-2-carbonyl)-piperazin-1-yl]-1-{4-[3-((R)-2-methyl-pyrrolidin-1-yl)-propoxy]-phenyl}-ethanone

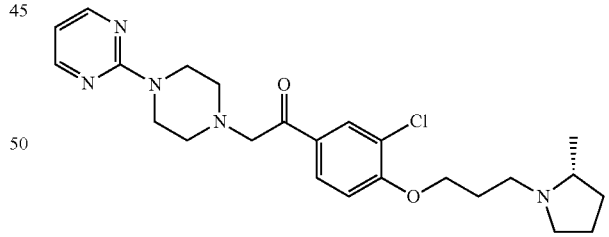

1-{3-Chloro-4-[3-((R)-2-methyl-pyrrolidin-1-yl)-propoxy]-phenyl}-2-(4-pyrimidin-2-yl-piperazin-1-yl)-ethanone

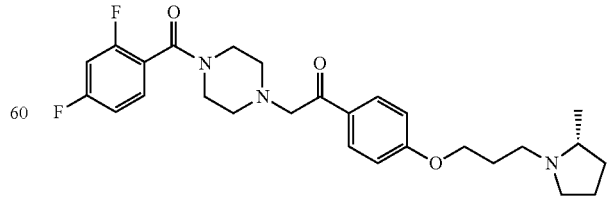

2-[4-(2-4-Difluoro-benzoyl)-piperazin-1-yl]-1-{4-[3-((R)-2-methyl-pyrrolidin-1-yl)-propoxy]-phenyl}-ethanone

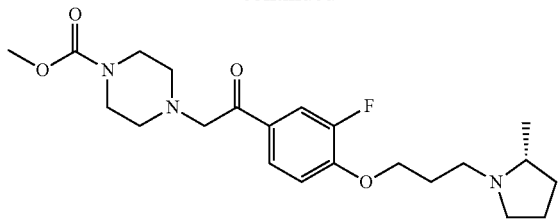 [SMILES: COC(=O)N1CCN(CC(=O)c2ccc(OCCCN3CCC[C@H]3C)c(F)c2)CC1]

4-(2-{3-Fluoro-4-[3-((R)-2-methyl-pyrrolidin-1-yl)-propoxyl-phenyl}-2-oxo-ethyl)-piperazine-1-carboxylic acid methyl ester

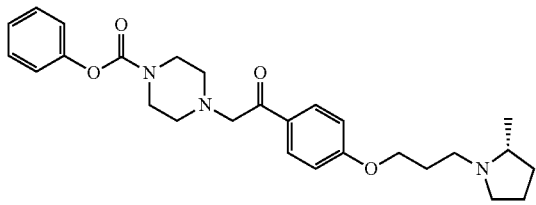 [SMILES: C[C@@H]1CCCN1CCCOc1ccc(C(=O)CN2CCN(C(=O)Oc3ccccc3)CC2)cc1]

4-(2-{4-[3-((R)-2-Methyl-pyrrolidin-1-yl)-propoxy]-phenyl}-2 oxo-ethyl)-piperazine-1-carboxylic acid phenyl ester

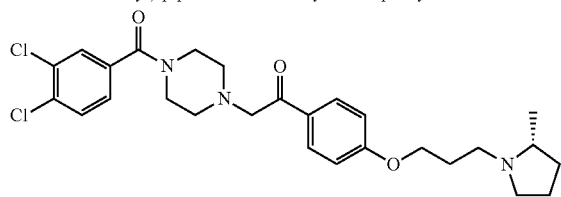

2-[4-(3,4-Dichloro-benzoyl)-piperazin-1-yl]-1-{4-[3-((R)-2-methyl-pyrrolidin-1-yl)-propoxy]-phenyl}-ethanone

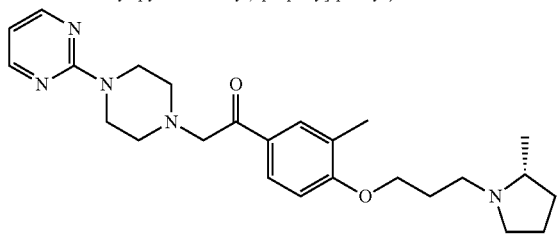

1-{3-Methyl-4-[3-((R)-2-methyl-pyrrolidin-1-yl)-propoxy]-phenyl}-2-(4-pyrimidin-2-yl-piperazin-1-yl)-ethanone

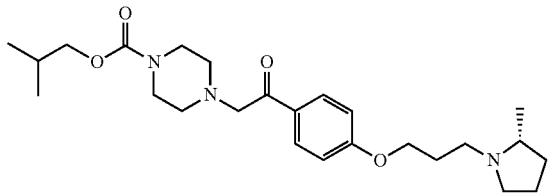 [SMILES: CC(C)COC(=O)N1CCN(CC(=O)c2ccc(OCCCN3CCC[C@H]3C)cc2)CC1]

4-(2-{4-[3-((R)-2-Methyl-pyrrolidin-1-yl)-propoxy]-phenyl}-2-oxo-ethyl)-piperazine-1-carboxylic acid isobutyl ester

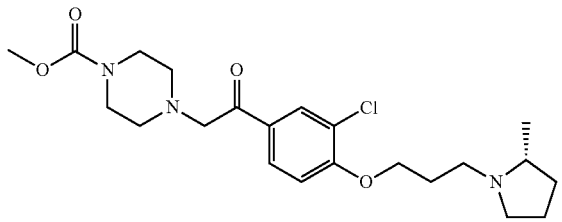

4-(2-{3-Chloro-4-[3-((R)-2-methyl-pyrrolidin-1-yl)-propoxy]-phenyl}-2-oxo-ethyl)-piperazine-1-carboxylic acid methyl ester

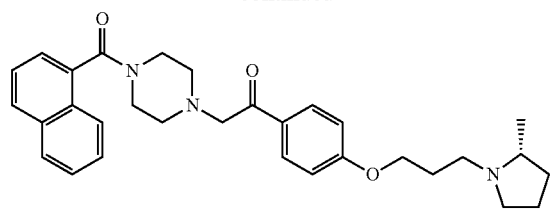 [SMILES: C[C@@H]1CCCN1CCCOc1ccc(C(=O)CN2CCN(C(=O)c3cccc4ccccc34)CC2)cc1]

1-{4-[3-((R)-2-Methyl-pyrrolidin-1-yl)-propoxy]-phenyl}-2-[4-(naphthalene-1-carbonyl)-piperazin-1-yl]-ethanone

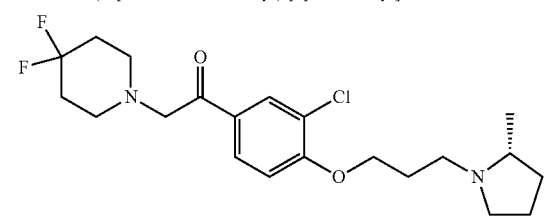

1-{3-Chloro-4-[3-((R)-2-methyl-pyrrolidin-1-yl)-propoxy]-phenyl}-2-(4,4-difluoro-piperidin-1-yl)-ethanone

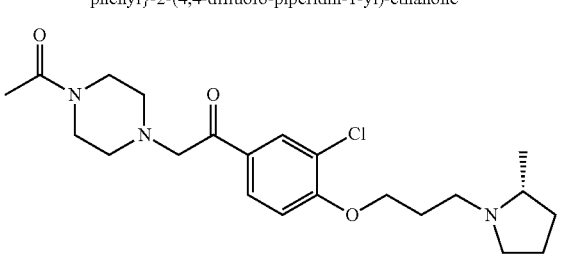

2-(4-Acetyl-piperazin-1-yl)-1-(3-chloro-4-[3-((R)-2-methyl-pyrrolidin-1-yl)-propoxy]-phenyl}-ethanone

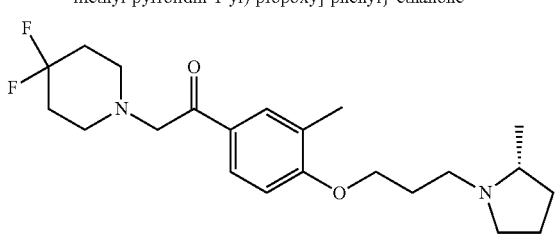

2-(4,4-Difluoro-piperidin-1-yl)-1-{3-methyl-4-[3-((R)-2-methyl-pyrrolidin-1-yl)-propoxy]-phenyl}-ethanone

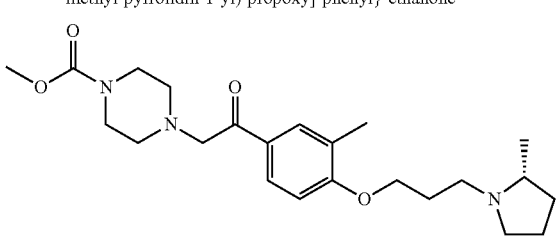

4-(2-{3-Methyl-4-[3-((R)-2-methyl-pyrrolidin-1-yl)-propoxy]-phenyl}-2-oxo-ethyl)-piperazine-1-carboxylic acid methyl ester

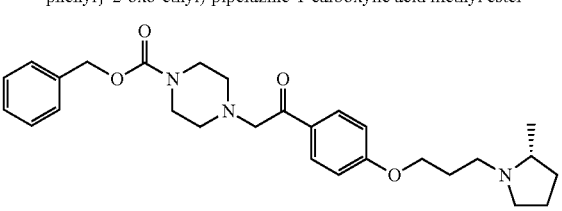

4-(2-{4-[3-((R)-2-Methyl-pyrrolidin-1-yl)-propoxy]-phenyl}-2-oxo-ethyl)-piperazine-1-carboxylic acid benzyl ester

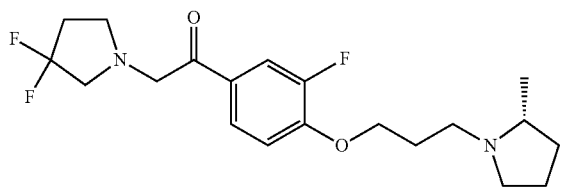 [SMILES: C[C@@H]1CCCN1CCCOc1ccc(C(=O)CN2CCC(F)(F)C2)cc1F]

2-(3,3-Difluoro-pyrrolidin-1-yl)-1-{3-fluoro-4-[3-((R)-
2-methyl-pyrrolidin-1-yl)-propoxy}-phenyl}-ethanone

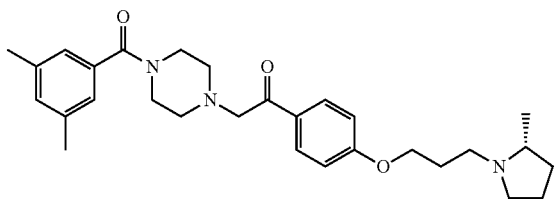 [SMILES: Cc1cc(C)cc(C(=O)N2CCN(CC(=O)c3ccc(OCCCN4CCC[C@H]4C)cc3)CC2)c1]

2-[4-(3,5-Dimethyl-benzoyl)-piperazin-1-yl]-1-{4-[3-((R)-2-
methyl-pyrrolidin-1-yl)-propoxy]-phenyl}-ethanone

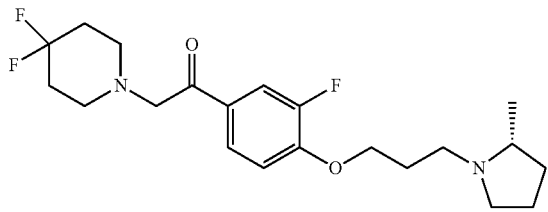

2-{4,4-Difluoro-piperidin-1-yl)-1-{3-fluoro-4-[3-
((R)-2-methyl-pyrrolidin-1-yl)-propoxy]-phenyl}-ethanone

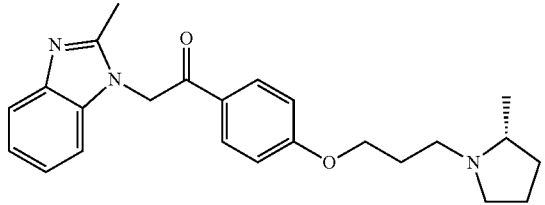 [SMILES: Cc1nc2ccccc2n1CC(=O)c1ccc(OCCCN2CCC[C@H]2C)cc1]

2-(2-Methyl-benzoimidazol-1-yl)-1-{4-[3-((R)-2-methyl-
pyrrolidin-1-yl)-propoxy]-phenyl}-ethanone

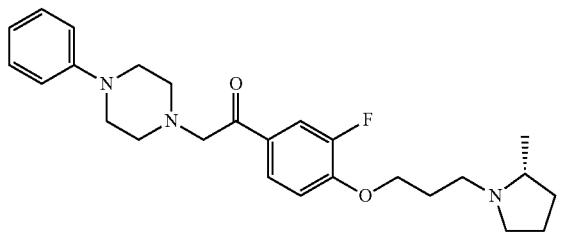 [SMILES: C[C@@H]1CCCN1CCCOc1ccc(C(=O)CN2CCN(c3ccccc3)CC2)cc1F]

1-{3-Fluoro-4-[3-((R)-2-methyl-pyrrolidin-1-yl)-
propoxy]-phenyl}-2-(4-phenyl-piperazin-1-yl)-ethanone

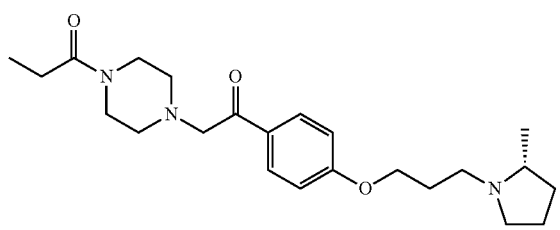 [SMILES: CCC(=O)N1CCN(CC(=O)c2ccc(OCCCN3CCC[C@H]3C)cc2)CC1]

1-[4-(2-{4-[3-((R)-2-Methyl-pyrrolidin-1-yl)-propoxy]-
phenyl}-2-oxo-ethyl)-piperazin-1-yl]-propan-1-one

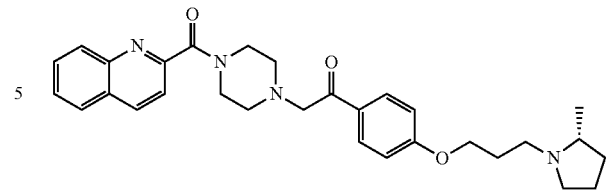

1-{4-[3-((R)-2-Methyl-pyrrolidin-1-yl)-propoxy]-phenyl}-
2-[4-(quinoline-2-carbonyl)-piperazin-1-yl]-ethanone

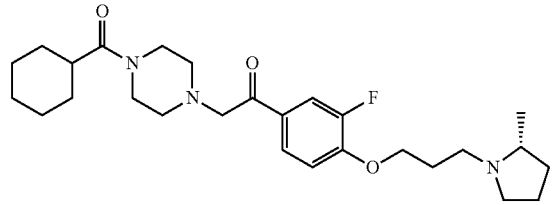 [SMILES: C[C@@H]1CCCN1CCCOc1ccc(C(=O)CN2CCN(C(=O)C3CCCCC3)CC2)cc1F]

2-(4-Cyclohexanecarbonyl-piperazin-1-yl)-1-{3-fluoro-4-[3-
((R)-2-methyl-pyrrolidin-1-yl)-propoxy]-phenyl}-ethanone

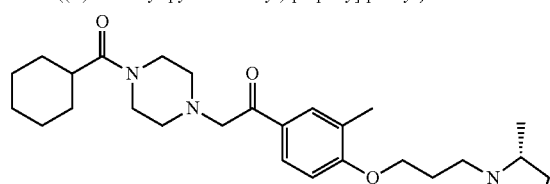

2-(4-Cyclohexanecarbonyl-piperazin-1-yl)-1-{3-methyl-4-[3-
((R)-2-methyl-pyrrolidin-1-yl)-propoxy]-phenyl}-ethanone

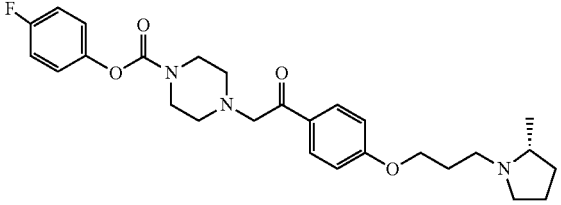

4-(2-{4-[3-((R)-2-Methyl-pyrrolidin-1-yl)-propoxy]-phenyl}-2-
oxo-ethyl)-piperazine-1-carboxylic acid 4-fluoro-phenyl ester

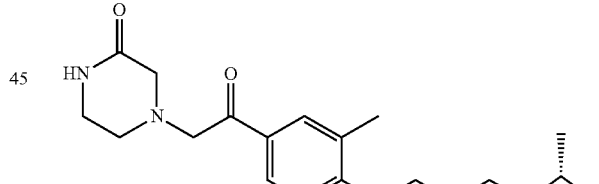

4-(2-{3-Methyl-4-[3-((R)-2-methyl-pyrrolidin-1-yl)-
propoxy]-phenyl}-2-oxo-ethyl)-piperazin-2-one

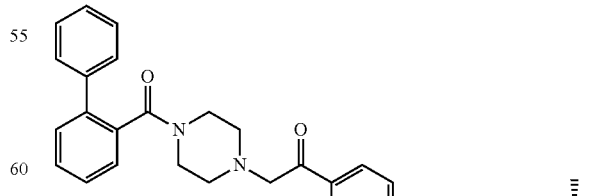

2-[4-(Biphenyl-2-carbonyl)-piperazin-1-yl]-1-{4-[3-((R)-
2-methyl-pyrrolidin-1-yl)-propoxy]-phenyl}-ethanone -continued

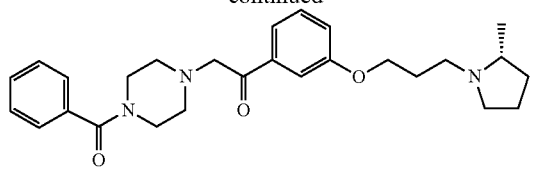

2-(4-Benzoyl-piperazin-1-yl)-1-{3-[3-((R)-2-methyl-pyrrolidin-1-yl)-propoxy]-phenyl}-ethanone

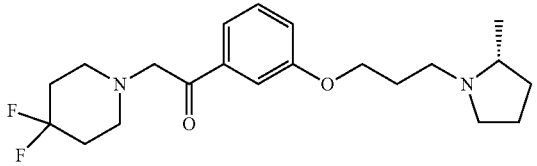

2-(4,4-Difluoro-piperidin-1-yl)-1-{3-[3-((R)-2-methyl-pyrrolidin-1-yl)-propoxy]-phenyl}-ethanone

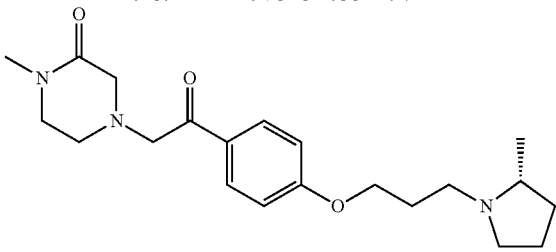

1-Methyl-4-(2-{4-[3-((R)-2-methyl-pyrrolidin-1-yl)-propoxy]-phenyl}-2-oxo-ethyl)-piperazin-2-one

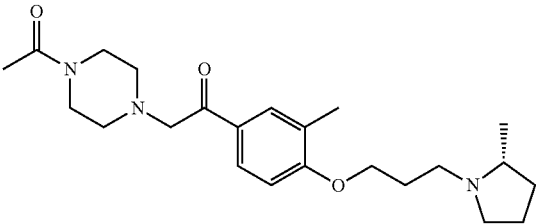

2-(4-Acetyl-piperazin-1-yl)-1-{3-methyl-4-[3-((R)-2-methyl-pyrrolidin-1-yl)-propoxy]-phenyl}-ethanone -continued

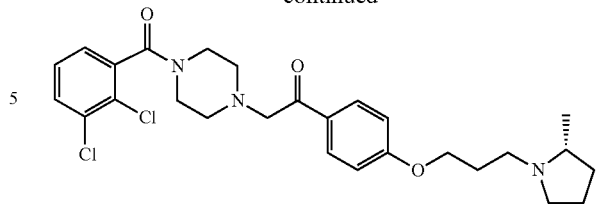

2-[4-(2,3-Dichloro-benzoyl)-piperazin-1-yl]-1-{4-[3-((R)-2-methyl-pyrrolidin-1-yl)-propoxy]-phenyl}-ethanone

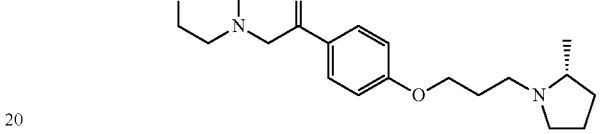

4-(2-{4-[3-((R)-2-Methyl-pyrrolidin-1-yl)-propoxy]-phenyl}-2-oxo-ethyl)-piperazine-1-carboxylic acid isopropyl ester or a pharmaceutically acceptable salt thereof.

18. A pharmaceutical composition comprising a compound of claim 1 or a stereoisomer or a pharmaceutically acceptable salt thereof and one or more pharmaceutically acceptable excipients.

19. A pharmaceutical composition comprising a compound of claim 8 or a stereoisomer or a pharmaceutically acceptable salt thereof and one or more pharmaceutically acceptable excipients.

20. A pharmaceutical composition comprising a compound of claim 13 or a stereoisomer or a pharmaceutically acceptable salt thereof and one or more pharmaceutically acceptable excipients.

21. A pharmaceutical composition comprising a compound of claim 17 or a pharmaceutically acceptable salt thereof and one or more pharmaceutically acceptable excipients.

* * * * *